US012577547B2

(12) United States Patent (10) Patent No.: US 12,577,547 B2
Jarjour et al. (45) Date of Patent: Mar. 17, 2026

(54) PDCD-1 HOMING ENDONUCLEASE VARIANTS

(71) Applicant: REGENERON PHARMACEUTICALS, INC., Tarrytown, NY (US)

(72) Inventors: Jordan Jarjour, Seattle, WA (US); Kyle Havens, Seattle, WA (US); Jasdeep Mann, Lake Forest Park, WA (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 1319 days.

(21) Appl. No.: 17/311,455

(22) PCT Filed: Dec. 9, 2019

(86) PCT No.: PCT/US2019/065223
§ 371 (c)(1),
(2) Date: Jun. 7, 2021

(87) PCT Pub. No.: WO2020/123375
PCT Pub. Date: Jun. 18, 2020

(65) Prior Publication Data
US 2022/0177860 A1 Jun. 9, 2022

Related U.S. Application Data

(60) Provisional application No. 62/777,471, filed on Dec. 10, 2018.

(51) Int. Cl.
*C12N 9/22* (2006.01)
*A61K 35/17* (2015.01)
(Continued)

(52) U.S. Cl.
CPC ............... *C12N 9/22* (2013.01); *A61K 35/17* (2013.01); *A61K 38/465* (2013.01); *A61K 48/00* (2013.01);
(Continued)

(58) Field of Classification Search
CPC ........ C12N 9/22; C12N 15/85; C12N 15/907; A61K 35/17
See application file for complete search history.

(56) References Cited

U.S. PATENT DOCUMENTS

| 4,751,180 A | 6/1988 | Cousens et al. |
| 4,873,192 A | 10/1989 | Kunkel |

(Continued)

FOREIGN PATENT DOCUMENTS

| CN | 101679959 A | 3/2010 |
| CN | 106749666 A | 5/2017 |

(Continued)

OTHER PUBLICATIONS

GenPept 6BDO_A (available through NCBI; disclosed by Brown,C., Zhang, K., Laforet,M., McMurrough,T.A., Gloor,G.B., Edgell,D.R. and Junop,M. in 2017) (Year: 2017).*

(Continued)

*Primary Examiner* — Manjunath N Rao
(74) *Attorney, Agent, or Firm* — Panitch Schwarze Belisario & Nadel LLP; Stephany G. Small; Travis W. Bliss

(57) ABSTRACT

The present disclosure provides improved homing endonuclease variants and megaTALs reprogrammed to bind and cleave the PDCD-1 gene.

18 Claims, 4 Drawing Sheets
Specification includes a Sequence Listing.

(51) Int. Cl.

| | | |
|---|---|---|
| *A61K 38/46* | (2006.01) |
| *A61K 48/00* | (2006.01) |
| *C12N 5/0783* | (2010.01) |
| *C12N 15/85* | (2006.01) |
| *C12N 15/90* | (2006.01) |

(52) U.S. Cl.

CPC ........... *C12N 5/0636* (2013.01); *C12N 15/85* (2013.01); *C12N 15/907* (2013.01); *C12N 2800/80* (2013.01)

(56) References Cited

U.S. PATENT DOCUMENTS

| | | | |
|---|---|---|---|
| 4,935,233 | A | 6/1990 | Bell et al. |
| 5,804,413 | A | 9/1998 | DeLuca |
| 5,837,532 | A | 11/1998 | Preston et al. |
| 5,846,782 | A | 12/1998 | Wickham et al. |
| 5,994,136 | A | 11/1999 | Naldini et al. |
| 6,013,516 | A | 1/2000 | Verma et al. |
| 6,649,595 | B2 | 11/2003 | Clackson et al. |
| 6,682,907 | B1 | 1/2004 | Charneau et al. |
| 6,692,736 | B2 | 2/2004 | Yu et al. |
| 8,614,092 | B2 | 12/2013 | Zhang et al. |
| 8,735,553 | B1 | 5/2014 | Li et al. |
| 8,784,799 | B2 | 7/2014 | Samulski et al. |
| 8,809,058 | B2 | 8/2014 | Ferrari et al. |
| 8,889,641 | B2 | 11/2014 | Asokan et al. |
| 9,012,224 | B2 | 4/2015 | Bowles et al. |
| 9,017,967 | B2 | 4/2015 | Bonas et al. |
| 9,169,492 | B2 | 10/2015 | Monahan et al. |
| 9,169,494 | B2 | 10/2015 | Hewitt et al. |
| 9,506,120 | B2 | 11/2016 | Doyon et al. |
| 11,345,754 | B2 | 5/2022 | Hu et al. |
| 11,365,226 | B2 * | 6/2022 | Mann ................. A61K 40/4215 |
| 11,779,654 | B2 | 10/2023 | Jarjour et al. |
| 2011/0256607 | A1 | 10/2011 | Hausner |
| 2013/0337454 | A1 | 12/2013 | Duchateau et al. |
| 2014/0148361 | A1 | 5/2014 | Stoddard et al. |
| 2015/0266973 | A1 | 9/2015 | Jarjour et al. |
| 2016/0102323 | A1 | 4/2016 | Jarjour et al. |
| 2016/0130569 | A1 | 5/2016 | Jarjour et al. |
| 2017/0298329 | A1 | 10/2017 | Takeuchi |
| 2021/0040165 | A1 * | 2/2021 | Mann ................. C07K 14/4702 |

FOREIGN PATENT DOCUMENTS

| | | | |
|---|---|---|---|
| CN | 106939049 A | 7/2017 |
| EA | 201492222 | 5/2015 |
| EP | 2215223 B1 | 5/2013 |
| IN | 201617011596 | 12/2016 |
| JP | 2010539929 A | 12/2010 |
| JP | 2016520308 A | 7/2016 |
| WO | WO 91/02788 | 3/1991 |
| WO | WO 96/04394 | 2/1996 |
| WO | WO 98/15637 | 4/1998 |
| WO | WO 99/06583 | 2/1999 |
| WO | WO 2006/010834 | 2/2006 |
| WO | WO 2007/049095 | 5/2007 |
| WO | WO 2011/156430 | 12/2011 |
| WO | WO 2012/068380 | 5/2012 |
| WO | WO 2012/118717 | 9/2012 |
| WO | WO 2013/126794 | 8/2013 |
| WO | 201414744 A1 | 1/2014 |
| WO | 2014184744 A1 | 11/2014 |
| WO | WO 2014/184741 | 11/2014 |
| WO | WO 2014/191525 | 12/2014 |
| WO | WO 2014/191527 | 12/2014 |
| WO | WO 2015/017214 | 2/2015 |
| WO | WO 2017/156484 | 9/2017 |
| WO | WO 2017/177137 | 10/2017 |
| WO | WO 2018/022619 | 2/2018 |
| WO | WO 2018/035141 | 2/2018 |
| WO | WO 2018/035423 | 2/2018 |
| WO | WO 2018/039333 | 3/2018 |
| WO | WO 2018/049226 | 3/2018 |
| WO | WO-2018049226 A1 * | 3/2018 | ............. A61K 35/17 |
| WO | 2018071565 | 4/2018 |
| WO | WO 2018/075541 | 4/2018 |
| WO | WO 2018/218194 | 11/2018 |
| WO | 2020072059 A1 | 4/2020 |
| WO | 2020123375 | 6/2020 |

OTHER PUBLICATIONS

Lambert et al., 2016, Indirect DNA sequence recognition and its impact on nuclease cleavage activity (Year: 2016).*

Ashworth et al., "Computational redesign of endonuclease DNA binding and cleavage specificity," Nature, Jun. 1, 2006, 441(7093): pp. 656-659.

Balazs et al., "Liposomes for use in gene delivery," Journal of Drug Delivery 2011, 1-12.

Baxter Sarah et al: "Engineering domain fusion chimeras from 1-Onul family LAGLIDADG homing endonucleases.", Nucleic Acids Research Sep. 2012, vol. 40, No. 16, Sep. 2012 (Sep. 2012), pp. 7985-8000.

Belfort et al., "Homing Endonucleases: From Genetic Anomalies to Programmable Genomic Clippers," Methods in Molecular Biology,Jan. 1, 2014, vol. 1123, pp. 1-26.

Bennardo et al., "Limiting the Persistence of a Chromosome Break Diminishes Its Mutagenic Potential," PLoS Genetics, Oct. 16, 2009, vol. 5, Issue 10, 14 pages.

Bird, Robert E., et al. "Single-chain antigen-binding proteins." Science (1988); 242.4877: 423-427.

Boissel et al., "megaTALs: a rare-cleaving nuclease architecture for therapeutic genome engineering," Nucleic Acids Research, 2013, 42(4):2591-2601.

Brinkman et al., "Easy quantitative assessment of genome editing by sequence trace decomposition" Nucleic Acids Res. Dec. 16, 2014;42(22).

Brown, E. et al., "A mammalian protein targeted by G1-arresting rapamycin-receptor complex", Nature (1994); 369(6483): 756-758.

Brunner et al., "Cytotoxic T cells: Double-barreled shot guns," Nature Medicine, vol. 5, No. 1, Jan. 1999, 1 page.

Certo et al., "Tracking genome engineering outcome at individual DNA breakpoints," Nat Methods. Jul. 10, 2011;8(8):671-6.

Certo et al., "Coupling endonucleases with DNA end-processing enzymes to drive gene disruption," Nat Methods, Oct. 2012, 9(10), 973-975.

Challita, P. et al., "Multiple modifications in cis elements of the long terminal repeat of retroviral vectors lead to increased expression and decreased DNA methylation in embryonic carcinoma cells." J Virol. (1995); 69(2): 748-755.

Chaudhary, Vuay K., et al. "A rapid method of cloning functional variable-region antibody genes in *Escherichia coli* as single-chain immunotoxins." Proceedings of the National Academy of Sciences (1990); 87.3: 1066-1070 (and correction).

Chevalier et al., "Design, Activity, and Structure of a Highly Specific Artificial Endonuclease," Molecular Cell, vol. 10, pp. 895-905, Oct. 2002.

Clever, J. et al., "RNA Secondary Structure and Binding Sites for gag Gene Products in the 5'Packaging Signal of Human Immunodeficiency Virus Type 1." J. of Virology (1995); 69(4): 2101-2109.

Cullen, B.R., "Human Immunodeficiency Virus as a Prototypic Complex Retrovirus", Journal of Virology (1991); 65(3): 1053-1056.

Cullen et al., "Regulatory Pathways Governing HIV-1 Replication", Cell (1989); 58: 423-426.

Database Geneseq [Online] Oct. 24, 2013 (Oct. 24, 2013), "I-Onul homing endonuclease, SEQ 15.", XP002798406, retrieved from EBI accession No. GSP:BAS88181 Database accession No. BAS88181 * sequence *.

Dayhoff, M. et al., "A model of evolutionary change in proteins. In: Atlas of Protein Sequenceand Structure", M.O. Dayhoff, (1978) ed., pp. 345-358. National Biomedical Research Foundation, Washington, DC.

(56)         References Cited

OTHER PUBLICATIONS

De Felipe et al., "Targeting of proteins derived from self-processing polyproteins containing multiple signal sequences." Traffic (2004); 5.8: 616-626.

Desjarlais et al., "Use of a zinc-finger consensus sequence framework and specificity rules todesign specific DNA binding proteins." Proceedings of the National Academy of Sciences (1993); 90.6: 2256-2260.

Desjarlais et al., "Length-encoded multiplex binding site determination: application to zinc finger proteins," Proceedings of the National Academy of Sciences (1994); 91.23: 11099-11103.

Donnelly, M. et al., "The 'cleavage' activities of foot-and-mouth disease virus 2A site-directed mutants and naturally occurring '2A-like' sequences." J Gen Virol. (2001); 82 (Pt 5): 1027-1041.

Duan et al., "Expanding AAV Packaging Capacity with Trans-splicing or Overlapping Vectors: A Quantitative Comparison," Mol Ther. Oct. 2001;4(4):383-91.

Duke et al., Sequence and structural elements that contribute to efficient encephalomyocarditis virus RNA translation, J Virol. Mar. 1992;66(3):1602-9.

Dull et al., "A third-generation lentivirus vector with a conditional packaging system", Journal of Virology (1998); 72(11): 8463-8671.

Epinat et al., "A novel engineered meganuclease induces homologous recombination in yeast and mammalian cells," Nucleic Acids Research, 2003, vol. 31, No. 11, pp. 2952-2962.

Extended European Search Report mailed on Jun. 15, 2020, for European Application No. 17849655.0, 9 pages.

GenBank Accession No. L34075.1, "Human FKBP-rapamycin associated protein (FRAP) mRNA, complete cds," Dec. 31, 1994, 4 pages.

GenBank Accession No. AAA58476.1, "FK506-binding protein 12 [Homo sapiens]," Jun. 10, 2016, 2 pages.

Ghosh et al., "Viral serotype and the transgene sequence influence overlapping adeno-associated viral (AAV) vector-mediated gene transfer in skeletal muscle," J Gene Med. Mar. 2006;8(3):298-305.

Ghosh et al., "A Hybrid Vector System Adeno-associated Viral Vector Packaging Capacity in a Transgene-independent Manner," Mol Ther. Jan. 2008;16(1):124-30. Epub Nov. 6, 2007.

Ghosh et al., "Efficient Transgene Reconstitution with Hybrid Dual AAV Vectors Carrying the Minimized Bridging Sequences," Hum Gene Ther. Jan. 2011;22(1):77-83.

Gomez-Foix et al., "Adenovirus-mediated Transfer of the Muscle Glycogen Phosphorylase Geneinto Hepatocytes Confers Altered Regulation of Glycogen Metabolism," J Biol Chem. Dec. 15, 1992;267(35):25129-34.

Graham et al., "Characteristics of a Human Cell Line Transformed by DNA from Human Adenovirus Type 5," J. gen. Virol. 1977, 36, 59-72.

Graham & Preveck, "Chapter 11, Manipulation of Adenovirus Vectors," Methods in Molecular Biology, vol. 7: Gene transfer and Expression Protocols, 1991.

Graham & Preveck, "Adenovirus-Based Expression Vectors and Recombinant Vaccines" Vaccines: New Approaches to Immunological Problems, 1992.

Grunhaus, A., and Horwitz, M. S. "Adenoviruses as cloning vectors," Semin. Virol. 1992; 3, 237-252.

Hensgens et al., "Two Intron Sequences in Yeast Mitochondrial COX1 Gene: Homology among URF-Containing Introns and Strain-Dependent Variation in Flanking Exons," Cell, vol. 32, 379-389, Feb. 1983.

Herz & Gerard, "Adenovirus-mediated transfer of low density lipoprotein receptor gene acutely accelerates cholesterol clearance in normal mice," PNAS, 1993, vol. 90, 2812-2816.

Huang et al., "Role of the hepatitis B virus posttranscriptional regulatory element in export of intronless transcripts," Molecular and Cellular Biology (1995); 15(7): 3864-3869.

Huez et al., "Two independent internal ribosome entry sites are involved in translation initiation of vascular endothelial growth factor mRNA," Mol Cell Biol. Nov. 1998;18(11):6178-90.

International Search Report and Written Opinion mailed on Nov. 16, 2017, for International Application No. PCT/US2017/050774, 11 pages.

International Search Report and Written Opinion mailed on Mar. 4, 2020, for International Application No. PCT/US2019/065223, 10 pages.

Irion, S. et al., "Identification and targeting of the ROSA26 locus in human embryonic stem cells", Nat Biotechnol. (2007); 25(12):1477-1482.

Jackson, et al., "The novel mechanism of initiation of picornavirus RNA translation", Trends Biochem Sci. (1990); 15(12): 477-483.

Jackson, et al., "Internal initiation of translation in eukaryotes: the picornavirus paradigm and beyond", RNA. (1995); 1(10): 985-1000.

Jarjour et al., "High-resolution profiling of homing endonuclease binding and catalytic specificity using yeast surface display," 2009. Nuc. Acids Res. 37(20): 6871-6880.

Jones & Shenk, Isolation of Deletion and Substitution Mutants of Adenovirus Type 5, Cell 1978, vol. 13, 181-188.

Kay, J.E. "Structure-function relationships in the FK506-binding protein (FKBP) family of peptidylprolyl cis-trans isomerases", Biochem J. (1996); 314 (Pt 2):361-385.

Kay et al., "A bacterial effector acts as a plant transcription factor and induces a cell size regulator," Science. Oct. 26, 2007;318(5850):648-51.

Kim, Yang-Gyun,et al. "Hybrid restriction enzymes: zinc finger fusions to Fok I cleavage domain." Proceedings of the National Academy of Sciences (1996); 93.3: 1156-1160.

Kozak, M., "Point mutations define a sequence flanking the AUG initiator codon that modulates translation by eukaryotic ribosomes", Cell (1986); 44(2): 283-292.

Kozak, M., "An analysis of 5'-noncoding sequences from 699 vertebrate messenger RNAs", Nucleic Acids Res. (1987); 15(20): 8125-8148.

Kunkel, TA. "Rapid and efficient site-specific mutagenesis without phenotypic selection", Proc Natl Acad Sci U S A. (1985); 82(2): 488-492.

Kunkel, et al "Rapid and efficient site-specific mutagenesis without phenotypic selection", Methods in Enzymol. (1987); 154: 367-382.

Kutner, et al., "Simplified production andconcentration of HIV-1-based lentiviral vectors using HYPERFlask vessels and anion exchange membrane chromatography", BMC Biotechnol. (2009); 9:10. p. 1-7.

Kutner et al., "Production, concentration and titration of pseudotyped HIV-1-based lentiviral vectors", Nature Protocols (2009); 4: 495-505.

Lai et al., "Long-Term Evaluation of AAV-Mediated sFlt-1Gene Therapy for OcularNeovascularization in Mice and Monkeys," Molecular Therapy, vol. 12, No. 4, Oct. 2005, 10 pages.

Le Gal La Salle et al., "An Adenovirus Vector for Gene Transfer into Neurons and Glia in the Brain," Science Feb. 12, 1993, vol. 259, 988-990.

Levrero et al., "Defective and nondefective adenovirus vectors for expressing foreign genes in vitro and in vivo," Gene 1991; 101:195-202.

Liu et al., "HnRNP L binds a cis-acting RNA sequence element that enables intron-dependent gene expression," Genes & Dev. (1995); 9: 1766-1780.

Liu et al., "Design of polydactyl zinc-finger proteins for unique addressing within complex genomes," Proceedings of the National Academy of Sciences (1997); 94.11: 5525-5530.

Liu et al., "Poly(cationic lipid)-mediated in vivo gene delivery to mouse liver," Gene Ther. Jan. 2003;10(2):180-7.

Maratea et al., "Deletion and fusion analysis of the phage phi X174 lysis gene E," Gene. 1985;40(1):39-46.

Mcmurrough et al., "Control of catalytic efficiency by a coevolving network of catalytic and noncatalytic residues," May 27, 2014, PNAS: E2376-E2383.

Murphy et al., "Genetic construction, expression, and melanoma-selective cytotoxicity of adiphtheria toxin-related alpha-melanocyte-stimulating hormone fusion protein," Proc Natl Acad Sci U S A. Nov. 1986;83(21):8258-62.

(56)        References Cited

OTHER PUBLICATIONS

Naldini L. et al., "Efficient transfer, integration, and sustained long-term expression of thetransgene in adult rat brains injected with a lentiviral vector", Proc Natl Acad Sci USA (1996); 93(21): 11382-11388.

Naldini, L. et al., "In vivo gene delivery and stable transduction of nondividing cells by a lentiviral vector", Science (1996); 272(5259): 263-267.

Naldini, L., "Lentiviruses as gene transfer agents for delivery to non-dividing cells", Curr Opin Biotechnol. (1998); 5: 457-463.

Paques et al., "Meganucleases and DNA Double-Strand Break-Induced Recombination: Perspectives for Gene Therapy," Current Gene Therapy, 2007, 7, pp. 49-66.

Patel, S. et al., "Impact of chimeric immune receptor extracellular protein domains on T cell function." Gene Ther (1999); 6(3): 412-419.

Platten et al., "Tryptophan catabolismin cancer: beyond IDO and tryptophan depletion," Cancer Res. Nov. 1, 2012;72(21):5435-40.

Pomerantz, et al., "Structure-based design of transcription factors." Science (1995); 267.5194: 93-96.

Pomerantz, et al., "Analysis of homeodomain function by structure-based design of a transcription factor," Proc Natl Acad Sci U S A. Oct. 10, 1995;92(21):9752-6.

Ragot et al., "Efficient adenovirus-mediated transfer of a human minidystrophin gene to skeletal muscle of mdx mice," Nature Feb. 18, 1993; vol. 361: 647-650.

Reich et al., "Efficient Trans-Splicing in the Retina Expands the Utility of Adeno-Associated Virus as a Vector for Gene Therapy," Hum Gene Ther. Jan. 1, 2003;14(1):37-44.

Rosenfeld et al., "Adenovirus-Mediated Transfer of a Recombinant α1-Antitrypsin Gene to the Lung Epithelium in Vivo," Science Apr. 19, 1991; vol. 252: 431-434.

Rosenfeld et al., "In vivo transfer of the human cystic fibrosis transmembrane conductance regulator gene to the airway epithelium," Cell, Jan. 10, 1992; vol. 68: 143-155.

Ryan, M. et al., "Virus-encoded proteinases of the picornavirus super-group." J Gen Virol. (1997); 78 (Pt 4): 699-723.

Sather et al., "Efficient modification of CCR5 in primary human hematopoietic cells using amegaTAL nuclease and AAV donor template," Sci Transl Med., Sep. 30, 2015, vol. 7, issue 307, 14 pages.

Standaert, R. et al., "Molecular cloning and overexpression of the human FK506-binding protein FKBP", Nature (1990); 346(6285): 671-674.

Sterman et al., "Adenovirus-mediated herpes simplex virus thymidine kinase/ganciclovir genetherapy in patients with localized malignancy: results of a phase I clinical trial in malignant mesothelioma," Hum Gene Ther. May 1, 1998;9(7):1083-92.

Stoddard, "Homing endonuclease structure and function," Quarterly Reviews of Biophysics 2005; 38(1): pp. 49-95.

Stoddard, "Homing Endonucleases: From Microbial Genetic Invaders to Reagents for Targeted DNA Modification," Structure 19, Jan. 12, 2011, 9 pages.

Szymczak, Andrea L., et al. "Correction of multi-gene deficiency in vivo using a single'self-cleaving'2A peptide-based retroviral vector." Nature Biotechnology (2004); 22.5: 589-594.

Takeuchi et al:"Tapping natural reservoirs of homing endonucleases for targeted genemodification", Proceedings of the National Academy of Sciences, National Academy of Sciences, vol. 108, o. 32, Aug. 1, 2011 {Aug. 1, 2011), pp. 13077-13082.

Takeuchi et al., "Engineering of customized meganucleases via in vitro compartmentalization and in cellulo optimization," Methods Mol Biol. 2015; 1239: 105-132.

Yan et al., "Trans-splicing vectors expand the utility of adeno-associated virus for gene therapy," PNAS, Jun. 6, 2000, vol. 97, No. 12, 6 pages.

Zennou et al., "HIV-1 genome nuclear import is mediated by a central DNA flap," Cell. Apr. 14, 2000;101(2):173-85.

Zhong et al., "Chimeric antigen receptors combining 4-1BB and CD28 signaling domainsaugment PI3kinase/AKT/Bcl-XL activation and CD8+ T cell-mediated tumor eradication," Mol Ther. Feb. 2010; 18(2): 413-420.

Zufferey et al., "Multiply attenuated lentiviral vector achieves efficient gene delivery in vivo", Nat Biotechnol. (1997), 15(9): 871-875.

Zufferey, R. et al., "Woodchuck hepatitis virus posttranscriptional regulatory element enhances expression of transgenes delivered by retroviral vectors." J Virol. (1999); 73(4): 2886-2892.

Nakayama et al., "Structure of a Hyperthermophilic Archael Homing Endonuclease, I-Tsp061I: Contribution of Cross- domain Polar Networks to Thermostability," Journal of Molecular Biology, vol. 365, pp. 362-378 (2007).

International Search Report and Written Opinion issued Jul. 20, 2020 in International Application No. PCT/US2019/065211.

Chan et al, The Design and In Vivo Evaluation of Engineered I-Onul-based Enzymes for HEG Gene Drive, 8(9) PLoS One 1-5 (Sep. 2013).

Cox et al., Therapeutic genome editing: prospects and challenges, 21(2) Nature Medicine 121-131 (2015).

Sethuraman et al., Genes within Genes: Multiple LAGLIDADG Homing Endonucleases Target the Ribosomal Protein S3 Gene Encoded within an rnl Group I Intron of Ophiostoma and Related Taxa, 26(10) Mol Biol Evol. 2299-2315 (2009).

Zhang et al., Research progress in engineered nucleases for genome site-specific editing, 33(12) Basic & Clinical Medicine 1634-1637 (Dec. 2013) (English abstract).

* cited by examiner

PDCD-1 HOMING ENDONUCLEASE VARIANTS

CROSS REFERENCE TO RELATED APPLICATIONS

This application is a National Stage application under 35 U.S.C. § 371 of International Application No. PCT/US2019/065223, filed Dec. 9, 2019, which claims the benefit under 35 U.S.C. § 119(e) of U.S. Provisional Application No. 62/777,471, filed Dec. 10, 2018, each of which are incorporated by reference herein in their entirety.

STATEMENT REGARDING SEQUENCE LISTING

The Sequence Listing associated with this application is provided in text format in lieu of a paper copy and is hereby incorporated by reference into the specification. The name of the text file containing the Sequence Listing is BLBD_109_01WO_ST25.txt. The text file is 95 KB, created on Nov. 26, 2019, and is being submitted electronically via EFS-Web, concurrent with the filing of the specification.

BACKGROUND

Technical Field

The present disclosure relates to genome editing compositions with improved stability and activity. More particularly, the disclosure relates to improved nuclease variants, compositions, and methods of using the same for editing the human program cell death 1 (PDCD-1) gene.

Description of the Related Art

The global burden of cancer doubled between 1975 and 2000. Cancer is the second leading cause of morbidity and mortality worldwide, with approximately 14.1 million new cases and 8.2 million cancer related deaths in 2012. The most common cancers are breast cancer, lung and bronchus cancer, prostate cancer, colon and rectum cancer, bladder cancer, melanoma of the skin, non-Hodgkin lymphoma, thyroid cancer, kidney and renal pelvis cancer, endometrial cancer, leukemia, and pancreatic cancer. The number of new cancer cases is projected to rise to 22 million within the next two decades.

The immune system has a key role in detecting and combating human cancer. The majority of transformed cells are quickly detected by immune sentinels and destroyed through the activation of antigen-specific T cells via clonally expressed T cell receptors (TCR). Accordingly, cancer can be considered an immunological disorder, a failure of immune system to mount the necessary anti-tumor response to durably suppress and eliminate the disease. In order to more effectively combat cancer, certain immunotherapy interventions developed over the last few decades have specifically focused on enhancing T cell immunity. These treatments have yielded only sporadic cases of disease remission and have not had substantial overall success. More recent therapies that use monoclonal antibodies targeting molecules that inhibit T cell activation, such as CTLA-4 or PDCD-1, have shown a more substantial anti-tumor effect; however, these treatments are also associated with substantial toxicity due to systemic immune activation.

Most recently, adoptive cellular immunotherapy strategies, which are based on the isolation, modification, expansion and reinfusion of T cells, have been explored and tested in early stage clinical trials. T cells have often been the effector cells of choice for cancer immunotherapy due to their selective recognition and powerful effector mechanisms. These treatments have shown mixed rates of success, but a small number of patients have experienced durable remissions, highlighting the as-yet unrealized potential for T cell-based immunotherapies.

Successful recognition of tumor cell associated antigens by cytolytic T cells initiates targeted tumor lysis and underpins any effective cancer immunotherapy approach. Tumor-infiltrating T cells (TILs) express TCRs specifically directed tumor-associated antigens; however, substantial numbers of TILs are limited to only a few human cancers. Engineered T cell receptors (TCRs) and chimeric antigen receptors (CARs) potentially increase the applicability of T cell-based immunotherapy to many cancers and other immune disorders.

In addition, state of the art engineered T cells are still regulated by a complex immunosuppressive tumor microenvironment that consists of cancer cells, inflammatory cells, stromal cells and cytokines. Among these components, cancer cells, inflammatory cells and suppressive cytokines regulate T cell phenotype and function. Collectively, the tumor microenvironment drives T cells to terminally differentiate into exhausted T cells.

T cell exhaustion is a state of T cell dysfunction in a chronic environment marked by increased expression of, or increased signaling by, inhibitory receptors; reduced effector cytokine production; and a decreased ability to persist and eliminate cancer. Exhausted T cells also show loss of function in a hierarchical manner: decreased IL-2 production and ex vivo killing capacity are lost at the early stage of exhaustion, TNF-α production is lost at the intermediate stage, and IFN-γ and GzmB production are lost at the advanced stage of exhaustion. Most T cells in the tumor microenvironment differentiate into exhausted T cells and lose the ability to eliminate cancer and are eventually cleared.

Program cell death 1 (PDCD-1) is expressed on T cells and mediates immunosuppression by binding to immunosuppressive factors, e.g., PD-L1 and PD-L2, present in the tumor microenvironment. The expression of PD-L1 and PD-L2 correlates with prognosis in some human malignancies. The PD-L1/PDCD-1 signaling pathway is one important regulatory pathway of T cell exhaustion. PD-L1 is abundantly expressed in cancer cells and stromal cells, and blockade of PD-L1/PDCD-1 using monoclonal antibodies enhances T cell anti-tumor function. PD-L2 also binds to PDCD-1 and negatively regulates T cell function.

BRIEF SUMMARY

The present disclosure generally relates, in part, to compositions comprising homing endonuclease variants and megaTALs with improved stability and activity that cleave a target site in the human PDCD-1 gene and methods of using the same.

In various embodiments, the present disclosure contemplates, in part, a polypeptide comprising an engineered homing endonuclease that has been engineered to improve stability and binding and cleavage of a target site.

In various embodiments, a polypeptide comprises an I-OnuI homing endonuclease (HE) variant.

In various embodiments, an I-OnuI homing endonuclease (HE) variant that cleaves a target site in the human programmed cell death 1 (PDCD-1) gene is provided, the I-OnuI HE variant comprising the following amino acid substitutions: I14T, L26G, R28S, R30L, N32R, K34R, S35G, S36T, V37A, G38R, S40H, E42R, G44S, Q46T, T48M, V68S, A70L, S72N, N75H, A76Y, K80V, T82Y, R83A, L138M, T143N, N153V, K156R, S159P, F168G, E178D, C180S, N184R, I186R, K189N, S190V, K191N, L192A, G193R, Q195R, S201E, T203S, K207R, Y223H, K225Y, K227G, F232R, D236Q, V238R, T240E, V261M, and G300R in an I-OnuI HE amino acid sequence set forth in any one of SEQ ID NOs: 1-5, or a biologically active fragment thereof. In preferred embodiments, the I-OnuI HE variant does not comprise an amino acid sequence set forth in any one of SEQ ID NOs: 15-20.

In some embodiments, the biologically active fragment lacks the 1, 2, 3, 4, 5, 6, 7, or 8 N-terminal amino acids compared to a corresponding wild type HE.

In additional embodiments, the biologically active fragment lacks the 4 N-terminal amino acids compared to a corresponding wild type HE.

In certain embodiments, the biologically active fragment lacks the 8 N-terminal amino acids compared to a corresponding wild type HE.

In particular embodiments, the biologically active fragment lacks the 1, 2, 3, 4, or 5 C-terminal amino acids compared to a corresponding wild type HE.

In particular embodiments, wherein the biologically active fragment lacks the C-terminal amino acid compared to a corresponding wild type HE.

In some embodiments, the biologically active fragment lacks the 2 C-terminal amino acids compared In particular embodiments, the I-OnuI HE variant comprises an amino acid sequence that is at least 95% identical to the amino acid sequence set forth in SEQ ID NO: 6, or a biologically active fragment thereof.

In particular embodiments, the I-OnuI HE variant comprises an amino acid sequence that is at least 96% identical to the amino acid sequence set forth in SEQ ID NO: 6, or a biologically active fragment thereof.

In particular embodiments, the I-OnuI HE variant comprises an amino acid sequence that is at least 97% identical to the amino acid sequence set forth in SEQ ID NO: 6, or a biologically active fragment thereof.

In particular embodiments, the I-OnuI HE variant comprises an amino acid sequence that is at least 98% identical to the amino acid sequence set forth in SEQ ID NO: 6, or a biologically active fragment thereof.

In particular embodiments, the I-OnuI HE variant comprises an amino acid sequence that is at least 98% or at least 99% identical to the amino acid sequence set forth in SEQ ID NO: 6, or a biologically active fragment thereof.

In particular embodiments, the I-OnuI HE variant comprises the amino acid sequence set forth in SEQ ID NO: 6, or a biologically active fragment thereof.

In certain embodiments, the I-OnuI HE variant binds the polynucleotide sequence set forth in SEQ ID NO: 8.

In further embodiments, the I-OnuI HE variant binds the polynucleotide sequence set forth in SEQ ID NO: 10.

In further embodiments, the polypeptide further comprises a DNA binding domain.

In some embodiments, the DNA binding domain is selected from the group consisting of: a TALE DNA binding domain and a zinc finger DNA binding domain.

In certain embodiments, the TALE DNA binding domain comprises about 9.5 TALE repeat units to about 15.5 TALE repeat units.

In additional embodiments, the TALE DNA binding domain binds a polynucleotide sequence in the PDCD-1 gene.

In particular embodiments, the TALE DNA binding domain binds the polynucleotide sequence set forth in SEQ ID NO: 9.

In additional embodiments, the polypeptide comprising an I-OnuI HE variant and a TALE DNA binding domain binds and cleaves the polynucleotide sequence set forth in SEQ ID NO: 10.

In further embodiments, the polypeptide further comprises a peptide linker and an end-processing enzyme or biologically active fragment thereof.

In particular embodiments, the polypeptide further comprises a viral self-cleaving 2A peptide and an end-processing enzyme or biologically active fragment thereof.

In additional embodiments, the end-processing enzyme or biologically active fragment thereof has 5'-3' exonuclease, 5'-3' alkaline exonuclease, 3'-5' exonuclease, 5' flap endonuclease, helicase or template-independent DNA polymerase activity.

In particular embodiments, the end-processing enzyme comprises Trex2 or a biologically active fragment thereof.

In certain embodiments, the polypeptide comprises an amino acid sequence that is at least 98% or at least 99% identical to the amino acid sequence set forth in SEQ ID NO: 7, or a biologically active fragment thereof.

In certain embodiments, the polypeptide comprises the amino acid sequence set forth in SEQ ID NO: 7, or a biologically active fragment thereof.

In further embodiments, the polypeptide cleaves the human PDCD-1 gene at a polynucleotide sequence set forth in SEQ ID NO: 10.

In various embodiments, the present disclosure contemplates, in part, a polynucleotide encoding a polypeptide contemplated herein.

In various embodiments, the present disclosure contemplates, in part, a polynucleotide encoding an I-OnuI HE variant contemplated herein.

In various embodiments, the polynucleotide is an mRNA.

In particular embodiments, an mRNA encoding a polypeptide contemplated herein comprises the polynucleotide sequence set for in SEQ ID NO: 11.

In particular embodiments, an mRNA encoding a polypeptide contemplated herein comprises the polynucleotide sequence set for in SEQ ID NO: 12.

In various embodiments, the polynucleotide is a cDNA.

In particular embodiments, an mRNA transcribed from the cDNA comprises the sequence set forth in SEQ ID NO: 11.

In particular embodiments, an mRNA transcribed from the cDNA comprises the sequence set forth in SEQ ID NO: 12.

In certain embodiments, a vector, comprising a polynucleotide encoding a polypeptide, an I-OnuI HE variant, an mRNA, or a cDNA contemplated is provided.

In particular embodiments, the vector is an expression vector, an episomal vector, or a viral vector.

In particular embodiments, the vector is an adeno-associated viral (AAV) vector.

In various embodiments, a cell comprising a polypeptide, an I-OnuI HE variant, a polynucleotide, an mRNA, a cDNA, or a vector contemplated herein is provided.

In particular embodiments, the cell is a hematopoietic cell.

In some embodiments, the cell is an immune effector cell.

In particular embodiments, the cell is a T cell.

In certain embodiments, the cell is a CD3+, CD4+, and/or CD8+ cell.

In particular embodiments, the cell is a cytotoxic T lymphocytes (CTLs), a tumor infiltrating lymphocytes (TILs), or a helper T cells.

In additional embodiments, the cell is a natural killer (NK) cell or natural killer T (NKT) cell.

In further embodiments, the source of the cell is peripheral blood mononuclear cells, bone marrow, lymph nodes tissue, cord blood, thymus issue, tissue from a site of infection, ascites, pleural effusion, spleen tissue, or tumors.

In various embodiments, the present disclosure contemplates, in part, a method of editing a human PDCD-1 gene in a cell comprising: introducing a polynucleotide encoding a polypeptide contemplated herein into the cell, wherein expression of the polypeptide creates a double strand break at a target site in a human PDCD-1 gene.

In some embodiments, the present disclosure contemplates, in part, a method of editing a human PDCD-1 gene in cell comprising: introducing a polynucleotide encoding a polypeptide contemplated herein into the cell, wherein expression of the polypeptide creates a double strand break at a target site in a human PDCD-1 gene, wherein the break is repaired by non-homologous end joining (NHEJ).

In various embodiments, the present disclosure contemplates, in part, a method of editing a human PDCD-1 gene in a cell comprising: introducing a polynucleotide encoding a polypeptide contemplated herein and a donor repair template into the cell, wherein expression of the polypeptide creates a double strand break at a target site in a human PDCD-1 gene and the donor repair template is incorporated into the human PDCD-1 gene by homology directed repair (HDR) at the site of the double-strand break (DSB).

In further embodiments, the cell is a hematopoietic cell.

In particular embodiments, the cell is a T cell.

In particular embodiments, the cell is a CD3+, CD4+, and/or CD8+ cell.

In certain embodiments, the cell is an immune effector cell.

In some embodiments, the cell is a cytotoxic T lymphocyte (CTL), a tumor infiltrating lymphocyte (TIL), or a helper T cell.

In particular embodiments, the cell is a natural killer (NK) cell or natural killer T (NKT) cell.

In certain embodiments, the source of the cell is peripheral blood mononuclear cells, bone marrow, lymph nodes tissue, cord blood, thymus issue, tissue from a site of infection, ascites, pleural effusion, spleen tissue, or tumors.

In particular embodiments, the polynucleotide encoding the polypeptide is an mRNA.

In additional embodiments, a polynucleotide encoding a 3'-5' exonuclease is introduced into the cell.

In some embodiments, a polynucleotide encoding Trex2 or a biologically active fragment thereof is introduced into the cell.

In further embodiments, the donor repair template encodes a PDCD-1 gene or portion thereof comprising one or more mutations compared to the wild type PDCD-1 gene.

In particular embodiments, the donor repair template encodes an engineered antigen receptor.

In further embodiments, the engineered antigen receptor is an αβTCR, a γδTCR, one or more components of a DARIC, a chimeric antigen receptor, or a zetakine.

In particular embodiments, the I-OnuI HE variant is more thermostable than an I-Onu HE variant that has not been refined to increase thermostability.

In particular embodiments, the I-OnuI HE variant is more thermostable than an I-Onu HE variant comprising an amino acid sequence set forth in any one of SEQ ID NOs: 15-20.

BRIEF DESCRIPTION OF THE SEQUENCE IDENTIFIERS

Figure 1A:
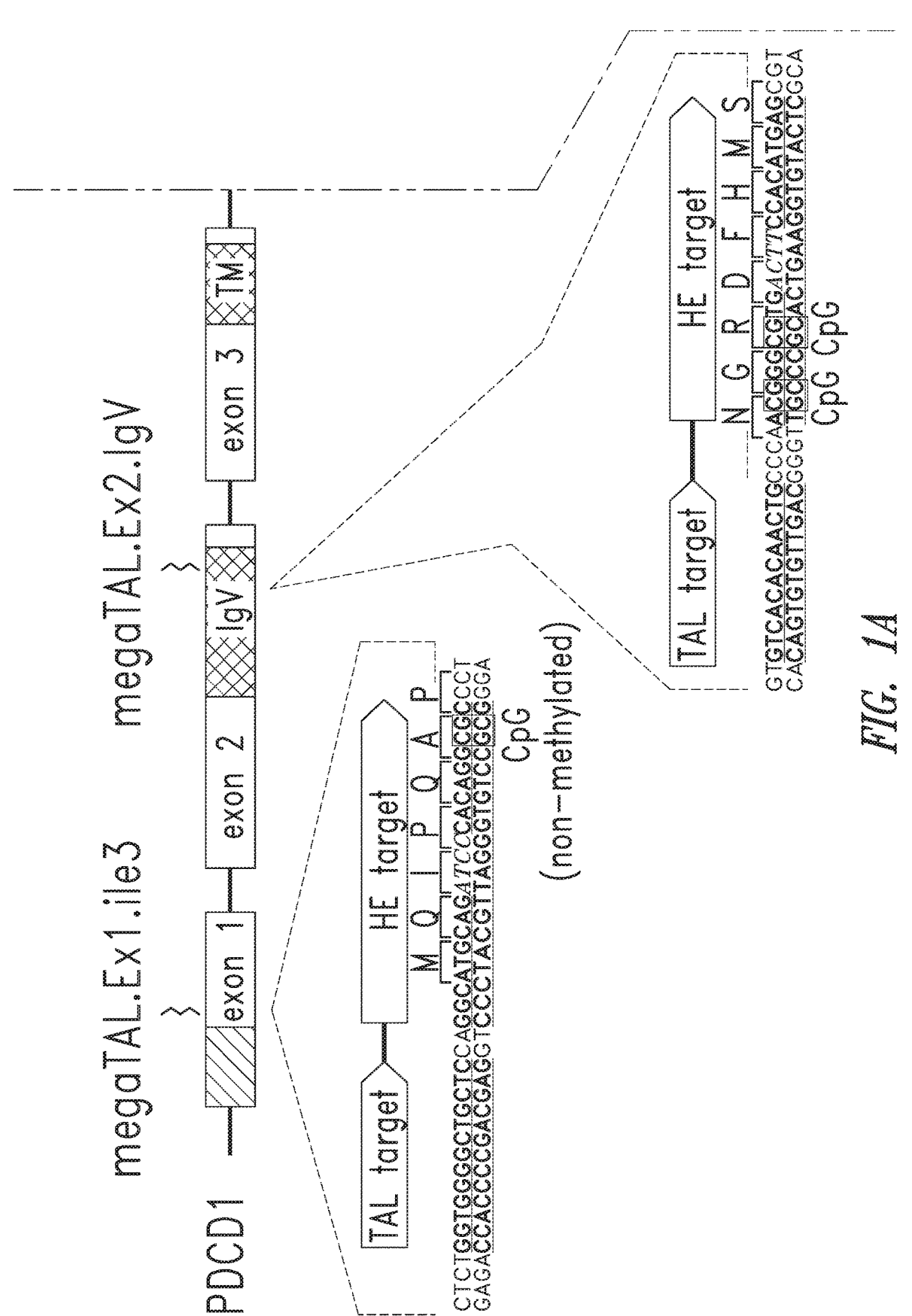
FIG. 1A show the PDCD-1 gene and the location of the target sites in exons 1 (SEQ ID NO: 57, 58 and 59) and 2 (SEQ ID NO: 60, 61 and 62).

SEQ ID NO: 1 is an amino acid sequence of a wild type I-OnuI LAGLIDADG homing endonuclease (LHE).

SEQ ID NO: 2 is an amino acid sequence of a wild type I-OnuI LHE.

SEQ ID NO: 3 is an amino acid sequence of a biologically active fragment of a wild-type I-OnuI LHE.

SEQ ID NO: 4 is an amino acid sequence of a biologically active fragment of a wild-type I-OnuI LHE.

SEQ ID NO: 5 is an amino acid sequence of a biologically active fragment of a wild-type I-OnuI LHE.

SEQ ID NO: 6 is an amino acid sequence of a stabilized I-OnuI LHE variant reprogrammed to bind and cleave a target site in the human PDCD-1 gene.

SEQ ID NO: 7 is an amino acid sequence of a megaTAL that binds and cleaves a target site in a human PDCD-1 gene.

SEQ ID NO: 8 is an I-OnuI LHE variant target site in a human PDCD-1 gene.

SEQ ID NO: 9 is a TALE DNA binding domain target site in a human PDCD-1 gene.

SEQ ID NO: 10 is a megaTAL target site in a human PDCD-1 gene.

SEQ ID NO: 11 is an mRNA encoding a stabilized PDCD-1 megaTAL.

SEQ ID NO: 12 is an mRNA encoding a stabilized PDCD-1 megaTAL.

SEQ ID NO: 13 is an mRNA encoding a murine Trex2 protein.

SEQ ID NO: 14 is an amino acid sequence encoding murine Trex2.

SEQ ID NO: 15-20 are amino acid sequences of mega-TALs that bind and cleave a target site in a human PDCD-1 gene.

SEQ ID NOs: 21-31 set forth the amino acid sequences of various linkers.

SEQ ID NOs: 32-56 set forth the amino acid sequences of protease cleavage sites and self-cleaving polypeptide cleavage sites.

In the foregoing sequences, X, if present, refers to any amino acid or the absence of an amino acid.

DETAILED DESCRIPTION

A. Overview

The present disclosure generally relates to, in part, improved genome editing compositions and methods of use thereof. Genome editing enzymes hold tremendous promise for treating diseases, disorders, and conditions with a genetic component. To date, genome editing enzymes engineered to bind and cleave target sites in the genome may not cleave with high efficiency. Without wishing to be bound to any particular theory, the inventors have discovered that genome editing enzyme activity unexpectedly increased when the enzymes were engineered to have greater thermostability. Moreover, the amino acid positions of the genome editing enzymes that can be altered to increase thermostability and activity against one target are conserved and can be used to increase thermostability of other genome editing enzymes designed to bind and cleave other target sites within a PDCD-1 gene.

In particular embodiments, genome edited immune effector cells contemplated herein are made more resistant to exhaustion by eliminating, decreasing, or damping PDCD-1 expression and/or signaling.

Genome editing compositions and methods contemplated in various embodiments comprise nuclease variants with enhanced stability and activity, designed to bind and cleave a target site in the human program cell death 1 (PDCD-1) gene. The nuclease variants contemplated in particular embodiments, can be used to introduce a double-strand break in a target polynucleotide sequence, which may be repaired by non-homologous end joining (NHEJ) in the absence of a polynucleotide template, e.g., a donor repair template, or by homology directed repair (HDR), i.e., homologous recombination, in the presence of a donor repair template. Nuclease variants contemplated in certain embodiments, can also be designed as nickases, which generate single-stranded DNA breaks that can be repaired using the cell's base-excision-repair (BER) machinery or homologous recombination in the presence of a donor repair template. NHEJ is an error-prone process that frequently results in the formation of small insertions and deletions that disrupt gene function. Homologous recombination requires homologous DNA as a template for repair and can be leveraged to create a limitless variety of modifications specified by the introduction of donor DNA containing the desired sequence at the target site, flanked on either side by sequences bearing homology to regions flanking the target site.

In one preferred embodiment, the genome editing compositions contemplated herein comprise a homing endonuclease variant or megaTAL that has been modified to increase stability and/or activity and that targets the human PDCD-1 gene.

In one preferred embodiment, the genome editing compositions contemplated herein comprise a homing endonuclease variant or megaTAL that has been modified to increase stability and/or activity and an end-processing enzyme, e.g., Trex2.

In various embodiments, a cell or population of cells comprising a homing endonuclease variant or megaTAL that has been modified to increase stability and/or activity are contemplated.

In various embodiments, a DNA break is generated in a target site of the PDCD-1 gene in a T cell, e.g., immune effector cell, and NHEJ of the ends of the cleaved genomic sequence may result in a cell with little or no PDCD-1 expression, and preferably a T cell that lacks or substantially lacks functional PDCD-1 expression and/or signaling, e.g., lacks the ability to increase T cell exhaustion. Without wishing to be bound by any particular theory, the improved nucleases contemplated herein result in a high editing rate of a PDCD-1 target site and renders T cells more resistant to immunosuppression and T cell exhaustion, and thus, T cells are more persistent and therapeutically efficacious.

In various other embodiments, a homing endonuclease variant or megaTAL that has been modified to increase stability and/or activity and a donor template, e.g., nucleic acid encoding an engineered antigen receptor, are provided. The PDCD-1 gene is repaired with the sequence of the template by homologous recombination at the DNA break-site. In particular embodiments, the repair template comprises a polynucleotide sequence that encodes a chimeric antigen receptor.

In preferred embodiments, the genome editing compositions and methods contemplated herein are used to edit the human PDCD-1 gene.

Accordingly, the methods and compositions contemplated herein represent a quantum improvement compared to existing adoptive cell therapies.

Techniques for recombinant (i.e., engineered) DNA, peptide and oligonucleotide synthesis, immunoassays, tissue culture, transformation (e.g., electroporation, lipofection), enzymatic reactions, purification and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., *Molecular Cloning: A Laboratory Manual,* 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid The Hybridization* (B. Hames & S. Higgins, Eds., 1985); Transcription and Translation (B. Hames & S. Higgins, Eds., 1984); *Animal Cell Culture* (R. Freshney, Ed., 1986); Perbal, *A Practical Guide to Molecular Cloning* (1984); Next-Generation Genome Sequencing (Janitz, 2008 Wiley-VCH); *PCR Protocols (Methods in Molecular Biology)* (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and C C Blackwell, eds., 1986); Roitt, *Essential Immunology,* 6th Edition, (Blackwell Scientific Publications, Oxford, 1988); *Current Protocols in Immunology* (Q. E. Coligan, A. M. Kruisbeek, D. H. Margulies, E. M. Shevach and W. Strober, eds., 1991); *Annual Review of Immunology*; as well as monographs in journals such as Advances in Immunology.

B. Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "of") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length $\pm15\%$, $\pm10\%$, 9%, $\pm8\%$, $\pm7\%$, $\pm6\%$, $\pm5\%$, $\pm4\%$, $\pm3\%$, $\pm2\%$, or $\pm1\%$ about a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured or modulated in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism. In one embodiment, cellular genomes are engineered, edited, or modified in vivo.

By "enhance" or "promote" or "increase" or "expand" or "potentiate" refers generally to the ability of a nuclease variant to produce, elicit, or cause a greater response (i.e., physiological response) compared to the response caused by either vehicle or control. A measurable response may include an increase in stability, catalytic activity, binding affinity, persistence, cytolytic activity, and/or an increase in proinflammatory cytokines, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response produced by vehicle or control.

By "decrease" or "lower" or "lessen" or "reduce" or "abate" or "ablate" or "inhibit" or "dampen" refers generally to the ability of a nuclease variant contemplated herein to produce, elicit, or cause a lesser response (i.e., physiological response) compared to the response caused by either vehicle or control. A measurable response may include a decrease in stability, off-target binding affinity, off-target cleavage specificity, T cell exhaustion, and the like. A "decrease" or "reduced" amount is typically a "statistically significant"

amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response (reference response) produced by vehicle, or control.

By "maintain," or "preserve," or "maintenance," or "no change," or "no substantial change," or "no substantial decrease" refers generally to the ability of a nuclease variant to produce, elicit, or cause a substantially similar or comparable physiological response (i.e., downstream effects) in as compared to the response caused by either vehicle or control. A comparable response is one that is not significantly different or measurable different from the reference response.

The terms "specific binding affinity" or "specifically binds" or "specifically bound" or "specific binding" or "specifically targets" as used herein, describe binding of one molecule to another, e.g., DNA binding domain of a polypeptide binding to DNA, at greater binding affinity than background binding. A binding domain "specifically binds" to a target site if it binds to or associates with a target site with an affinity or $K_a$ (i.e., an equilibrium association constant of a particular binding interaction with units of 1/M) of, for example, greater than or equal to about $10^5$ M$^{-1}$. In certain embodiments, a binding domain binds to a target site with a $K_a$ greater than or equal to about $10^6$ M$^{-1}$, $10^7$ M$^{-1}$, $10^8$ M$^{-1}$, $10^9$ M$^{-1}$, $10^{10}$ M$^{-1}$, $10^{11}$ M$^{-1}$, $10^{12}$ M$^{-1}$, or $10^{13}$ M$^{-1}$. "High affinity" binding domains refers to those binding domains with a $K_a$ of at least $10^7$ M$^{-1}$, at least $10^8$ M$^{-1}$, at least $10^9$ M$^{-1}$, at least $10^{10}$ M$^{-1}$, at least $10^{11}$ M$^{-1}$, at least $10^{12}$ M$^{-1}$, at least $10^{13}$ M$^{-1}$, or greater.

Alternatively, affinity may be defined as an equilibrium dissociation constant ($K_a$) of a particular binding interaction with units of M (e.g., $10^{-5}$ M to 1013 M, or less). Affinities of nuclease variants comprising one or more DNA binding domains for DNA target sites contemplated in particular embodiments can be readily determined using conventional techniques, e.g., yeast cell surface display, or by binding association, or displacement assays using labeled ligands.

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

The terms "selectively binds" or "selectively bound" or "selectively binding" or "selectively targets" and describe preferential binding of one molecule to a target molecule (on-target binding) in the presence of a plurality of off-target molecules. In particular embodiments, an HE or megaTAL selectively binds an on-target DNA binding site about 5, 10, 15, 20, 25, 50, 100, or 1000 times more frequently than the HE or megaTAL binds an off-target DNA target binding site.

"On-target" refers to a target site sequence.

"Off-target" refers to a sequence similar to but not identical to a target site sequence.

A "target site" or "target sequence" is a chromosomal or extrachromosomal nucleic acid sequence that defines a portion of a nucleic acid to which a binding molecule will bind and/or cleave, provided sufficient conditions for binding and/or cleavage exist. When referring to a polynucleotide sequence or SEQ ID NO. that references only one strand of a target site or target sequence, it would be understood that the target site or target sequence bound and/or cleaved by a nuclease variant is double-stranded and comprises the reference sequence and its complement. In a preferred embodiment, the target site is a sequence in a human PDCD-1 gene.

"Protein stability" refers to the net balance of forces, which determine whether a protein will be its native folded conformation or a denatured (unfolded or extended) state. Protein unfolding, either partial or complete, can result in loss of function along with degradation by the cellular machinery. Polypeptide stability can be measured in response to various conditions including but not limited to temperature, pressure, and osmolyte concentration.

"Thermostability" refers to the ability of a protein to properly fold or remain in its native folded conformation and resist denaturation or unfolding upon exposure to temperature fluctuations. At non-ideal temperatures a protein will either not be able to efficiently fold into an active confirmation or will have the propensity to unfold from its active confirmation. A protein with increased thermostability will fold properly and retain activity over an increased range of temperatures when compared to a protein that is less thermostable.

"TM$_{50}$" refers to the temperature at which 50% of an amount of protein is unfolded. In particular embodiments, the TM$_{50}$ is the temperature at which an amount of protein has 50% maximum activity. In particular embodiments, TM$_{50}$ is a specific value determined by fitting multiple data points to a Boltzmann sigmoidal curve. In one non-limiting example, the TM$_{50}$ of a protein is measured in a yeast surface display activity assay by expressing the protein on the yeast surface at ~25° C., aliquoting the yeast into multiple wells and exposing to a range of higher temperatures, cooling the yeast, and then measuring cleavage activity of the enzyme. As the temperature increases, more of the proteins lose their active confirmation, and therefore fewer protein expressing cells display sufficient activity to measure cleavage with flow cytometry. The temperature at which 50% of yeast display population is active as compared to the non-heat shocked population is the TM$_{50}$.

Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair (HDR) mechanisms. This process requires nucleotide sequence homology, uses a "donor" molecule as a template to repair a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part of or all of the sequence of the donor polynucleotide is incorporated into the target polynucleotide.

"NHEJ" or "non-homologous end joining" refers to the resolution of a double-strand break in the absence of a donor repair template or homologous sequence. NHEJ can result in insertions and deletions at the site of the break. NHEJ is mediated by several sub-pathways, each of which has distinct mutational consequences. The classical NHEJ pathway (cNHEJ) requires the KU/DNA-PKcs/Lig4/XRCC4 complex, ligates ends back together with minimal processing and often leads to precise repair of the break. Alternative NHEJ pathways (altNHEJ) also are active in resolving dsDNA breaks, but these pathways are considerably more mutagenic and often result in imprecise repair of the break marked by insertions and deletions. While not wishing to be bound to any particular theory, it is contemplated that modification of dsDNA breaks by end-processing enzymes, such as, for example, exonucleases, e.g., Trex2, may increase the likelihood of imprecise repair.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, polypeptides and nuclease variants, e.g., homing endonuclease variants, megaTALs, etc. contemplated herein are used for targeted double-stranded DNA cleavage. Endonuclease cleavage recognition sites may be on either DNA strand.

An "exogenous" molecule is a molecule that is not normally present in a cell, but that is introduced into a cell by one or more genetic, biochemical or other methods. Exemplary exogenous molecules include, but are not limited to small organic molecules, protein, nucleic acid, carbohydrate, lipid, glycoprotein, lipoprotein, polysaccharide, any modified derivative of the above molecules, or any complex comprising one or more of the above molecules. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, biopolymer nanoparticle, calcium phosphate co-precipitation, DEAE-dextran-mediated transfer and viral vector-mediated transfer.

An "endogenous" molecule is one that is normally present in a particular cell at a particular developmental stage under particular environmental conditions. Additional endogenous molecules can include proteins.

A "gene," refers to a DNA region encoding a gene product, as well as all DNA regions which regulate the production of the gene product, whether or not such regulatory sequences are adjacent to coding and/or transcribed sequences. A gene includes, but is not limited to, promoter sequences, enhancers, silencers, insulators, boundary elements, terminators, polyadenylation sequences, post-transcription response elements, translational regulatory sequences such as ribosome binding sites and internal ribosome entry sites, replication origins, matrix attachment sites, and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

As used herein, the term "genetically engineered" or "genetically modified" refers to the chromosomal or extra-chromosomal addition of extra genetic material in the form of DNA or RNA to the total genetic material in a cell. Genetic modifications may be targeted or non-targeted to a particular site in a cell's genome. In one embodiment, genetic modification is site specific. In one embodiment, genetic modification is not site specific.

As used herein, the term "genome editing" refers to the substitution, deletion, and/or introduction of genetic material at a target site in the cell's genome, which restores, corrects, disrupts, and/or modifies expression and/or function of a gene or gene product. Genome editing contemplated in particular embodiments comprises introducing one or more nuclease variants into a cell to generate DNA lesions at or proximal to a target site in the cell's genome, optionally in the presence of a donor repair template.

As used herein, the term "gene therapy" refers to the introduction of extra genetic material into the total genetic material in a cell that restores, corrects, or modifies expression of a gene or gene product, or for the purpose of expressing a therapeutic polypeptide. In particular embodiments, introduction of genetic material into the cell's genome by genome editing that restores, corrects, disrupts, or modifies expression of a gene or gene product, or for the purpose of expressing a therapeutic polypeptide is considered gene therapy.

Additional definitions are set forth throughout this disclosure.

C. Nuclease Variants

Nuclease variants contemplated in particular embodiments herein have been modified to increase thermostability and enzymatic activity. The nuclease variants are suitable for genome editing a target site in the PDCD-1 gene and comprise one or more DNA binding domains and one or more DNA cleavage domains (e.g., one or more endonuclease and/or exonuclease domains), and optionally, one or more linkers contemplated herein. The terms "reprogrammed nuclease," "engineered nuclease," or "nuclease variant" are used interchangeably and refer to a nuclease comprising one or more DNA binding domains and one or more DNA cleavage domains, wherein the nuclease has been designed and/or modified from a parental or naturally occurring nuclease, to bind and cleave a double-stranded DNA target sequence in a PDCD-1 gene.

In particular embodiments, a nuclease variant binds and cleaves a target sequence in exon 1 of a PDCD-1 gene, preferably at SEQ ID NO: 8 in exon 1 of a PDCD-1 gene, and more preferably at the sequence "ATCC" in SEQ ID NO: 8 in exon 1 of a PDCD-1 gene.

The nuclease variant may be designed and/or modified from a naturally occurring nuclease or from a previous nuclease variant. In preferred embodiments, an I-OnuI HE variant comprises increased thermostability and/or enzymatic activity compared to a parent I-OnuI HE variant. Nuclease variants contemplated in particular embodiments may further comprise one or more additional functional domains, e.g., an end-processing enzymatic domain of an end-processing enzyme that exhibits 5'-3' exonuclease, 5'-3' alkaline exonuclease, 3'-5'exonuclease (e.g., Trex2), 5' flap endonuclease, helicase, template-dependent DNA polymerases or template-independent DNA polymerase activity.

Illustrative examples of nuclease variants that bind and cleave a target sequence in the PDCD-1 gene include but are not limited to homing endonuclease (meganuclease) variants and megaTALs.

1. Homing Endonuclease (Meganuclease) Variants

In various embodiments, a homing endonuclease or meganuclease is engineered to increase its thermostability and enzymatic activity and to introduce a double-strand break (DSB) in a target site in a PDCD-1 gene. In particular embodiments, a homing endonuclease variant introduces a double strand break in exon 1 of a PDCD-1 gene, preferably at SEQ ID NO: 8 in exon 1 of a PDCD-1 gene, and more preferably at the sequence "ATCC" in SEQ ID NO: 8 in exon 1 of a PDCD-1 gene.

"Homing endonuclease" and "meganuclease" are used interchangeably and refer to naturally-occurring homing endonucleases that recognize 12-45 base-pair cleavage sites and are commonly grouped into five families based on sequence and structure motifs: LAGLIDADG, GIY-YIG, HNH, His-Cys box, and PD-(D/E)XK.

A "reference homing endonuclease" or "reference meganuclease" refers to a wild type homing endonuclease or a homing endonuclease found in nature. In one embodiment, a "reference homing endonuclease" refers to a wild type homing endonuclease that has been modified to increase basal activity.

An "engineered homing endonuclease," "reprogrammed homing endonuclease," "homing endonuclease variant," "engineered meganuclease," "reprogrammed meganuclease," or "meganuclease variant" refers to a homing endonuclease comprising one or more DNA binding domains and one or more DNA cleavage domains, wherein the homing endonuclease has been designed and/or modified from a parental or naturally occurring homing endonuclease, to bind and cleave a DNA target sequence in a PDCD-1 gene and has further been modified to have increased thermostability and enzymatic activity. The homing endonuclease variant may be designed and/or modified from a naturally occurring homing endonuclease or from another homing endonuclease variant. Homing endonuclease variants contemplated in particular embodiments may further comprise one or more additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase, template dependent DNA polymerase or template-independent DNA polymerase activity.

Homing endonuclease (HE) variants do not exist in nature and can be obtained by recombinant DNA technology or by random mutagenesis. HE variants may be obtained by making one or more amino acid alterations, e.g., mutating, substituting, adding, or deleting one or more amino acids, in a naturally occurring HE or HE variant. In particular embodiments, a HE variant comprises one or more amino acid alterations to the DNA recognition interface.

HE variants contemplated in particular embodiments may further comprise one or more linkers and/or additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase or template-independent DNA polymerase activity. In particular embodiments, HE variants are introduced into a T cell with an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase or template-independent DNA polymerase activity. The HE variant and 3' processing enzyme may be introduced separately, e.g., in different vectors or separate mRNAs, or together, e.g., as a fusion protein, or in a polycistronic construct separated by a viral self-cleaving peptide or an IRES element.

A "DNA recognition interface" refers to the HE amino acid residues that interact with nucleic acid target bases as well as those residues that are adjacent. For each HE, the DNA recognition interface comprises an extensive network of side chain-to-side chain and side chain-to-DNA contacts, most of which is necessarily unique to recognize a particular nucleic acid target sequence. Thus, the amino acid sequence of the DNA recognition interface corresponding to a particular nucleic acid sequence varies significantly and is a feature of any natural or HE variant. By way of non-limiting example, a HE variant contemplated in particular embodiments may be derived by constructing libraries of HE variants in which one or more amino acid residues localized in the DNA recognition interface of the natural HE (or a previously generated HE variant) are varied. The libraries may be screened for target cleavage activity against each predicted PDCD-1 target site using cleavage assays (see e.g., Jarjour et al., 2009. *Nuc. Acids Res.* 37(20): 6871-6880).

LAGLIDADG homing endonucleases (LHE) are the most well studied family of homing endonucleases, are primarily encoded in archaea and in organellar DNA in green algae and fungi, and display the highest overall DNA recognition specificity.

In one embodiment, the reprogrammed LHE or LHE variant is an I-OnuI variant. See e.g., SEQ ID NO: 6.

In one embodiment, reprogrammed I-OnuI LHEs or I-OnuI variants targeting the PDCD-1 gene were generated from a natural I-OnuI or biologically active fragment thereof (SEQ ID NOs: 1-5). In a preferred embodiment, reprogrammed I-OnuI LHEs or I-OnuI variants targeting the human PDCD-1 gene were generated from an existing I-OnuI variant. In one embodiment, reprogrammed I-OnuI LHEs were generated against a human PDCD-1 gene target site set forth in SEQ ID NO: 8.

In certain embodiments, the I-OnuI HE variant cleaves a PDCD-1 exon 1 target site and comprises at least 5, at least 15, preferably at least 25, more preferably at least 35, or even more preferably at least 40 or more of the following amino acid substitutions: I14T, L26G, R28S, R30L, N32R, K34R, S35G, S36T, V37A, G38R, S40H, E42R, G44S, Q46T, T48M, V68S, A70L, S72N, N75H, A76Y, K80V, T82Y, R83A, L138M, T143N, N153V, K156R, S159P, F168G, E178D, C180S, N184R, I186R, K189N, S190V, K191N, L192A, G193R, Q195R, S201E, T203S, K207R, Y223H, K225Y, K227G, F232R, D236Q, V238R, T240E, V261M, and G300R of I-OnuI (SEQ ID NOs: 1-5) or an I-OnuI variant as set forth in any one of SEQ ID NOs: 6-10, biologically active fragments thereof, and/or further variants thereof.

In some embodiments, the I-OnuI HE variant cleaves a PDCD-1 exon 1 target site and comprises the following amino acid substitutions: I14T, L26G, R28S, R30L, N32R, K34R, S35G, S36T, V37A, G38R, S40H, E42R, G44S, Q46T, T48M, V68S, A70L, S72N, N75H, A76Y, K80V, T82Y, R83A, L138M, T143N, N153V, K156R, S159P, F168G, E178D, C180S, N184R, I186R, K189N, S190V, K191N, L192A, G193R, Q195R, S201E, T203S, K207R, Y223H, K225Y, K227G, F232R, D236Q, V238R, T240E, V261M, and G300R of I-OnuI (SEQ ID NOs: 1-5) or a biologically active fragments thereof.

In particular embodiments, an I-OnuI LHE variant that binds and cleaves a human PDCD-1 gene comprises an amino acid sequence that is at least 98% or at least 99% identical to the amino acid sequence set forth in any one of SEQ ID NO: 6 or a biologically active fragment thereof.

In particular embodiments, an I-OnuI LHE variant comprises an amino acid sequence set forth in SEQ ID NO: 6, or a biologically active fragment thereof.

2. MEGATALs

In various embodiments, a megaTAL comprising a homing endonuclease variant is engineered to increase its thermostability and enzymatic activity and to introduce a double-strand break (DSB) in a target site in a PDCD-1 gene. In particular embodiments, a megaTAL introduces a double strand break in exon 1 of a PDCD-1 gene, preferably at SEQ ID NO: 10 in exon 1 of a PDCD-1 gene, and more preferably at the sequence "ATCC" in SEQ ID NO: 10 in exon 1 of a PDCD-1 gene.

A "megaTAL" refers to a polypeptide comprising a TALE DNA binding domain and a homing endonuclease variant that binds and cleaves a DNA target sequence in a PDCD-1 gene, and optionally comprises one or more linkers and/or additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase or template-independent DNA polymerase activity.

In particular embodiments, a megaTAL can be introduced into a cell along with an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase, or template-independent DNA polymerase activity. The megaTAL and 3' processing enzyme may be introduced separately, e.g., in different vectors or separate mRNAs, or together, e.g., as a fusion protein, or in a polycistronic construct separated by a viral self-cleaving peptide or an IRES element.

A "TALE DNA binding domain" is the DNA binding portion of transcription activator-like effectors (TALE or TAL-effectors), which mimics plant transcriptional activators to manipulate the plant transcriptome (see e.g., Kay et al., 2007. Science 318:648-651). TALE DNA binding domains contemplated in particular embodiments are engineered de novo or from naturally occurring TALEs, e.g., AvrBs3 from *Xanthomonas campestris* pv. *vesicatoria*, *Xanthomonas gardneri*, *Xanthomonas translucens*, *Xanthomonas axonopodis*, *Xanthomonas perforans*, *Xanthomonas alfalfa*, *Xanthomonas citri*, *Xanthomonas euvesicatoria*, and *Xanthomonas oryzae* and brg11 and hpx17 from *Ralstonia solanacearum*. Illustrative examples of TALE proteins for deriving and designing DNA binding domains are disclosed in U.S. Pat. No. 9,017,967, and references cited therein, all of which are incorporated herein by reference in their entireties.

In particular embodiments, a megaTAL comprises a TALE DNA binding domain comprising one or more repeat units that are involved in binding of the TALE DNA binding domain to its corresponding target DNA sequence. A single "repeat unit" (also referred to as a "repeat") is typically 33-35 amino acids in length. Each TALE DNA binding domain repeat unit includes 1 or 2 DNA-binding residues making up the Repeat Variable Di-Residue (RVD), typically at positions 12 and/or 13 of the repeat. The natural (canonical) code for DNA recognition of these TALE DNA binding domains has been determined such that an HD sequence at positions 12 and 13 leads to a binding to cytosine (C), NG binds to T, NI to A, NN binds to G or A, and NG binds to T. In certain embodiments, non-canonical (atypical) RVDs are contemplated.

Illustrative examples of non-canonical RVDs suitable for use in particular megaTALs contemplated in particular embodiments include, but are not limited to HH, KH, NH, NK, NQ, RH, RN, SS, NN, SN, KN for recognition of guanine (G); NI, KI, RI, HI, SI for recognition of adenine (A); NG, HG, KG, RG for recognition of thymine (T); RD, SD, HD, ND, KD, YG for recognition of cytosine (C); NV, HN for recognition of A or G; and H*, HA, KA, N*, NA, NC, NS, RA, S*for recognition of A or T or G or C, wherein (*) means that the amino acid at position 13 is absent. Additional illustrative examples of RVDs suitable for use in particular megaTALs contemplated in particular embodiments further include those disclosed in U.S. Pat. No. 8,614,092, which is incorporated herein by reference in its entirety.

In particular embodiments, a megaTAL contemplated herein comprises a TALE DNA binding domain comprising 3 to 30 repeat units. In certain embodiments, a megaTAL comprises 3, 4, 5, 6, 7, 8, 9, 10, 11, 12, 13, 14, 15, 16, 17, 18, 19, 20, 21, 22, 23, 24, 25, 26, 27, 28, 29, or 30 TALE DNA binding domain repeat units. In a preferred embodiment, a megaTAL contemplated herein comprises a TALE DNA binding domain comprising 5-15 repeat units, more preferably 7-15 repeat units, more preferably 9-15 repeat units, and more preferably 9, 10, 11, 12, 13, 14, or 15 repeat units.

In particular embodiments, a megaTAL contemplated herein comprises a TALE DNA binding domain comprising 3 to 30 repeat units and an additional single truncated TALE repeat unit comprising 20 amino acids located at the C-terminus of a set of TALE repeat units, i.e., an additional C-terminal half-TALE DNA binding domain repeat unit (amino acids −20 to −1 of the C-cap disclosed elsewhere herein, infra). Thus, in particular embodiments, a megaTAL contemplated herein comprises a TALE DNA binding domain comprising 3.5 to 30.5 repeat units. In certain embodiments, a megaTAL comprises 3.5, 4.5, 5.5, 6.5, 7.5, 8.5, 9.5, 10.5, 11.5, 12.5, 13.5, 14.5, 15.5, 16.5, 17.5, 18.5, 19.5, 20.5, 21.5, 22.5, 23.5, 24.5, 25.5, 26.5, 27.5, 28.5, 29.5, or 30.5 TALE DNA binding domain repeat units. In a preferred embodiment, a megaTAL contemplated herein comprises a TALE DNA binding domain comprising 5.5-15.5 repeat units, more preferably 7.5-15.5 repeat units, more preferably 9.5-15.5 repeat units, and more preferably 9.5, 10.5, 11.5, 12.5, 13.5, 14.5, or 15.5 repeat units.

In particular embodiments, a megaTAL comprises a TAL effector architecture comprising an "N-terminal domain (NTD)" polypeptide, one or more TALE repeat domains/ units, a "C-terminal domain (CTD)" polypeptide, and a homing endonuclease variant. In some embodiments, the NTD, TALE repeats, and/or CTD domains are from the same species. In other embodiments, one or more of the NTD, TALE repeats, and/or CTD domains are from different species.

As used herein, the term "N-terminal domain (NTD)" polypeptide refers to the sequence that flanks the N-terminal portion or fragment of a naturally occurring TALE DNA binding domain. The NTD sequence, if present, may be of any length as long as the TALE DNA binding domain repeat units retain the ability to bind DNA. In particular embodiments, the NTD polypeptide comprises at least 120 to at least 140 or more amino acids N-terminal to the TALE DNA binding domain (0 is amino acid 1 of the most N-terminal repeat unit). In particular embodiments, the NTD polypeptide comprises at least about 120, 121, 122, 123, 124, 125, 126, 127, 128, 129, 130, 131, 132, 133, 134, 135, 136, 137, 138, 139, or at least 140 amino acids N-terminal to the TALE DNA binding domain. In one embodiment, a megaTAL contemplated herein comprises an NTD polypeptide of at least about amino acids +1 to +122 to at least about +1 to +137 of a *Xanthomonas* TALE protein (0 is amino acid 1 of the most N-terminal repeat unit). In particular embodiments, the NTD polypeptide comprises at least about 122, 123, 124, 125, 126, 127, 128, 129, 130, 131, 132, 133, 134, 135, 136, or 137 amino acids N-terminal to the TALE DNA binding domain of a *Xanthomonas* TALE protein. In one embodiment, a megaTAL contemplated herein comprises an NTD polypeptide of at least amino acids +1 to +121 of a *Ralstonia* TALE protein (0 is amino acid 1 of the most N-terminal repeat unit). In particular embodiments, the NTD polypeptide comprises at least about 121, 122, 123, 124, 125, 126, 127, 128, 129, 130, 131, 132, 133, 134, 135, 136, or 137 amino acids N-terminal to the TALE DNA binding domain of a *Ralstonia* TALE protein.

As used herein, the term "C-terminal domain (CTD)" polypeptide refers to the sequence that flanks the C-terminal portion or fragment of a naturally occurring TALE DNA binding domain. The CTD sequence, if present, may be of any length as long as the TALE DNA binding domain repeat units retain the ability to bind DNA. In particular embodiments, the CTD polypeptide comprises at least 20 to at least 85 or more amino acids C-terminal to the last full repeat of the TALE DNA binding domain (the first 20 amino acids are the half-repeat unit C-terminal to the last C-terminal full repeat unit). In particular embodiments, the CTD polypeptide comprises at least about 20, 21, 22, 23, 24, 25, 26, 27, 28, 29, 30, 31, 32, 33, 34, 35, 36, 37, 38, 39, 40, 41, 42, 443, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or at least 85 amino acids C-terminal to the last full repeat of the TALE DNA binding domain. In one embodiment, a megaTAL contemplated herein comprises a CTD polypeptide of at least about amino acids −20 to −1 of a *Xanthomonas* TALE protein (−20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a *Xanthomonas* TALE protein. In one embodiment, a megaTAL contemplated herein comprises a CTD polypeptide of at least about amino acids −20 to −1 of a *Ralstonia* TALE protein (−20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a *Ralstonia* TALE protein.

In particular embodiments, a megaTAL contemplated herein, comprises a fusion polypeptide comprising a TALE DNA binding domain engineered to bind a target sequence, a homing endonuclease reprogrammed to bind and cleave a target sequence and engineered to increase enzyme stability and/or activity, and optionally an NTD and/or CTD polypeptide, optionally joined to each other with one or more linker polypeptides contemplated elsewhere herein. Without wishing to be bound by any particular theory, it is contemplated that a megaTAL comprising TALE DNA binding domain, and optionally an NTD and/or CTD polypeptide is fused to a linker polypeptide which is further fused to a homing endonuclease variant. Thus, the TALE DNA binding domain binds a DNA target sequence that is within about 1, 2, 3, 4, 5, 6, 7, 8, 9, 10, 11, 12, 13, 14, or 15 nucleotides away from the target sequence bound by the DNA binding domain of the homing endonuclease variant. In this way, the mega-TALs contemplated herein, increase the specificity and efficiency of genome editing.

In one embodiment, a megaTAL comprises a homing endonuclease variant and a TALE DNA binding domain that binds a nucleotide sequence that is within about 2, 3, 4, 5, or 6 nucleotides, preferably, 2 or 4 nucleotides upstream of the binding site of the reprogrammed homing endonuclease.

In one embodiment, a megaTAL comprises a homing endonuclease variant engineered to improve thermostability and/or enzymatic activity and a TALE DNA binding domain that binds the nucleotide sequence set forth in SEQ ID NO: 9, which is 2 nucleotides upstream of the nucleotide sequence bound and cleaved by the homing endonuclease variant (SEQ ID NO: 8). In preferred embodiments, the megaTAL target sequence is SEQ ID NO: 10.

In particular embodiments, a megaTAL contemplated herein, comprises one or more TALE DNA binding repeat units and an I-OnuI HE variant comprising increased thermostability and/or enzymatic activity compared to a parent I-OnuI HE variant.

In particular embodiments, a megaTAL contemplated herein, comprises an NTD, one or more TALE DNA binding repeat units, a CTD, and an I-OnuI HE variant comprising increased thermostability and/or enzymatic activity compared to a parent I-OnuI HE variant.

In particular embodiments, a megaTAL contemplated herein, comprises an NTD, about 9.5 to about 15.5 TALE DNA binding repeat units, and an I-OnuI HE variant comprising increased thermostability and/or enzymatic activity compared to a parent I-OnuI HE variant.

In particular embodiments, a megaTAL contemplated herein, comprises an NTD of about 122 amino acids to 137 amino acids, about 9.5, about 10.5, about 11.5, about 12.5, about 13.5, about 14.5, or about 15.5 binding repeat units, a CTD of about 20 amino acids to about 85 amino acids, and an I-OnuI HE variant comprising increased thermostability and/or enzymatic activity compared to a parent I-OnuI HE variant. In particular embodiments, any one of, two of, or all of the NTD, DNA binding domain, and CTD can be designed from the same species or different species, in any suitable combination.

In particular embodiments, a megaTAL contemplated herein, comprises the amino acid sequence set forth in SEQ ID NO: 7.

In certain embodiments, a megaTAL contemplated herein, is encoded by an mRNA sequence set forth in any one of SEQ ID NOs: 11 or 12.

In certain embodiments, a megaTAL comprises a TALE DNA binding domain and an I-OnuI LHE variant that binds and cleaves the nucleotide sequence set forth in SEQ ID NO: 8 or 10. In particular embodiments, the megaTAL that binds and cleaves the nucleotide sequence set forth in SEQ ID NO: 8 or 10 comprises the amino acid sequence set forth in SEQ ID NO: 7.

3. End-Processing Enzymes

Genome editing compositions and methods contemplated in particular embodiments comprise editing cellular genomes using an I-OnuI HE variant comprising increased thermostability and/or enzymatic activity compared to a parent I-OnuI HE variant and one or more copies of an end-processing enzyme. In particular embodiments, a single polynucleotide encodes a homing endonuclease variant and an end-processing enzyme, separated by a linker, a self-cleaving peptide sequence, e.g., 2A sequence, or by an IRES sequence. In particular embodiments, genome editing compositions comprise a polynucleotide encoding a nuclease variant and a separate polynucleotide encoding an end-processing enzyme. In particular embodiments, genome editing compositions comprise a polynucleotide encoding a homing endonuclease variant end-processing enzyme single polypeptide fusion in addition to a tandem copy of the end-processing enzyme separated by a self-cleaving peptide.

The term "end-processing enzyme" refers to an enzyme that modifies the exposed ends of a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An end-processing enzyme may modify exposed polynucleotide chain ends by adding one or more nucleotides, removing one or more nucleotides, removing or modifying a phosphate group and/or removing or modifying a hydroxyl group. An end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents.

In particular embodiments, genome editing compositions and methods contemplated in particular embodiments comprise editing cellular genomes using and an I-OnuI HE variant comprising increased thermostability and/or enzymatic activity compared to a parent I-OnuI HE variant or megaTAL and a DNA end-processing enzyme.

The term "DNA end-processing enzyme" refers to an enzyme that modifies the exposed ends of DNA. A DNA end-processing enzyme may modify blunt ends or staggered ends (ends with 5' or 3' overhangs). A DNA end-processing enzyme may modify single stranded or double stranded DNA. A DNA end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents. DNA end-processing enzyme may modify exposed DNA ends by adding one or more nucleotides, removing one or more nucleotides, removing or modifying a phosphate group and/or removing or modifying a hydroxyl group.

Illustrative examples of DNA end-processing enzymes suitable for use in particular embodiments contemplated herein include but are not limited to: 5'-3' exonucleases, 5'-3' alkaline exonucleases, 3'-5' exonucleases, 5' flap endonucleases, helicases, phosphatases, hydrolases and template-independent DNA polymerases.

Additional illustrative examples of DNA end-processing enzymes suitable for use in particular embodiments contemplated herein include, but are not limited to, Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgs1, Sae2, CUP, Pol mu, Pol lambda, MUS81, EME1, EME2, SLX1, SLX4 and UL-12.

In particular embodiments, genome editing compositions and methods for editing cellular genomes contemplated herein comprise polypeptides comprising an I-OnuI HE variant or megaTAL and an exonuclease. The term "exonuclease" refers to enzymes that cleave phosphodiester bonds at the end of a polynucleotide chain via a hydrolyzing reaction that breaks phosphodiester bonds at either the 3' or 5' end.

Illustrative examples of exonucleases suitable for use in particular embodiments contemplated herein include, but are not limited to: hExoI, Yeast ExoI, E. coli ExoI, hTREX2, mouse TREX2, rat TREX2, hTREX1, mouse TREX1, rat TREX1, and Rat TREX1.

In particular embodiments, the DNA end-processing enzyme is a 3' to 5' exonuclease, preferably Trex 1 or Trex2, more preferably Trex2, and even more preferably human or mouse Trex2.

D. Target Sites

In various embodiments, I-OnuI HE variants and megaTALs bind to and cleave a target sequence in a program death receptor 1 (PDCD-1) gene.

In a preferred embodiment, a homing endonuclease variant or megaTAL cleaves double-stranded DNA and introduces a DSB into the polynucleotide sequence set forth in SEQ ID NO: 8 or 10.

In preferred embodiments, a homing endonuclease variant or megaTAL introduces a DSB in exon 1 of a PDCD-1 gene, preferably at SEQ ID NO: 8 (or SEQ ID NO: 10) in exon 1 of a PDCD-1 gene, and more preferably at the sequence "ATCC" in SEQ ID NO: 8 (or SEQ ID NO: 10) in exon 1 of a PDCD-1 gene.

In a preferred embodiment, the PDCD-1 gene is a human PDCD-1 gene.

E. Donor Repair Templates

Nuclease variants may be used to introduce a DSB in a target sequence; the DSB may be repaired through homology directed repair (HDR) mechanisms in the presence of one or more donor repair templates.

In particular embodiments, the donor repair template is used to insert a sequence into the genome. In particular preferred embodiments, the donor repair template is used to repair or modify a sequence in the genome.

In various embodiments, the donor repair template comprises one or more polynucleotides encoding an engineered antigen receptor.

In various embodiments, a donor repair template is introduced into a hematopoietic cell, e.g., a T cell, by transducing the cell with an adeno-associated virus (AAV), retrovirus, e.g., lentivirus, IDLV, etc., herpes simplex virus, adenovirus, or vaccinia virus vector comprising the donor repair template.

In particular embodiments, the donor repair template comprises one or more homology arms that flank the DSB site.

As used herein, the term "homology arms" refers to a nucleic acid sequence in a donor repair template that is identical, or nearly identical, to DNA sequence flanking the DNA break introduced by the nuclease at a target site. In one embodiment, the donor repair template comprises a 5' homology arm that comprises a nucleic acid sequence that is identical or nearly identical to the DNA sequence 5' of the DNA break site. In one embodiment, the donor repair template comprises a 3' homology arm that comprises a nucleic acid sequence that is identical or nearly identical to the DNA sequence 3' of the DNA break site. In a preferred embodiment, the donor repair template comprises a 5' homology arm and a 3' homology arm. The donor repair template may comprise homology to the genome sequence immediately adjacent to the DSB site, or homology to the genomic sequence within any number of base pairs from the DSB site. In one embodiment, the donor repair template comprises a nucleic acid sequence that is homologous to a genomic sequence about 5 bp, about 10 bp, about 25 bp, about 50 bp, about 100 bp, about 250 bp, about 500 bp, about 1000 bp, about 2500 bp, about 5000 bp, about 10000 bp or more, including any intervening length of homologous sequence.

Illustrative examples of suitable lengths of homology arms contemplated in particular embodiments, may be independently selected, and include but are not limited to: about 100 bp, about 200 bp, about 300 bp, about 400 bp, about 500 bp, about 600 bp, about 700 bp, about 800 bp, about 900 bp, about 1000 bp, about 1100 bp, about 1200 bp, about 1300 bp, about 1400 bp, about 1500 bp, about 1600 bp, about 1700 bp, about 1800 bp, about 1900 bp, about 2000 bp, about 2100 bp, about 2200 bp, about 2300 bp, about 2400 bp, about 2500 bp, about 2600 bp, about 2700 bp, about 2800 bp, about 2900 bp, or about 3000 bp, or longer homology arms, including all intervening lengths of homology arms.

Additional illustrative examples of suitable homology arm lengths include, but are not limited to: about 100 bp to about 3000 bp, about 200 bp to about 3000 bp, about 300 bp to about 3000 bp, about 400 bp to about 3000 bp, about 500 bp to about 3000 bp, about 500 bp to about 2500 bp, about 500 bp to about 2000 bp, about 750 bp to about 2000 bp, about 750 bp to about 1500 bp, or about 1000 bp to about 1500 bp, including all intervening lengths of homology arms.

In a particular embodiment, the lengths of the 5' and 3' homology arms are independently selected from about 500 bp to about 1500 bp. In one embodiment, the 5'homology arm is about 1500 bp and the 3' homology arm is about 1000 bp. In one embodiment, the 5'homology arm is between about 200 bp to about 600 bp and the 3' homology arm is between about 200 bp to about 600 bp. In one embodiment, the 5'homology arm is about 200 bp and the 3' homology arm is about 200 bp. In one embodiment, the 5'homology arm is about 300 bp and the 3' homology arm is about 300 bp. In one embodiment, the 5'homology arm is about 400 bp and the 3' homology arm is about 400 bp. In one embodiment, the 5'homology arm is about 500 bp and the 3' homology arm is about 500 bp. In one embodiment, the 5'homology arm is about 600 bp and the 3' homology arm is about 600 bp.

Donor repair templates may further comprises one or more polynucleotides such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, contemplated elsewhere herein.

In one embodiment, the donor repair template comprises a polynucleotide comprising a PDCD-1 gene or portion thereof and is designed to introduce one or more mutations in a genomic PDCD-1 sequence such that a mutant PDCD-1 gene product is expressed. In one embodiment, the mutant PDCD-1 has decreased ligand binding and/or a reduction in intracellular signaling.

In various embodiments, the donor repair template comprises a 5' homology arm, an RNA polymerase II promoter, one or more polynucleotides encoding an immunopotency enhancer, an immunosuppressive signal damper, or an engineered antigen receptor, and a 3' homology arm.

In various embodiments, a target site is modified with a donor repair template comprising a 5' homology arm, one or more polynucleotides encoding self-cleaving viral peptide, e.g., T2A, an immunopotency enhancer, an immunosuppressive signal damper, or an engineered antigen receptor, optionally a poly(A) signal or self-cleaving peptide, and a 3' homology arm, wherein expression of the one or more polynucleotides is governed by the endogenous PDCD-1 promoter.

1. Engineered Antigen Receptors

In particular embodiments, the genome edited immune effector cells contemplated herein comprise an engineered antigen receptor. In one embodiment, T cells are engineered by introducing a DSB in one or more PDCD-1 genes in the presence of a donor repair template encoding an engineered antigen receptor.

In particular embodiments, the engineered antigen receptor is an engineered T cell receptor (TCR), a chimeric antigen receptor (CAR), a dimerizing agent regulated immunoreceptor complex (DARIC) or components thereof, or a chimeric cytokine receptor.

a. Engineered TCRs

In particular embodiments, the genome edited immune effector cells contemplated herein comprise an engineered TCR. In one embodiment, T cells are engineered by introducing a DSB in one or more PDCD-1 genes in the presence of a donor repair template encoding an engineered TCR. In a particular embodiment, an engineered TCR is inserted at a DSB in a single PDCD-1 gene.

Naturally occurring T cell receptors comprise two subunits, an alpha chain and a beta chain subunit (αβTCR), or a gamma chain and a delta chain subunit (γδTCR), each of which is a unique protein produced by recombination event in each T cell's genome. Libraries of TCRs may be screened for their selectivity to particular target antigens. In this manner, natural TCRs, which have a high-avidity and reactivity toward target antigens may be selected, cloned, and subsequently introduced into a population of T cells used for adoptive immunotherapy. In one embodiment, the TCR is an αβTCR. In one embodiment, the TCR is a γδTCR.

In one embodiment, T cells are modified by introducing donor repair template comprising a polynucleotide encoding a subunit of a TCR at a DSB in one or more PDCD-1 genes, wherein the TCR subunit has the ability to form TCRs that confer specificity to T cells for tumor cells expressing a target antigen. In particular embodiments, the subunits have one or more amino acid substitutions, deletions, insertions, or modifications compared to the naturally occurring subunit, so long as the subunits retain the ability to form TCRs and confer upon transfected T cells the ability to home to target cells, and participate in immunologically-relevant cytokine signaling. The engineered TCRs preferably also bind target cells displaying the relevant tumor-associated peptide with high avidity, and optionally mediate efficient killing of target cells presenting the relevant peptide in vivo.

The nucleic acids encoding engineered TCRs are preferably isolated from their natural context in a (naturally-occurring) chromosome of a T cell, and can be incorporated into suitable vectors as described elsewhere herein. Both the nucleic acids and the vectors comprising them can be transferred into a cell, preferably a T cell in particular embodiments. The modified T cells are then able to express one or more chains of a TCR encoded by the transduced nucleic acid or nucleic acids. In preferred embodiments, the engineered TCR is an exogenous TCR because it is introduced into T cells that do not normally express the particular TCR. The essential aspect of the engineered TCRs is that it has high avidity for a tumor antigen presented by a major histocompatibility complex (MHC) or similar immunological component. In contrast to engineered TCRs, CARs are engineered to bind target antigens in an MHC independent manner.

The TCR can be expressed with additional polypeptides attached to the amino-terminal or carboxyl-terminal portion of the TCR so long as the attached additional polypeptide does not interfere with the ability of the chains to form a functional T cell receptor and the MHC dependent antigen recognition.

Antigens that are recognized by the engineered TCRs contemplated in particular embodiments include, but are not limited to cancer antigens, including antigens on both hematological cancers and solid tumors. Illustrative antigens include, but are not limited to alpha folate receptor (FRα), α$_v$β$_6$ integrin, B cell maturation antigen (BCMA), B7-H3 (CD276), B7-H6, carbonic anhydrase IX (CAIX), CD16, CD19, CD20, CD22, CD30, CD33, CD37, CD38, CD44, CD44v6, CD44v7/8, CD70, CD79a, CD79b, CD123, CD133, CD138, CD171, carcinoembryonic antigen (CEA), C-type lectin-like molecule-1 (CLL-1), CD2 subset 1 (CS-1), chondroitin sulfate proteoglycan 4 (CSPG4), cutaneous T cell lymphoma-associated antigen 1 (CTAGE1), epidermal growth factor receptor (EGFR), epidermal growth factor receptor variant III (EGFRvIII), epithelial glycoprotein 2 (EGP2), epithelial glycoprotein 40 (EGP40), epithelial cell adhesion molecule (EPCAM), ephrin type-A receptor 2 (EPHA2), fibroblast activation protein (FAP), Fc Receptor Like 5 (FCRL5), fetal acetylcholinesterase receptor (AchR), ganglioside G2 (GD2), ganglioside G3 (GD3), Glypican-3 (GPC3), EGFR family including ErbB2 (HER2), IL-11Rα, IL-13Rα2, Kappa, cancer/testis antigen 2 (LAGE-1A), Lambda, Lewis-Y (LeY), L1 cell adhesion molecule (L1-CAM), melanoma antigen gene (MAGE)-A1, MAGE-A3, MAGE-A4, MAGE-A6, MAGEA10, melanoma antigen recognized by T cells 1 (MelanA or MART1), Mesothelin (MSLN), MUC1, MUC16, MHC class I chain related proteins A (MICA), MH1C class I chain related proteins B (MICB), neural cell adhesion molecule (NCAM), cancer/testis antigen 1 (NY-ESO-1), polysialic acid; placenta-specific 1 (PLAC1), preferentially expressed antigen in melanoma (PRAME), prostate stem cell antigen (PSCA), prostate-specific membrane antigen (PSMA), receptor tyrosine kinase-like orphan receptor 1 (ROR1), synovial sarcoma, X breakpoint 2 (SSX2), Survivin, tumor associated glycoprotein 72 (TAG72), tumor endothelial marker 1 (TEM1/CD248), tumor endothelial marker 7-related (TEM7R), trophoblast glycoprotein (TPBG), UL16-binding protein (ULBP) 1, ULBP2, ULBP3, ULBP4, ULBP5, ULBP6, vascular endothelial growth factor receptor 2 (VEGFR2), and Wilms tumor 1 (WT-1).

b. Chimeric Antigen Receptors (CARs)

In particular embodiments, the engineered immune effector cells contemplated herein comprise one or more chimeric antigen receptors (CARs). In one embodiment, T cells are engineered by introducing a DSB in one or more PDCD-1 genes in the presence of a donor repair template encoding a

26

CAR. In a particular embodiment, a CAR is inserted at a DSB in a single PDCD-1 gene.

In various embodiments, the genome edited T cells express CARs that redirect cytotoxicity toward tumor cells. CARs are molecules that combine antibody-based specificity for a target antigen (e.g., tumor antigen) with a T cell receptor-activating intracellular domain to generate a chimeric protein that exhibits a specific anti-tumor cellular immune activity. As used herein, the term, "chimeric," describes being composed of parts of different proteins or DNAs from different origins.

In various embodiments, a CAR comprises an extracellular domain that binds to a specific target antigen (also referred to as a binding domain or antigen-specific binding domain), a transmembrane domain and an intracellular signaling domain. The main characteristics of CARs are their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific coreceptors.

In particular embodiments, CARs comprise an extracellular binding domain that specifically binds to a target polypeptide, e.g., target antigen, expressed on tumor cell. As used herein, the terms, "binding domain," "extracellular domain," "extracellular binding domain," "antigen binding domain," "antigen-specific binding domain," and "extracellular antigen specific binding domain," are used interchangeably and provide a chimeric receptor, e.g., a CAR or Daric, with the ability to specifically bind to the target antigen of interest. A binding domain may comprise any protein, polypeptide, oligopeptide, or peptide that possesses the ability to specifically recognize and bind to a biological molecule (e.g., a cell surface receptor or tumor protein, lipid, polysaccharide, or other cell surface target molecule, or component thereof). A binding domain includes any naturally occurring, synthetic, semi-synthetic, or recombinantly produced binding partner for a biological molecule of interest.

In particular embodiments, the extracellular binding domain comprises an antibody or antigen binding fragment thereof.

An "antibody" refers to a binding agent that is a polypeptide comprising at least a light chain or heavy chain immunoglobulin variable region which specifically recognizes and binds an epitope of a target antigen, such as a peptide, lipid, polysaccharide, or nucleic acid containing an antigenic determinant, such as those recognized by an immune cell. Antibodies include antigen binding fragments, e.g., Camel Ig (a camelid antibody or VHH fragment thereof), Ig NAR, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody) or other antibody fragments thereof. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, Ill.); Kuby, J., Immunology, 3rd Ed., W. H. Freeman & Co., New York, 1997.

In one preferred embodiment, the binding domain is an scFv.

In another preferred embodiment, the binding domain is a camelid antibody.

In particular embodiments, the CAR comprises an extracellular domain that binds an antigen selected from the group consisting of FRα, α$_v$β$_6$ integrin, BCMA, B7-H3, B7-H6, CAIX, CD16, CD19, CD20, CD22, CD30, CD33, CD37, CD38, CD44, CD44v6, CD44v7/8, CD70, CD79a, CD79b, CD123, CD133, CD138, CD171, CEA, CLL-1, CS-1, CSPG4, CTAGE1, EGFR, EGFRvIII, EGP2, EGP40, EPCAM, EPHA2, FAP, FCRL5, AchR, GD2, GD3, GPC3, HER2, IL-11Rα, IL-13Rα2, Kappa, LAGE-1A, Lambda, LeY, L1-CAM, MAGE-A1, MAGE-A3, MAGE-A4, MAGE-A6, MAGE-A10, MART1, MSLN, MUC1, MUC16, MICA, MICB, NCAM, NY-ESO-1, PLAC1, PRAME, PSCA, PSMA, ROR1, SSX2, Survivin, TAG72, TEM1, TEM7R, TPBG, ULBP1, ULBP2, ULBP3, ULBP4, ULBP5, ULBP6, VEGFR2, and WT-1.

In particular embodiments, the CARs comprise an extracellular binding domain, e.g., antibody or antigen binding fragment thereof that binds an antigen, wherein the antigen is an MHC-peptide complex, such as a class I MHC-peptide complex or a class II MHC-peptide complex.

In certain embodiments, the CARs comprise linker residues between the various domains. A "variable region linking sequence," is an amino acid sequence that connects a heavy chain variable region to a light chain variable region and provides a spacer function compatible with interaction of the two binding domains so that the resulting polypeptide retains a specific binding affinity to the same target molecule as an antibody that comprises the same light and heavy chain variable regions. In particular embodiments, CARs comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

In particular embodiments, the binding domain of the CAR is followed by one or more "spacer domains," which refers to the region that moves the antigen binding domain away from the effector cell surface to enable proper cell/cell contact, antigen binding and activation (Patel et al., Gene Therapy, 1999; 6: 412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

In one embodiment, the spacer domain comprises the CH2 and CH3 of IgG1, IgG4, or IgD.

In one embodiment, the binding domain of the CAR is linked to one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region.

Illustrative hinge domains suitable for use in the CARs described herein include the hinge region derived from the extracellular regions of type 1 membrane proteins such as CD8a, and CD4, which may be wild-type hinge regions from these molecules or may be altered. In another embodiment, the hinge domain comprises a CD8a hinge region.

In one embodiment, the hinge is a PDCD-1 hinge or CD152 hinge.

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source.

Illustrative TM domains may be derived from (i.e., comprise at least the transmembrane region(s) of the alpha or beta chain of the T-cell receptor, CD3δ, CD3ϑ, CD3γ, CD3ζ, CD4, CD5, CD8α, CD9, CD 16, CD22, CD27, CD28, CD33, CD37, CD45, CD64, CD80, CD86, CD 134, CD137, CD152, CD154, AMN, and PDCD-1.

In one embodiment, a CAR comprises a TM domain derived from CD8a. In another embodiment, a CAR contemplated herein comprises a TM domain derived from CD8a and a short oligo- or polypeptide linker, preferably between 1, 2, 3, 4, 5, 6, 7, 8, 9, or 10 amino acids in length that links the TM domain and the intracellular signaling domain of the CAR. A glycine-serine linker provides a particularly suitable linker.

In particular embodiments, a CAR comprises an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain.

The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or costimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and costimulatory signaling domains that act in an antigen-independent manner to provide a secondary or costimulatory signal. In preferred embodiments, a CAR comprises an intracellular signaling domain that comprises one or more "costimulatory signaling domains" and a "primary signaling domain." Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs.

Illustrative examples of ITAM containing primary signaling domains suitable for use in CARs contemplated in particular embodiments include those derived from FcR$\gamma$, FcR$\beta$, CD3$\gamma$, CD3$\delta$, CD3$\epsilon$, CD3$\zeta$, CD22, CD79a, CD79b, and CD66d. In particular preferred embodiments, a CAR comprises a CD3$\zeta$ primary signaling domain and one or more costimulatory signaling domains. The intracellular primary signaling and costimulatory signaling domains may be linked in any order in tandem to the carboxyl terminus of the transmembrane domain.

In particular embodiments, a CAR comprises one or more costimulatory signaling domains to enhance the efficacy and expansion of T cells expressing CAR receptors. As used herein, the term, "costimulatory signaling domain," or "costimulatory domain", refers to an intracellular signaling domain of a costimulatory molecule.

Illustrative examples of such costimulatory molecules suitable for use in CARs contemplated in particular embodiments include TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In one embodiment, a CAR comprises one or more costimulatory signaling domains selected from the group consisting of CD28, CD137, and CD134, and a CD3$\zeta$ primary signaling domain.

In various embodiments, the CAR comprises: an extracellular domain that binds an antigen selected from the group consisting of BCMA, CD19, CSPG4, PSCA, ROR1, and TAG72; a transmembrane domain isolated from a polypeptide selected from the group consisting of CD4, CD8a, CD154, and PDCD-1; one or more intracellular costimulatory signaling domains isolated from a polypeptide selected from the group consisting of CD28, CD134, and CD137; and a signaling domain isolated from a polypeptide selected from the group consisting of: FcR$\gamma$, FcR$\beta$, CD3$\gamma$, CD3$\delta$, CD3$\vartheta$, CD3$\zeta$, CD22, CD79a, CD79b, and CD66d.

c. DARIC

In particular embodiments, the engineered immune effector cells comprise one or more components of a DARIC. As used herein, the term "DARIC" refers to a dimerizing agent regulated multichain engineered antigen receptor. In one embodiment, T cells are engineered by introducing a DSB in one or more PDCD-1 genes in the presence of a donor repair template encoding one or more components of a DARIC. In a particular embodiment, a DARIC or one or more components thereof is inserted at a DSB in a single PDCD-1 gene.

Illustrative examples of DARIC architectures and components are disclosed in PCT Publication No. WO2015/017214 and U.S. Patent Publication No. 20150266973, each of which is incorporated here by reference in its entirety.

In one embodiment, a donor repair template comprises the following DARIC components: a signaling polypeptide comprising a first multimerization domain, a first transmembrane domain, and one or more intracellular co-stimulatory signaling domains and/or primary signaling domains; and a binding polypeptide comprising a binding domain, a second multimerization domain, and optionally a second transmembrane domain. A functional DARIC comprises a bridging factor that promotes the formation of a DARIC receptor complex on the cell surface with the bridging factor associated with and disposed between the multimerization domains of the signaling polypeptide and the binding polypeptide.

In certain embodiments, multimerization domains will associate with a bridging factor being a rapamycin or rapalog thereof. For example, the first and second multimerization domains are a pair selected from FKBP and FRB. FRB domains are polypeptide regions (protein "domains") that are capable of forming a tripartite complex with an FKBP protein and rapamycin or rapalog thereof. FRB domains are present in a number of naturally occurring proteins, including mTOR proteins (also referred to in the literature as FRAP, RAPT1, or RAFT) from human and other species; yeast proteins including Tor1 and Tor2; and a *Candida* FRAP homolog. Information concerning the nucleotide sequences, cloning, and other aspects of these proteins is already known in the art. For example, a protein sequence accession number for a human mTOR is GenBank Accession No. L34075.1 (Brown et al., Nature 369:756, 1994).

Illustrative examples of rapamycin analogs (rapalogs) include those disclosed in U.S. Pat. No. 6,649,595, which rapalog structures are incorporated herein by reference in their entirety. In certain embodiments, a bridging factor is a rapalog with substantially reduced immunosuppressive effect as compared to rapamycin. A "substantially reduced immunosuppressive effect" refers to a rapalog having at least less than 0.1 to 0.005 times the immunosuppressive effect observed or expected for an equimolar amount of rapamycin, as measured either clinically or in an appropriate in vitro (e.g., inhibition of T cell proliferation) or in vivo surrogate of human immunosuppressive activity. In one embodiment, "substantially reduced immunosuppressive effect" refers to a rapalog having an EC50 value in such an in vitro assay that is at least 10 to 250 times larger than the EC50 value observed for rapamycin in the same assay.

Other illustrative examples of rapalogs include, but are not limited to everolimus, novolimus, pimecrolimus, ridaforolimus, tacrolimus, temsirolimus, umirolimus, and zotarolimus.

FRB domains suitable for use in particular embodiments contemplated herein generally contain at least about 85 to about 100 amino acid residues. In certain embodiments, an FRB amino acid sequence for use in fusion proteins of this disclosure will comprise a 93 amino acid sequence Ile-2021 through Lys-2113 and a mutation of T2098L, based the amino acid sequence of GenBank Accession No. L34075.1. An FRB domain for use in Darics contemplated in particular embodiments will be capable of binding to a complex of an FKBP protein bound to rapamycin or a rapalog thereof. In certain embodiments, a peptide sequence of an FRB domain comprises (a) a naturally occurring peptide sequence spanning at least the indicated 93 amino acid region of human mTOR or corresponding regions of homologous proteins; (b) a variant of a naturally occurring FRB in which up to about ten amino acids, or about 1 to about 5 amino acids or about 1 to about 3 amino acids, or in some embodiments just one amino acid, of the naturally-occurring peptide have been deleted, inserted, or substituted; or (c) a peptide encoded by a nucleic acid molecule capable of selectively hybridizing to a DNA molecule encoding a naturally occurring FRB domain or by a DNA sequence which would be capable, but for the degeneracy of the genetic code, of selectively hybridizing to a DNA molecule encoding a naturally occurring FRB domain.

FKBPs (FK506 binding proteins) are the cytosolic receptors for macrolides, such as FK506, FK520 and rapamycin, and are highly conserved across species lines. FKBPs are proteins or protein domains that are capable of binding to rapamycin or to a rapalog thereof and further forming a tripartite complex with an FRB-containing protein or fusion protein. An FKBP domain may also be referred to as a "rapamycin binding domain." Information concerning the nucleotide sequences, cloning, and other aspects of various FKBP species is known in the art (see, e.g., Staendart et al., Nature 346:671, 1990 (human FKBP12); Kay, Biochem. J. 314:361, 1996). Homologous FKBP proteins in other mammalian species, in yeast, and in other organisms are also known in the art and may be used in the fusion proteins disclosed herein. An FKBP domain contemplated in particular embodiments will be capable of binding to rapamycin or a rapalog thereof and participating in a tripartite complex with an FRB-containing protein (as may be determined by any means, direct or indirect, for detecting such binding).

Illustrative examples of FKBP domains suitable for use in a DARIC contemplated in particular embodiments include, but are not limited to: a naturally occurring FKBP peptide sequence, preferably isolated from the human FKBP12 protein (GenBank Accession No. AAA58476.1) or a peptide sequence isolated therefrom, from another human FKBP, from a murine or other mammalian FKBP, or from some other animal, yeast or fungal FKBP; a variant of a naturally occurring FKBP sequence in which up to about ten amino acids, or about 1 to about 5 amino acids or about 1 to about 3 amino acids, or in some embodiments just one amino acid, of the naturally-occurring peptide have been deleted, inserted, or substituted; or a peptide sequence encoded by a nucleic acid molecule capable of selectively hybridizing to a DNA molecule encoding a naturally occurring FKBP or by a DNA sequence which would be capable, but for the degeneracy of the genetic code, of selectively hybridizing to a DNA molecule encoding a naturally occurring FKBP.

In one embodiment, the first multimerization domain comprises FRB T2098L, the second multimerization domain comprises FKBP12, and the bridging factor is rapalog AP21967.

In another embodiment, the first multimerization domain comprises FRB, the second multimerization domain comprises FKBP12, and the bridging factor is Rapamycin, temsirolimus or everolimus.

In particular embodiments, a DARIC signaling component comprises a first transmembrane domain and a DARIC binding component comprises a second transmembrane domain or GPI anchor. Illustrative examples of the first and second transmembrane domains are isolated from a polypeptide independently selected from the group consisting of: CD36, CD3ϑ, CD3γ, CD3ζ, CD4, CD5, CD8α, CD9, CD16, CD22, CD27, CD28, CD33, CD37, CD45, CD64, CD80, CD86, CD 134, CD137, CD152, CD154, AMN, and PDCD-1.

In one embodiment, a DARIC signaling component comprises one or more intracellular co-stimulatory signaling domains and/or primary signaling domains.

Illustrative examples of primary signaling domains suitable for use in DARIC signaling components contemplated in particular embodiments include those derived from FcRγ, FcRβ, CD3γ, CD3δ, CD3ϑ, CD3ζ, CD22, CD79a, CD79b, and CD66d. In particular preferred embodiments, a DARIC signaling component comprises a CD3ζ primary signaling domain and one or more costimulatory signaling domains. The intracellular primary signaling and costimulatory signaling domains may be linked in any order in tandem to the carboxyl terminus of the transmembrane domain.

Illustrative examples of such costimulatory molecules suitable for use in DARIC signaling component contemplated in particular embodiments include TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In one embodiment, a DARIC signaling component comprises one or more costimulatory signaling domains selected from the group consisting of CD28, CD137, and CD134, and a CD3ζ primary signaling domain.

In particular embodiments, a DARIC binding component comprises a binding domain. In one embodiment, the binding domain is an antibody or antigen binding fragment thereof.

In particular embodiments, antibodies and antigen binding fragments thereof suitable for use in particular DARIC binding components include, but are not limited to, murine antibodies, camelid antibodies, chimeric antibodies, humanized antibodies, or human antibodies. In preferred embodiments, the antibody or antigen binding fragment thereof is derived from a monoclonal antibody.

Illustrative examples of antibodies and antigen binding fragments thereof suitable for use in particular DARIC binding components include, but are not limited to, a Camel Ig, a Llama Ig, an Alpaca Ig, an Alpaca Ig, Ig NAR, a Fab' fragment, a F(ab')₂ fragment, a bispecific Fab dimer (Fab2), a trispecific Fab trimer (Fab3), an Fv, an single chain Fv protein ("scFv"), a bis-scFv, (scFv)₂, a minibody, a diabody, a triabody, a tetrabody, a disulfide stabilized Fv protein ("dsFv"), and a single-domain antibody (sdAb, a camelid VHH, Nanobody).

In a preferred embodiment, the binding domain comprises an scFv.

In a preferred embodiment, the binding domain comprises one or more camelid VHH antibodies.

In particular embodiments, the DARIC binding component comprises an extracellular domain that binds an antigen selected from the group consisting of: FRα, $\alpha_v\beta_6$ integrin, BCMA, B7-H3, B7-H6, CAIX, CD16, CD19, CD20, CD22, CD30, CD33, CD37, CD38, CD44, CD44v6, CD44v7/8, CD70, CD79a, CD79b, CD123, CD133, CD138, CD171, CEA, CLL-1, CS-1, CSPG4, CTAGE1, EGFR, EGFRvIII, EGP2, EGP40, EPCAM, EPHA2, FAP, FCRL5, AchR, GD2, GD3, GPC3, HER2, IL-11Rα, IL-13Rα2, Kappa, LAGE-1A, Lambda, LeY, L1-CAM, MAGE-A1, MAGE-A3, MAGE-A4, MAGE-A6, MAGE-A10, MART1, MSLN, MUC1, MUC16, MICA, MICB, NCAM, NY-ESO-1, PLAC1, PRAME, PSCA, PSMA, ROR1, SSX2, Survivin, TAG72, TEM1, TEM7R, TPBG, ULBP 1, ULBP2, ULBP3, ULBP4, ULBP5, ULBP6, VEGFR2, and WT-1.

In particular embodiments, the DARIC components contemplated herein comprise a linker or spacer that connects two proteins, polypeptides, peptides, domains, regions, or motifs.

In particular embodiments, the DARIC components contemplated herein comprise one or more "hinge domains," which plays a role in positioning the domains to enable proper cell/cell contact, antigen binding and activation. In particular embodiment, the hinge is a CD8a hinge or a CD4 hinge.

In one embodiment, a DARIC comprises a signaling polypeptide comprises a first multimerization domain of FRB T2098L, a CD8 transmembrane domain, a 4-1BB costimulatory domain, and a CD3ζ primary signaling domain; the binding polypeptide comprises an scFv that binds CD19, a second multimerization domain of FKBP12 and a CD4 transmembrane domain; and the bridging factor is rapalog AP21967.

In one embodiment, a DARIC comprises a signaling polypeptide comprises a first multimerization domain of FRB, a CD8 transmembrane domain, a 4-1BB costimulatory domain, and a CD3ζ primary signaling domain; the binding polypeptide comprises an scFv that binds CD19, a second multimerization domain of FKBP12 and a CD4 transmembrane domain; and the bridging factor is Rapamycin, temsirolimus or everolimus.

d. Zetakines

In particular embodiments, the engineered immune effector cells contemplated herein comprise one or more chimeric cytokine receptors. In one embodiment, T cells are engineered by introducing a DSB in one or more PDCD-1 genes in the presence of a donor repair template encoding a CAR. In a particular embodiment, a chimeric cytokine receptor is inserted at a DSB in a single PDCD-1 gene.

In various embodiments, the genome edited T cells express chimeric cytokine receptor that redirect cytotoxicity toward tumor cells. Zetakines are chimeric transmembrane immunoreceptors that comprise an extracellular domain comprising a soluble receptor ligand linked to a support region capable of tethering the extracellular domain to a cell surface, a transmembrane region and an intracellular signaling domain. Zetakines, when expressed on the surface of T lymphocytes, direct T cell activity to those cells expressing a receptor for which the soluble receptor ligand is specific. Zetakine chimeric immunoreceptors redirect the antigen specificity of T cells, with application to treatment of a variety of cancers, particularly via the autocrine/paracrine cytokine systems utilized by human malignancy.

In particular embodiments, the chimeric cytokine receptor comprises an immunosuppressive cytokine or cytokine receptor binding variant thereof, a linker, a transmembrane domain, and an intracellular signaling domain.

In particular embodiments, the cytokine or cytokine receptor binding variant thereof is selected from the group consisting of: interleukin-4 (IL-4), interleukin-6 (IL-6), interleukin-8 (IL-8), interleukin-10 (IL-10), and interleukin-13 (IL-13).

In certain embodiments, the linker comprises a CH2CH3 domain, hinge domain, or the like. In one embodiment, a linker comprises the CH2 and CH3 domains of IgG1, IgG4, or IgD. In one embodiment, a linker comprises a CD8a or CD4 hinge domain.

In particular embodiments, the transmembrane domain is selected from the group consisting of: the alpha or beta chain of the T-cell receptor, CD3δ, CD3θ, CD3γ, CD3ζ, CD4, CD5, CD8α, CD9, CD 16, CD22, CD27, CD28, CD33, CD37, CD45, CD64, CD80, CD86, CD 134, CD137, CD152, CD154, AMN, and PDCD-1.

In particular embodiments, the intracellular signaling domain is selected from the group consisting of: an ITAM containing primary signaling domain and/or a costimulatory domain.

In particular embodiments, the intracellular signaling domain is selected from the group consisting of: FcRγ, FcRβ, CD3γ, CD3δ, CD3θ, CD3ζ, CD22, CD79a, CD79b, and CD66d.

In particular embodiments, the intracellular signaling domain is selected from the group consisting of: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70.

In one embodiment, a chimeric cytokine receptor comprises one or more costimulatory signaling domains selected from the group consisting of CD28, CD137, and CD134, and a CD3ζ primary signaling domain.

F. Polypeptides

Various polypeptides are contemplated herein, including, but not limited to, homing endonuclease variants and megaTALs engineered to increase thermostability and/or enzymatic activity, and fusion polypeptides. In preferred embodiments, a polypeptide comprises the amino acid sequence set forth in SEQ ID NOs: 6 and 7. "Polypeptide," "peptide" and "protein" are used interchangeably, unless specified to the contrary, and according to conventional meaning, i.e., as a sequence of amino acids. In one embodiment, a "polypeptide" includes fusion polypeptides and other variants. Polypeptides can be prepared using any of a variety of well-known recombinant and/or synthetic techniques. Polypeptides are not limited to a specific length, e.g., they may comprise a full-length protein sequence, a fragment of a full-length protein, or a fusion protein, and may include post-translational modifications of the polypeptide, for example, glycosylations, acetylations, phosphorylations and the like, as well as other modifications known in the art, both naturally occurring and non-naturally occurring.

An "isolated protein," "isolated peptide," or "isolated polypeptide" and the like, as used herein, refer to in vitro synthesis, isolation, and/or purification of a peptide or polypeptide molecule from a cellular environment, and from association with other components of the cell, i.e., it is not significantly associated with in vivo substances. In particular embodiments, an isolated polypeptide is a synthetic polypeptide, a semi-synthetic polypeptide, or a polypeptide obtained or derived from a recombinant source.

Polypeptides include "polypeptide variants." Polypeptide variants may differ from a naturally occurring polypeptide in one or more amino acid substitutions, deletions, additions and/or insertions. Such variants may be naturally occurring or may be synthetically generated, for example, by modifying one or more amino acids of the above polypeptide sequences. For example, in particular embodiments, it may be desirable to improve the biological properties of a homing endonuclease, megaTAL or the like that binds and cleaves a target site in the human PDCD-1 gene by introducing one or more substitutions, deletions, additions and/or insertions into the polypeptide. In particular embodiments, polypeptides include polypeptides having at least about 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity to any of the reference sequences contemplated herein, typically where the variant maintains at least one biological activity of the reference sequence.

In preferred embodiments, polypeptide variants include homing endonucleases or megaTALs that have been engineered to increase their thermostability and/or activity. I-OnuI HE polypeptides or fragments thereof can be reprogrammed to bind and cleave a target site. In particular embodiments, a reprogrammed I-OnuI HE variant has relatively low thermostability and/or activity compared to a parent I-OnuI HE. In preferred embodiments, an I-OnuI homing endonuclease or fragment thereof is engineered to bind and cleave a target site and to increase thermostability and/or activity of the enzyme.

Polypeptide variants include biologically active "polypeptide fragments." Illustrative examples of biologically active polypeptide fragments include DNA binding domains, nuclease domains, and the like. As used herein, the term "biologically active fragment" or "minimal biologically active fragment" refers to a polypeptide fragment that retains at least 100%, at least 90%, at least 80%, at least 70%, at least 60%, at least 50%, at least 40%, at least 30%, at least 20%, at least 10%, or at least 5% of the naturally occurring polypeptide activity. In preferred embodiments, the biological activity is binding affinity and/or cleavage activity for a target sequence. In certain embodiments, a polypeptide fragment can comprise an amino acid chain at least 5 to about 1700 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more amino acids long. In particular embodiments, a polypeptide comprises a biologically active fragment of a homing endonuclease variant. In particular embodiments, the polypeptides set forth herein may comprise one or more amino acids denoted as "X." "X" if present in an amino acid SEQ ID NO, refers to any amino acid. One or more "X" residues may be present at the N- and C-terminus of an amino acid sequence set forth in particular SEQ ID NOs contemplated herein. If the "X" amino acids are not present the remaining amino acid sequence set forth in a SEQ ID NO may be considered a biologically active fragment.

In particular embodiments, a polypeptide comprises a biologically active fragment of a homing endonuclease variant, e.g., SEQ ID NO: 6, or a megaTAL (SEQ ID NO: 7). The biologically active fragment may comprise an N-terminal truncation and/or C-terminal truncation. In a particular embodiment, a biologically active fragment lacks or comprises a deletion of the 1, 2, 3, 4, 5, 6, 7, or 8 N-terminal amino acids of a homing endonuclease variant compared to a corresponding wild type homing endonuclease sequence, more preferably a deletion of the 4 N-terminal amino acids of a homing endonuclease variant compared to a corresponding wild type homing endonuclease sequence. In a particular embodiment, a biologically active fragment lacks or comprises a deletion of the 1, 2, 3, 4, or 5 C-terminal amino acids of a homing endonuclease variant compared to a corresponding wild type homing endonuclease sequence, more preferably a deletion of the 2 C-terminal amino acids of a homing endonuclease variant compared to a corresponding wild type homing endonuclease sequence. In a particular preferred embodiment, a biologically active fragment lacks or comprises a deletion of the 4 N-terminal amino acids and 2 C-terminal amino acids of a homing endonuclease variant compared to a corresponding wild type homing endonuclease sequence.

In a particular embodiment, an I-OnuI variant comprises a deletion of 1, 2, 3, 4, 5, 6, 7, or 8 the following N-terminal amino acids: M, A, Y, M, S, R, R, E; and/or a deletion of the following 1, 2, 3, 4, or 5 C-terminal amino acids: R, G, S, F, V.

In a particular embodiment, an I-OnuI variant comprises a deletion or substitution of 1, 2, 3, 4, 5, 6, 7, or 8 the following N-terminal amino acids: M, A, Y, M, S, R, R, E; and/or a deletion or substitution of the following 1, 2, 3, 4, or 5 C-terminal amino acids: R, G, S, F, V.

In a particular embodiment, an I-OnuI variant comprises a deletion of 1, 2, 3, 4, 5, 6, 7, or 8 the following N-terminal amino acids: M, A, Y, M, S, R, R, E; and/or a deletion of the following 1 or 2 C-terminal amino acids: F, V.

In a particular embodiment, an I-OnuI variant comprises a deletion or substitution of 1, 2, 3, 4, 5, 6, 7, or 8 the following N-terminal amino acids: M, A, Y, M, S, R, R, E;

and/or a deletion or substitution of the following 1 or 2 C-terminal amino acids: F, V.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA*. 82: 488-492), Kunkel et al., (1987, *Methods in Enzymol*, 154: 367-382), U.S. Pat. No. 4,873,192, Watson, J. D. et al., (*Molecular Biology of the Gene*, Fourth Edition, Benjamin/ Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure (Natl. Biomed Res. Found.*, Washington, D.C.).

In certain embodiments, a variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides contemplated in particular embodiments, polypeptides include polypeptides having at least about and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence, e.g., according to Table 1.

TABLE 1

| Amino Acid Codons | | | | | | | |
|---|---|---|---|---|---|---|---|
| Amino Acids | One letter code | Three letter code | | | Codons | | |
| Alanine | A | Ala | GCA | GCC | GCG | GCU | |
| Cysteine | C | Cys | UGC | UGU | | | |
| Aspartic acid | D | Asp | GAC | GAU | | | |
| Glutamic acid | E | Glu | GAA | GAG | | | |
| Phenylalanine | F | Phe | UUC | UUU | | | |
| Glycine | G | Gly | GGA | GGC | GGG | GGU | |
| Histidine | H | His | CAC | CAU | | | |
| Isoleucine | I | Iso | AUA | AUC | AUU | | |
| Lysine | K | Lys | AAA | AAG | | | |
| Leucine | L | Leu | UUA | UUG | CUA | CUC | CUG | CUU |
| Methionine | M | Met | AUG | | | | |
| Asparagine | N | Asn | AAC | AAU | | | |
| Proline | P | Pro | CCA | CCC | CCG | CCU | |
| Glutamine | Q | Gln | CAA | CAG | | | |
| Arginine | R | Arg | AGA | AGG | CGA | CGC | CGG | CGU |
| Serine | S | Ser | AGC | AGU | UCA | UCC | UCG | UCU |
| Threonine | T | Thr | ACA | ACC | ACG | ACU | |
| Valine | V | Val | GUA | GUC | GUG | GUU | |
| Tryptophan | W | Trp | UGG | | | | |
| Tyrosine | Y | Tyr | UAC | UAU | | | |

Guidance in determining which amino acid residues can be substituted, inserted, or deleted in particular embodiments, without abolishing biological activity can be found using computer programs well known in the art, such as DNASTAR, DNA Strider, Geneious, Mac Vector, or Vector NTI software. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224).

In one embodiment, where expression of two or more polypeptides is desired, the polynucleotide sequences encoding them can be separated by and IRES sequence as disclosed elsewhere herein.

Polypeptides contemplated in particular embodiments include fusion polypeptides. In particular embodiments, fusion polypeptides and polynucleotides encoding fusion polypeptides are provided. Fusion polypeptides and fusion proteins refer to a polypeptide having at least two, three, four, five, six, seven, eight, nine, or ten polypeptide segments.

In another embodiment, two or more polypeptides can be expressed as a fusion protein that comprises one or more self-cleaving polypeptide sequences as disclosed elsewhere herein.

In one embodiment, a fusion protein contemplated herein comprises one or more DNA binding domains and one or more nucleases, and one or more linker and/or self-cleaving polypeptides.

In one embodiment, a fusion protein contemplated herein comprises nuclease variant; a linker or self-cleaving peptide; and an end-processing enzyme including but not limited to a 5'-3' exonuclease, a 5'-3' alkaline exonuclease, and a 3'-5' exonuclease (e.g., Trex2).

Fusion polypeptides can comprise one or more polypeptide domains or segments including, but are not limited to signal peptides, cell permeable peptide domains (CPP), DNA binding domains, nuclease domains, etc., epitope tags (e.g., maltose binding protein ("MBP"), glutathione S transferase (GST), HIS6, MYC, FLAG, V5, VSV-G, and HA), polypeptide linkers, and polypeptide cleavage signals. Fusion polypeptides are typically linked C-terminus to N-terminus, although they can also be linked C-terminus to C-terminus, N-terminus to N-terminus, or N-terminus to C-terminus. In particular embodiments, the polypeptides of the fusion protein can be in any order. Fusion polypeptides or fusion proteins can also include conservatively modified variants, polymorphic variants, alleles, mutants, subsequences, and interspecies homologs, so long as the desired activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as disclosed elsewhere herein.

Fusion polypeptides may optionally comprise a linker that can be used to link the one or more polypeptides or domains within a polypeptide. A peptide linker sequence may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. Linker sequences are not required when a particular fusion polypeptide segment contains non-essential N-terminal amino acid regions that can be used to separate the functional domains and prevent steric interference. Preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between.

Exemplary linkers include, but are not limited to the following amino acid sequences: glycine polymers $(G)_n$; glycine-serine polymers $(G_{1-5}S_{1-5})_n$, where n is an integer of at least one, two, three, four, or five; glycine-alanine polymers; alanine-serine polymers; GGG (SEQ ID NO: 21); DGGGS (SEQ ID NO: 22); TGEKP (SEQ ID NO: 23) (see e.g., Liu et al., *PNAS* 5525-5530 (1997)); GGRR (SEQ ID NO: 24) (Pomerantz et al. 1995, supra); $(GGGGS)_n$ wherein n=1, 2, 3, 4 or 5 (SEQ ID NO: 25) (Kim et al., PNAS 93, 1156-1160 (1996.); EGKSSGSGSESKVD (SEQ ID NO: 26) (Chaudhary et al., 1990, *Proc. Natl. Acad. Sci. U.S.A.* 87:1066-1070); KESGSVSSEQLAQFRSLD (SEQ ID NO: 27) (Bird et al., 1988, *Science* 242:423-426), GGRRGGGS (SEQ ID NO: 28); LRQRDGERP (SEQ ID NO: 29); LRQKDGGGSERP (SEQ ID NO: 30); LRQKD(GGGS)₂ ERP (SEQ ID NO: 31). Alternatively, flexible linkers can be rationally designed using a computer program capable of modeling both DNA-binding sites and the peptides themselves (Desjarlais & Berg, *PNAS* 90:2256-2260 (1993), PNAS 91:11099-11103 (1994) or by phage display methods.

Fusion polypeptides may further comprise a polypeptide cleavage signal between each of the polypeptide domains described herein or between an endogenous open reading frame and a polypeptide encoded by a donor repair template. In addition, a polypeptide cleavage site can be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic,* 5(8); 616-26).

Suitable protease cleavages sites and self-cleaving peptides are known to the skilled person (see, e.g., in Ryan et al., 1997. *J Gener. Virol.* 78, 699-722; Scymczak et al. (2004) Nature Biotech. 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded pro-
teases, aphthovirus L proteases, enterovirus 2A proteases,
rhinovirus 2A proteases, picorna 3C proteases, comovirus
24K proteases, nepovirus 24K proteases, RTSV (rice tungro
spherical virus) 3C-like protease, PYVF (parsnip yellow
fleck virus) 3C-like protease, heparin, thrombin, factor Xa
and enterokinase. Due to its high cleavage stringency, TEV
(tobacco etch virus) protease cleavage sites are preferred in
one embodiment, e.g., EXXYXQ(G/S) (SEQ ID NO: 32),
for example, ENLYFQG (SEQ ID NO: 33) and ENLYFQS
(SEQ ID NO: 34), wherein X represents any amino acid
(cleavage by TEV occurs between Q and G or Q and S).

In particular embodiments, the polypeptide cleavage sig-
nal is a viral self-cleaving peptide or ribosomal skipping
sequence.

Illustrative examples of ribosomal skipping sequences
include but are not limited to: a 2A or 2A-like site, sequence
or domain (Donnelly et al., 2001. *J. Gen. Virol.* 82:1027-
1041). In a particular embodiment, the viral 2A peptide is an
aphthovirus 2A peptide, a potyvirus 2A peptide, or a car-
diovirus 2A peptide.

In one embodiment, the viral 2A peptide is selected from
the group consisting of: a foot-and-mouth disease virus
(FMIDV) 2A peptide, an equine rhinitis A virus (ERAV) 2A
peptide, a Thosea asigna virus (TaV) 2A peptide, a porcine
teschovirus-1 (PTV-1) 2A peptide, a Theilovirus 2A peptide,
and an encephalomyocarditis virus 2A peptide.

Illustrative examples of 2A sites are provided in Table 2.

TABLE 2

| Exemplary 2A sites include the following sequences: |
| --- |
| SEQ ID NO: 35 | GSGATNFSLLKQAGDVEENPGP |
| SEQ ID NO: 36 | ATNFSLLKQAGDVEENPGP |
| SEQ ID NO: 37 | LLKQAGDVEENPGP |
| SEQ ID NO: 38 | GSGEGRGSLLTCGDVEENPGP |
| SEQ ID NO: 39 | EGRGSLLTCGDVEENPGP |
| SEQ ID NO: 40 | LLTCGDVEENPGP |
| SEQ ID NO: 41 | GSGQCTNYALLKLAGDVESNPGP |
| SEQ ID NO: 42 | QCTNYALLKLAGDVESNPGP |
| SEQ ID NO: 43 | LLKLAGDVESNPGP |
| SEQ ID NO: 44 | GSGVKQTLNFDLLKLAGDVESNPGP |
| SEQ ID NO: 45 | VKQTLNFDLLKLAGDVESNPGP |
| SEQ ID NO: 46 | LLKLAGDVESNPGP |
| SEQ ID NO: 47 | LLNFDLLKLAGDVESNPGP |
| SEQ ID NO: 48 | TLNFDLLKLAGDVESNPGP |
| SEQ ID NO: 49 | LLKLAGDVESNPGP |
| SEQ ID NO: 50 | NFDLLKLAGDVESNPGP |
| SEQ ID NO: 51 | QLLNFDLLKLAGDVESNPGP |
| SEQ ID NO: 52 | APVKQTLNFDLLKLAGDVESNPGP |
| SEQ ID NO: 53 | VTELLYRMKRAETYCPRPLLAIHPTEARHKQKIVAPVKQT |

TABLE 2-continued

| Exemplary 2A sites include the following sequences: |
| --- |
| SEQ ID NO: 54 | LNFDLLKLAGDVESNPGP |
| SEQ ID NO: 55 | LLAIHPTEARHKQKIVAPVKQTLNFDLLKLAGDVESNPGP |
| SEQ ID NO: 56 | EARHKQKIVAPVKQTLNFDLLKLAGDVESNPGP |

In preferred embodiments, a polypeptide comprises an
I-OnuI HE variant or megaTAL that binds and cleaves and
target site in the PDCD-1 gene and that further comprises
increased thermostability and/or enzymatic activity relative
to a parent enzyme.

G. Polynucleotides

In particular embodiments, polynucleotides encoding one
or more homing endonuclease variants and megaTALs engi-
neered to increase thermostability and/or enzymatic activity,
and fusion polypeptides contemplated herein are provided.
As used herein, the terms "polynucleotide" or "nucleic acid"
refer to deoxyribonucleic acid (DNA), ribonucleic acid
(RNA) and DNA/RNA hybrids. Polynucleotides may be
single-stranded or double-stranded and either recombinant,
synthetic, or isolated. Polynucleotides include, but are not
limited to: pre-messenger RNA (pre-mRNA), messenger
RNA (mRNA), RNA, short interfering RNA (siRNA), short
hairpin RNA (shRNA), microRNA (miRNA), ribozymes,
genomic RNA (gRNA), plus strand RNA (RNA(+)), minus
strand RNA (RNA(−)), tracrRNA, crRNA, single guide
RNA (sgRNA), synthetic RNA, synthetic mRNA, genomic
DNA (gDNA), PCR amplified DNA, complementary DNA
(cDNA), synthetic DNA, or recombinant DNA. Polynucle-
otides refer to a polymeric form of nucleotides of at least 5,
at least 10, at least 15, at least 20, at least 25, at least 30, at
least 40, at least 50, at least 100, at least 200, at least 300,
at least 400, at least 500, at least 1000, at least 5000, at least
10000, or at least 15000 or more nucleotides in length, either
ribonucleotides or deoxyribonucleotides or a modified form
of either type of nucleotide, as well as all intermediate
lengths. It will be readily understood that "intermediate
lengths," in this context, means any length between the
quoted values, such as 6, 7, 8, 9, etc., 101, 102, 103, etc.;
151, 152, 153, etc.; 201, 202, 203, etc. In particular embodi-
ments, polynucleotides or variants have at least or about
50%, 55%, 60%, 65%, 70%, 71%, 72%, 73%, 74%, 75%,
76%, 77%, 78%, 79%, 80%, 81%, 82%, 83%, 84%, 85%,
86%, 87%, 88%, 89%, 90%, 91%, 92%, 93%, 94%, 95%,
96%, 97%, 98%, 99% or 100% sequence identity to a
reference sequence.

In particular embodiments, polynucleotides may be
codon-optimized. As used herein, the term "codon-opti-
mized" refers to substituting codons in a polynucleotide
encoding a polypeptide in order to increase the expression,
stability and/or activity of the polypeptide. Factors that
influence codon optimization include, but are not limited to
one or more of: (i) variation of codon biases between two or
more organisms or genes or synthetically constructed bias
tables, (ii) variation in the degree of codon bias within an
organism, gene, or set of genes, (iii) systematic variation of
codons including context, (iv) variation of codons according
to their decoding tRNAs, (v) variation of codons according
to GC %, either overall or in one position of the triplet, (vi)
variation in degree of similarity to a reference sequence for
example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

As used herein the term "nucleotide" refers to a heterocyclic nitrogenous base in N-glycosidic linkage with a phosphorylated sugar. Nucleotides are understood to include natural bases, and a wide variety of art-recognized modified bases. Such bases are generally located at the 1' position of a nucleotide sugar moiety. Nucleotides generally comprise a base, sugar and a phosphate group. In ribonucleic acid (RNA), the sugar is a ribose, and in deoxyribonucleic acid (DNA) the sugar is a deoxyribose, i.e., a sugar lacking a hydroxyl group that is present in ribose. Exemplary natural nitrogenous bases include the purines, adenosine (A) and guanidine (G), and the pyrimidines, cytidine (C) and thymidine (T) (or in the context of RNA, uracil (U)). The C-1 atom of deoxyribose is bonded to N-1 of a pyrimidine or N-9 of a purine. Nucleotides are usually mono, di- or triphosphates. The nucleotides can be unmodified or modified at the sugar, phosphate and/or base moiety, (also referred to interchangeably as nucleotide analogs, nucleotide derivatives, modified nucleotides, non-natural nucleotides, and non-standard nucleotides; see for example, WO 92/07065 and WO 93/15187). Examples of modified nucleic acid bases are summarized by Limbach et al., (1994, *Nucleic Acids Res.* 22, 2183-2196).

A nucleotide may also be regarded as a phosphate ester of a nucleoside, with esterification occurring on the hydroxyl group attached to C-5 of the sugar. As used herein, the term "nucleoside" refers to a heterocyclic nitrogenous base in N-glycosidic linkage with a sugar. Nucleosides are recognized in the art to include natural bases, and also to include well known modified bases. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, nucleoside derivatives, modified nucleosides, non-natural nucleosides, or non-standard nucleosides). As also noted above, examples of modified nucleic acid bases are summarized by Limbach et al., (1994, *Nucleic Acids Res.* 22, 2183-2196).

Illustrative examples of polynucleotides include but are not limited to polynucleotides encoding SEQ ID NOs: 6 and 7, and polynucleotide sequences set forth in SEQ ID NOs: 11 and 12.

In various illustrative embodiments, polynucleotides contemplated herein include, but are not limited to polynucleotides encoding homing endonuclease variants, megaTALs, end-processing enzymes, fusion polypeptides, and expression vectors, viral vectors, and transfer plasmids comprising polynucleotides contemplated herein.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide.

In one embodiment, a polynucleotide comprises a nucleotide sequence that hybridizes to a target nucleic acid sequence under stringent conditions. To hybridize under "stringent conditions" describes hybridization protocols in which nucleotide sequences at least 60% identical to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., *Current Protocols in Molecular Biology*, John Wiley & Sons Inc., 1994-1998, Chapter 15.

An "isolated polynucleotide," as used herein, refers to a polynucleotide that has been purified from the sequences which flank it in a naturally-occurring state, e.g., a DNA fragment that has been removed from the sequences that are normally adjacent to the fragment. In particular embodiments, an "isolated polynucleotide" refers to a complementary DNA (cDNA), a recombinant polynucleotide, a synthetic polynucleotide, or other polynucleotide that does not exist in nature and that has been made by the hand of man. In particular embodiments, an isolated polynucleotide is a synthetic polynucleotide, a semi-synthetic polynucleotide, or a polynucleotide obtained or derived from a recombinant source.

In various embodiments, a polynucleotide comprises an mRNA encoding a polypeptide contemplated herein including, but not limited to, a homing endonuclease variant, a megaTAL, and an end-processing enzyme. In certain embodiments, the mRNA comprises a cap, one or more nucleotides, and a poly(A) tail.

As used herein, the terms "5' cap" or "5' cap structure" or "5' cap moiety" refer to a chemical modification, which has been incorporated at the 5' end of an mRNA. The 5' cap is involved in nuclear export, mRNA stability, and translation.

In particular embodiments, a mRNA contemplated herein comprises a 5' cap comprising a 5'-ppp-5'-triphosphate linkage between a terminal guanosine cap residue and the 5'-terminal transcribed sense nucleotide of the mRNA molecule. This 5'-guanylate cap may then be methylated to generate an N7-methyl-guanylate residue.

Illustrative examples of 5' cap suitable for use in particular embodiments of the mRNA polynucleotides contemplated herein include, but are not limited to: unmethylated 5' cap analogs, e.g., G(5')ppp(5')G, G(5')ppp(5')C, G(5')ppp(5')A; methylated 5' cap analogs, e.g., m$^7$G(5')ppp(5')G, m$^7$G(5')ppp(5')C, and m$^7$G(5')ppp(5')A; dimethylated 5' cap analogs, e.g., m$^{2,7}$G(5')ppp(5')G, m$^{2,7}$G(5')ppp(5')C, and m$^{2,7}$G(5')ppp(5')A; trimethylated 5' cap analogs, e.g., m$^{2,2,7}$G(5')ppp(5')G, m$^{2,2,7}$G(5')ppp(5')C, and m$^{2,2,7}$G(5')ppp(5')A; dimethylated symmetrical 5' cap analogs, e.g., m$^7$G(5')pppm$^7$(5')G, m$^7$G(5')pppm$^7$(5')C, and m$^7$G(5')pppm$^7$(5')A; and anti-reverse 5' cap analogs, e.g., Anti-Reverse Cap Analog (ARCA) cap, designated 3'O-Me-m$^7$G(5')ppp(5')G, 2'O-Me-m$^7$G(5')ppp(5')G, 2'O-Me-m$^7$G(5')ppp(5')C, 2'O-Me-m$^7$G(5')ppp(5')A, m$^7$2'd(5')ppp(5')G, m$^7$2'd(5')ppp(5')C, m$^7$2'd(5')ppp(5')A, 3'O-Me-m$^7$G(5')ppp(5')C, 3'O-Me-m$^7$G(5')ppp(5')A, m$^7$3'd(5')ppp(5')G, m$^7$3'd(5')ppp(5')C, m$^7$3'd(5')ppp(5')A and their tetraphosphate derivatives) (see, e.g., Jemielity et al., RNA, 9: 1108-1122 (2003)).

In particular embodiments, mRNAs comprise a 5' cap that is a 7-methyl guanylate ("m$^7$G") linked via a triphosphate bridge to the 5'-end of the first transcribed nucleotide, resulting in m$^7$G(5')ppp(5')N, where N is any nucleoside.

In some embodiments, mRNAs comprise a 5' cap wherein the cap is a Cap0 structure (Cap0 structures lack a 2'-O-methyl residue of the ribose attached to bases 1 and 2), a Cap1 structure (Cap1 structures have a 2'-O-methyl residue at base 2), or a Cap2 structure (Cap2 structures have a 2'-O-methyl residue attached to both bases 2 and 3).

In one embodiment, an mRNA comprises a m$^7$G(5')ppp(5')G cap.

In one embodiment, an mRNA comprises an ARCA cap.

In particular embodiments, an mRNA contemplated herein comprises one or more modified nucleosides.

In one embodiment, an mRNA comprises one or more modified nucleosides selected from the group consisting of pseudouridine, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyl-adenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methyl-guanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In one embodiment, an mRNA comprises one or more modified nucleosides selected from the group consisting of pseudouridine, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methylpseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In one embodiment, an mRNA comprises one or more modified nucleosides selected from the group consisting of 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In one embodiment, an mRNA comprises one or more modified nucleosides selected from the group consisting of: 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In one embodiment, an mRNA comprises one or more modified nucleosides selected from the group consisting of inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In one embodiment, an mRNA comprises one or more pseudouridines, one or more 5-methyl-cytosines, and/or one or more 5-methyl-cytidines.

In one embodiment, an mRNA comprises one or more pseudouridines.

In one embodiment, an mRNA comprises one or more 5-methyl-cytidines.

In one embodiment, an mRNA comprises one or more 5-methyl-cytosines.

In particular embodiments, an mRNA contemplated herein comprises a poly(A) tail to help protect the mRNA from exonuclease degradation, stabilize the mRNA, and facilitate translation. In certain embodiments, an mRNA comprises a 3' poly(A) tail structure.

In particular embodiments, the length of the poly(A) tail is at least about 10, 25, 50, 75, 100, 150, 200, 250, 300, 350, 400, 450, or at least about 500 or more adenine nucleotides or any intervening number of adenine nucleotides. In particular embodiments, the length of the poly(A) tail is at least about 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 202, 203, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, or 275 or more adenine nucleotides.

In particular embodiments, the length of the poly(A) tail is about 10 to about 500 adenine nucleotides, about 50 to about 500 adenine nucleotides, about 100 to about 500 adenine nucleotides, about 150 to about 500 adenine nucleotides, about 200 to about 500 adenine nucleotides, about 250 to about 500 adenine nucleotides, about 300 to about 500 adenine nucleotides, about 50 to about 450 adenine nucleotides, about 50 to about 400 adenine nucleotides, about 50 to about 350 adenine nucleotides, about 100 to about 500 adenine nucleotides, about 100 to about 450 adenine nucleotides, about 100 to about 400 adenine nucleotides, about 100 to about 350 adenine nucleotides, about 100 to about 300 adenine nucleotides, about 150 to about 500 adenine nucleotides, about 150 to about 450 adenine nucleotides, about 150 to about 400 adenine nucleotides, about 150 to about 350 adenine nucleotides, about 150 to about 300 adenine nucleotides, about 150 to about 250 adenine nucleotides, about 150 to about 200 adenine nucleotides, about 200 to about 500 adenine nucleotides, about 200 to about 450 adenine nucleotides, about 200 to about 400 adenine nucleotides, about 200 to about 350 adenine nucleotides, about 200 to about 300 adenine nucleotides, about 250 to about 500 adenine nucleotides, about 250 to about 450 adenine nucleotides, about 250 to about 400 adenine nucleotides, about 250 to about 350 adenine nucleotides, or about 250 to about 300 adenine nucleotides or any intervening range of adenine nucleotides.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the pre-messenger (pre-mRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' A G T C A T G 3' is 3' T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

The term "nucleic acid cassette" or "expression cassette" as used herein refers to genetic sequences within the vector which can express an RNA, and subsequently a polypeptide. In one embodiment, the nucleic acid cassette contains a gene(s)-of-interest, e.g., a polynucleotide(s)-of-interest. In another embodiment, the nucleic acid cassette contains one or more expression control sequences, e.g., a promoter, enhancer, poly(A) sequence, and a gene(s)-of-interest, e.g., a polynucleotide(s)-of-interest. Vectors may comprise 1, 2, 3, 4, 5, 6, 7, 8, 9 or 10 or more nucleic acid cassettes. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In a preferred embodiment, the nucleic acid cassette contains the sequence of a therapeutic gene used to treat, prevent, or ameliorate a genetic disorder. The cassette can be removed and inserted into a plasmid or viral vector as a single unit.

Polynucleotides include polynucleotide(s)-of-interest. As used herein, the term "polynucleotide-of-interest" refers to a polynucleotide encoding a polypeptide or fusion polypeptide or a polynucleotide that serves as a template for the transcription of an inhibitory polynucleotide, as contemplated herein.

Moreover, it will be appreciated by those of ordinary skill in the art that, as a result of the degeneracy of the genetic code, there are many nucleotide sequences that may encode a polypeptide, or fragment of variant thereof, as contemplated herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. In one embodiment, polynucleotides comprising particular allelic sequences are provided. Alleles are endogenous polynucleotide sequences that are altered as a result of one or more mutations, such as deletions, additions and/or substitutions of nucleotides.

In a certain embodiment, a polynucleotide-of-interest comprises a donor repair template.

In a certain embodiment, a polynucleotide-of-interest comprises an inhibitory polynucleotide including, but not limited to, an siRNA, an miRNA, an shRNA, a ribozyme or another inhibitory RNA.

In one embodiment, a donor repair template comprising an inhibitory RNA comprises one or more regulatory sequences, such as, for example, a strong constitutive pol III, e.g., human or mouse U6 snRNA promoter, the human and mouse H1 RNA promoter, or the human tRNA-val promoter, or a strong constitutive pol II promoter, as described elsewhere herein.

The polynucleotides contemplated in particular embodiments, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, post-transcription response elements, and polynucleotides encoding self-cleaving polypeptides, epitope tags, as disclosed elsewhere herein or as known in the art, such that their overall length may vary considerably. It is therefore contemplated in particular embodiments that a polynucleotide fragment of almost any length may be employed, with the total length preferably being limited by the ease of preparation and use in the intended recombinant DNA protocol.

Polynucleotides can be prepared, manipulated, expressed and/or delivered using any of a variety of well-established techniques known and available in the art. In order to express a desired polypeptide, a nucleotide sequence encoding the polypeptide, can be inserted into appropriate vector. A desired polypeptide can also be expressed by delivering an mRNA encoding the polypeptide into the cell.

Illustrative examples of vectors include, but are not limited to plasmid, autonomously replicating sequences, and transposable elements, e.g., Sleeping Beauty, PiggyBac.

Additional illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include but are not limited to pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally.

"Expression control sequences," "control elements," or "regulatory sequences" present in an expression vector are those non-translated regions of the vector including but not limited to an origin of replication, selection cassettes, promoters, enhancers, translation initiation signals (Shine Dalgarno sequence or Kozak sequence) introns, post-transcriptional regulatory elements, a polyadenylation sequence, 5' and 3' untranslated regions, which interact with host cellular proteins to carry out transcription and translation. Such elements may vary in their strength and specificity. Depending on the vector system and host utilized, any number of suitable transcription and translation elements, including ubiquitous promoters and inducible promoters may be used.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is an ideal polyA sequence (e.g., AATAAA, ATTAAA, AGTAAA). In particular embodiments, the poly(A) sequence is an SV40 polyA sequence, a bovine growth hormone polyA sequence (BGHpA), a rabbit β-globin polyA sequence (rβgpA), variants thereof, or another suitable heterologous or endogenous polyA sequence known in the art. In particular embodiments, the poly(A) sequence is synthetic.

In particular embodiments, polynucleotides encoding one or more nuclease variants, megaTALs, end-processing enzymes, or fusion polypeptides may be introduced into hematopoietic cells, e.g., T cells, by both non-viral and viral methods. In particular embodiments, delivery of one or more polynucleotides encoding nucleases and/or donor repair templates may be provided by the same method or by different methods, and/or by the same vector or by different vectors.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. In particular embodiments, non-viral vectors are used to deliver one or more polynucleotides contemplated herein to a T cell.

Illustrative examples of non-viral vectors include, but are not limited to plasmids (e.g., DNA plasmids or RNA plasmids), transposons, cosmids, and bacterial artificial chromosomes.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

Illustrative examples of viral vector systems suitable for use in particular embodiments contemplated herein include, but are not limited to adeno-associated virus (AAV), retrovirus, herpes simplex virus, adenovirus, and vaccinia virus vectors.

H. Compositions and Formulations

The compositions contemplated in particular embodiments may comprise one or more homing endonuclease variants and megaTALs engineered to increase thermostability and/or enzymatic activity, polynucleotides, vectors comprising same, and genome editing compositions and genome edited cell compositions, as contemplated herein. The genome editing compositions and methods contemplated in particular embodiments are useful for editing a target site in the human program cell death 1 (PDCD-1) gene in a cell or a population of cells. In preferred embodiments, a genome editing composition is used to edit a PDCD-1 gene in a hematopoietic cell, e.g., a T cell or an immune effector cell.

In various embodiments, the compositions contemplated herein comprise I-OnuI HE variant engineered to increase thermostability and/or enzymatic activity, and optionally an end-processing enzyme, e.g., a 3'-5' exonuclease (Trex2). The I-OnuI HE variant may be in the form of an mRNA that is introduced into a cell via polynucleotide delivery methods disclosed supra, e.g., electroporation, lipid nanoparticles, etc. In one embodiment, a composition comprising an mRNA encoding an I-OnuI HE variant or megaTAL, and optionally a 3'-5' exonuclease, is introduced in a cell via polynucleotide delivery methods disclosed supra. The composition may be used to generate a genome edited cell or population of genome edited cells by error prone NHEJ.

In various embodiments, the compositions contemplated herein comprise a donor repair template. The composition may be delivered to a cell that expresses or will express an I-OnuI HE variant, and optionally an end-processing enzyme. In one embodiment, the composition may be delivered to a cell that expresses or will express an I-OnuI HE variant or megaTAL, and optionally a 3'-5' exonuclease. Expression of the gene editing enzymes in the presence of the donor repair template can be used to generate a genome edited cell or population of genome edited cells by HDR.

In particular embodiments, a composition comprises a cell containing one or more homing endonuclease variants and megaTALs engineered to increase thermostability and/or enzymatic activity, polynucleotides, vectors comprising same. In particular embodiments, the cells may be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are obtained from a mammalian subject. In a more preferred embodiment, the cells are obtained from a primate subject, optionally a non-human primate. In the most preferred embodiment, the cells are obtained from a human subject.

An "isolated cell" refers to a non-naturally occurring cell, e.g., a cell that does not exist in nature, a modified cell, an engineered cell, a recombinant cell etc., that has been obtained from an in vivo tissue or organ and is substantially free of extracellular matrix.

As used herein, the term "population of cells" refers to a plurality of cells that may be made up of any number and/or combination of homogenous or heterogeneous cell types.

In preferred embodiments, the cell or population of cells are hematopoietic cells, more preferably immune cells, and even more preferably T cells.

The terms "T cell" or "T lymphocyte" are art-recognized and are intended to include thymocytes, immune effector cells, regulatory T cells, naïve T lymphocytes, immature T lymphocytes, mature T lymphocytes, resting T lymphocytes, or activated T lymphocytes. A T cell can be a T helper (Th)

cell, for example a T helper 1 (Th1) or a T helper 2 (Th2) cell. The T cell can be a helper T cell (HTL; CD4$^+$ T cell) CD4$^+$ T cell, a cytotoxic T cell (CTL; CD8$^+$ T cell), a tumor infiltrating cytotoxic T cell (TIL; CD8$^+$ T cell), CD4$^+$CD8$^+$ T cell, CD4$^-$CD8$^-$ T cell, or any other subset of T cells. In one embodiment, the T cell is an immune effector cell. In one embodiment, the T cell is an NKT cell. Other illustrative populations of T cells suitable for use in particular embodiments include naïve T cells and memory T cells.

In various embodiments, a cell or population of cells comprises immune effector cells. An "immune effector cell," is any cell of the immune system that has one or more effector functions (e.g., cytotoxic cell killing activity, secretion of cytokines, induction of ADCC and/or CDC). Illustrative immune effector cells contemplated in particular embodiments are T lymphocytes, in particular cytotoxic T cells (CTLs; CD8$^+$ T cells), TILs, and helper T cells (HTLs; CD4$^+$ T cells). In one embodiment, immune effector cells include natural killer (NK) cells. In one embodiment, immune effector cells include natural killer T (NKIT) cells.

T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors.

In particular embodiments, the compositions contemplated herein comprise a population of cells, an I-OnuI HE variant, and optionally, a donor repair template. In particular embodiments, the compositions contemplated herein comprise a population of cells, an I-OnuI HE variant, an end-processing enzyme, and optionally, a donor repair template. The I-OnuI HE and/or end-processing enzyme may be in the form of an mRNA that is introduced into the cell via polynucleotide delivery methods disclosed supra.

In particular embodiments, the compositions contemplated herein comprise a population of cells, an I-OnuI HE variant or megaTAL engineered to increase thermostability and/or activity of the enzyme, and optionally, a donor repair template. In particular embodiments, the compositions contemplated herein comprise a population of cells, an I-OnuI HE variant or megaTAL, a 3'-5' exonuclease, and optionally, a donor repair template. The I-OnuI HE variant, megaTAL, and/or 3'-5' exonuclease may be in the form of an mRNA that is introduced into the cell via polynucleotide delivery methods disclosed supra.

In particular embodiments, the population of cells comprise genetically modified immune effector cells.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Reprogramming an I-ONUI HE Variant to Increase Thermostability

Figure 1B:
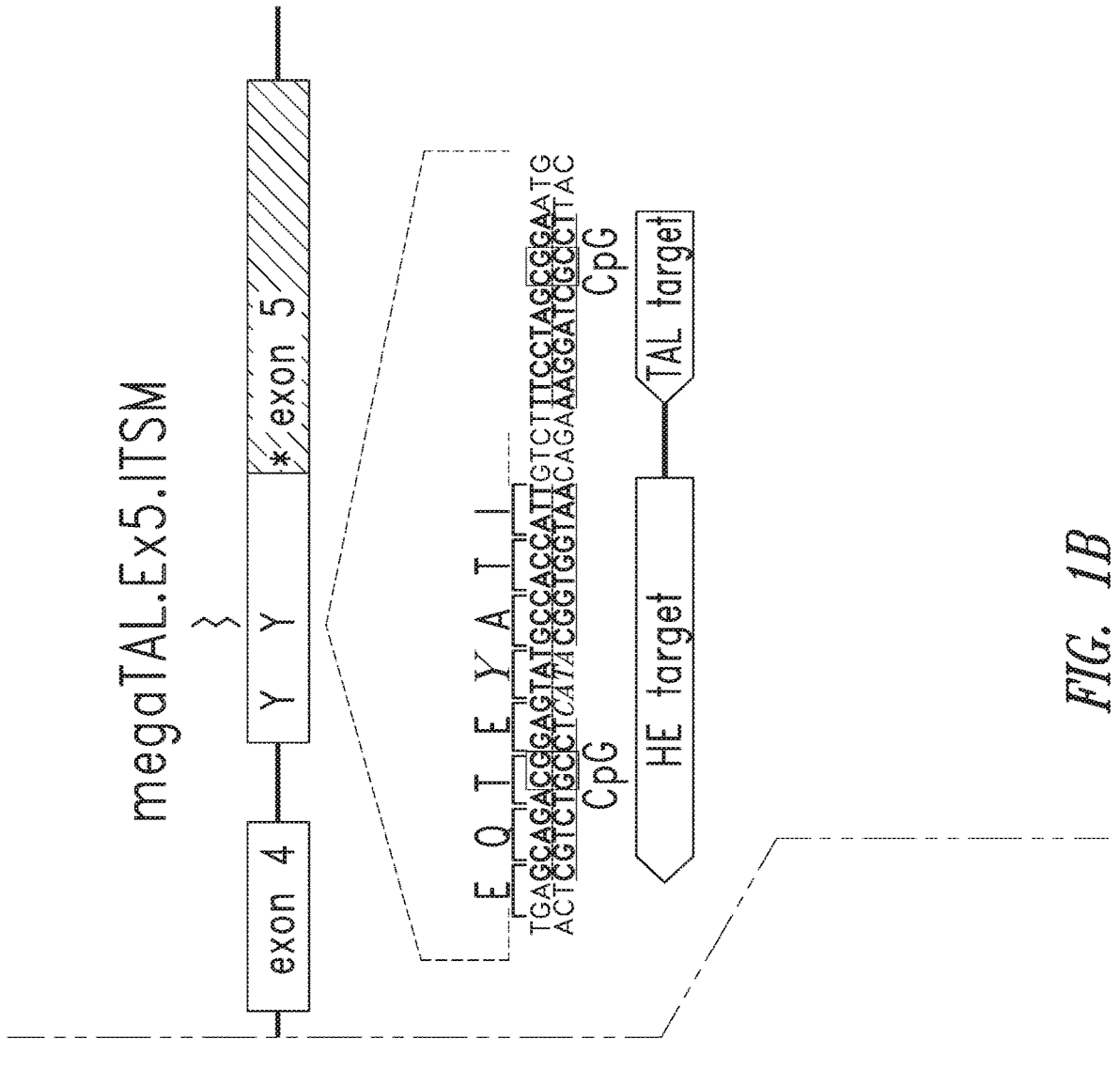
FIG. 1B show the PDCD-1 gene and the location of the target sites in exon 5 (SEQ ID NO: 63, 64, and 65).

PDCD-1 is expressed on the T cell plasma membrane following antigen receptor stimulation and activation. PDCD-1 comprises a signal peptide, an extracellular IgV-like domain, a transmembrane spanning domain, and an intracellular tail that contains both an immunoreceptor tyrosine-based inhibition motif (ITIM, consensus sequence S/I/V/LxYxxI/V/L) and an immunoreceptor tyrosine-based switch motif (ITSM, consensus sequence TxYxxV/I). FIGS. 1A and 1B.

Figure 2:
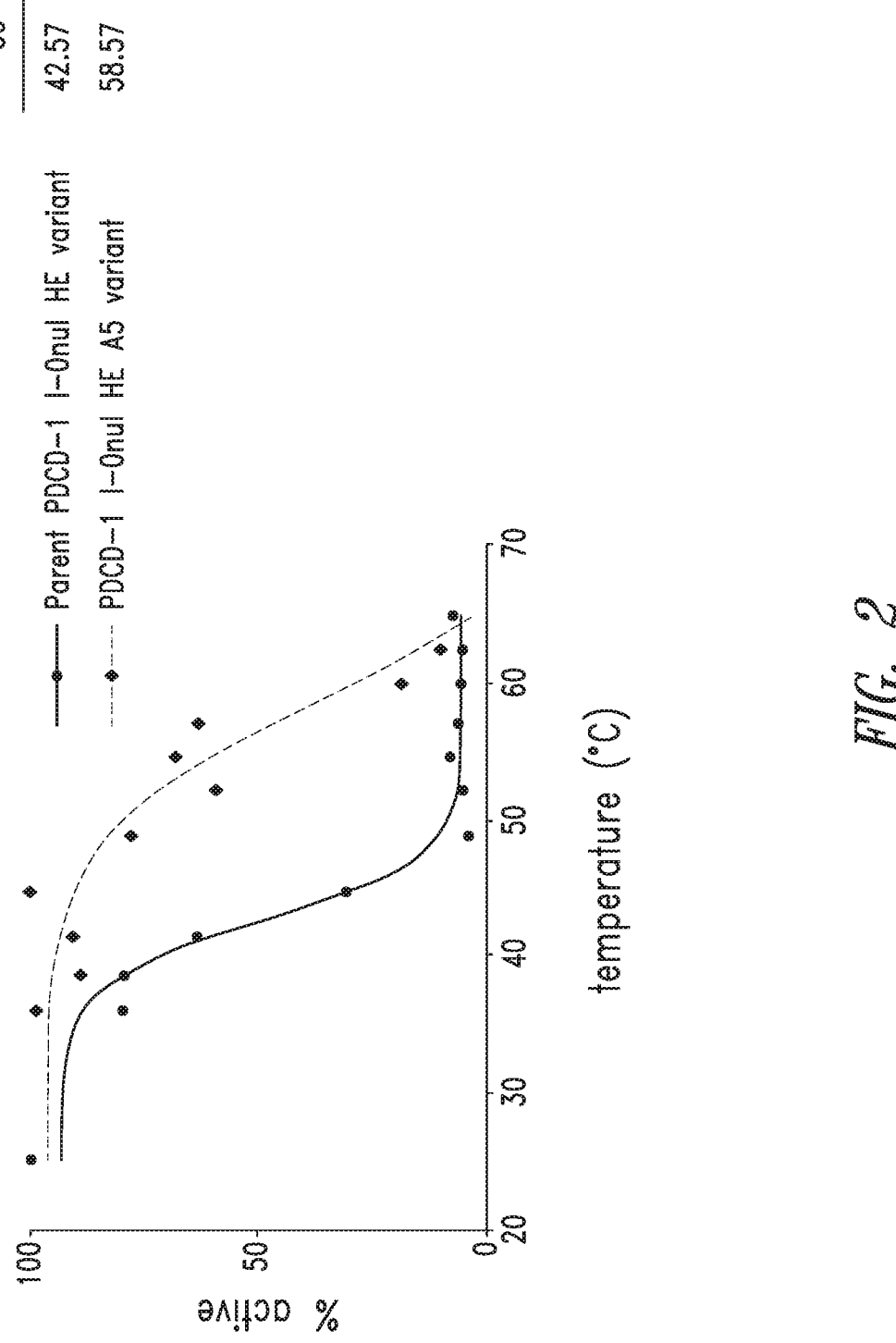
FIG. 2 shows that introducing stabilizing mutations into a PDCD-1 HE variant increases the thermostability of the enzyme compared to the parent PDCD-1 HE variant.

A yeast surface display assay was used to identify mutations that increase the stability of I-OnuI HEs. Multiple I-OnuI HEs were subjected to random mutagenesis via PCR over the full open reading frame. These mutant libraries were expressed in yeast and sorted for active nuclease activity after heat shock at or above the TM$_{50}$ of the library. After two sorts, I-OnuI HE variants were sequenced with either PacBio or Sanger sequencing to determine the identity and frequency of mutations at each position. The mutations were grafted to an I-OnuI HE variant that targets exon 1 of the PDCD-1 gene. The thermostable mutations increased the TM$_{50}$ of a PDCD-1 I-OnuI HE variant by 16° C. compared to the parent enzyme (FIG. 2).

The effects of the stabilizing mutations on PDCD-1 editing was measured by comparing editing rates of a parental megaTAL that lacks the stabilizing mutations (SEQ ID NO: 18) with a megaTAL comprising the stabilizing mutations (SEQ ID NO: 7). megaTAL mRNA was prepared by in vitro transcription, co-transcriptionally capped with Anti-Reverse Cap Analog (ARCA) and enzymatically polyadenylated with poly(A) polymerase. Purified mRNA was used to measure PDCD-1 editing efficiency in primary human T cells.

Figure 3:
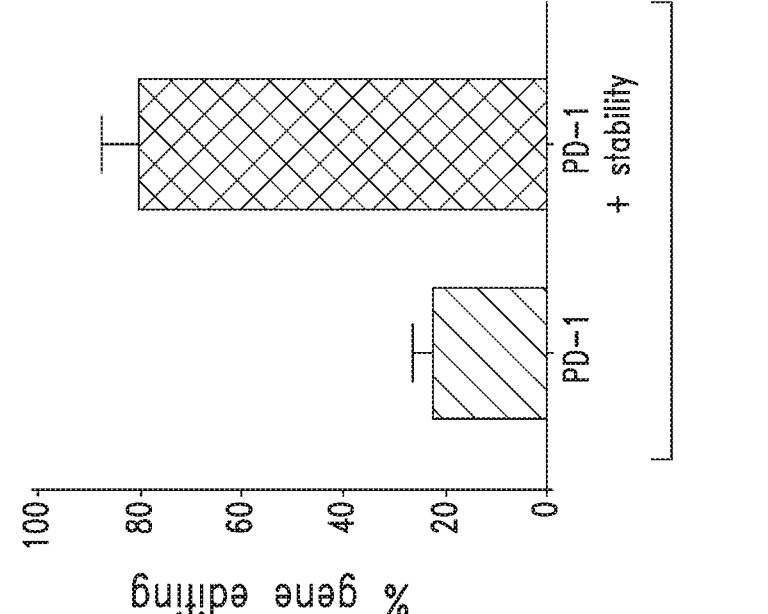
FIG. 3 shows that increasing thermostability of a PDCD-1 megaTAL significantly increases editing activity compared to its parent PDCD-1 megaTAL.

Primary human peripheral blood mononuclear cells (PBMCs) from two donors were activated with anti-CD3 and anti-CD28 antibodies and cultured in the presence of 250 U/mL IL-2. At 3 days post-activation cells were electroporated with megaTAL mRNA. Transfected T cells were expanded for an additional 7-10 days and editing efficiency was measured using sequencing across the PD-1 target site and Tracking of Indels by Decomposition (TIDE, see Brinkman et al., 2014) (FIG. 3). Without the stabilizing mutations, the PDCD-1 megaTAL showed low levels of editing (<20%); the stabilized PDCD-1 megaTAL increased editing activity to nearly 80%.

In general, in the following claims, the terms used should not be construed to limit the claims to the specific embodiments disclosed in the specification and the claims but should be construed to include all possible embodiments along with the full scope of equivalents to which such claims are entitled. Accordingly, the claims are not limited by the disclosure

---

What is claimed is:

1. A polypeptide comprising an I-OnuI homing endonuclease (HE) variant, wherein the polypeptide comprises an amino acid sequence at least 98% identical to the amino acid sequence set forth in SEQ ID NO: 6.

2. The polypeptide of claim 1, wherein the polypeptide comprises the amino acid sequence set forth in SEQ ID NO: 6.

3. The polypeptide of claim 1, wherein the polypeptide binds and cleaves a target site in the human programmed cell death 1 (PDCD-1) gene, and wherein the target site is SEQ ID NO: 8.

4. The polypeptide of claim 2, wherein the polypeptide binds and cleaves a target site in the human programmed cell death 1 (PDCD-1) gene, and wherein the target site is SEQ ID NO: 8.

5. The polypeptide of claim 1, further comprising a TALE DNA binding domain, wherein the polypeptide binds and cleaves a target site in the human PDCD-1 gene, wherein the target site is SEQ ID NO: 10.

6. The polypeptide of claim 5, wherein the TALE DNA binding domain comprises about 9.5 TALE repeat units to about 15.5 TALE repeat units.

7. The polypeptide of claim 5, wherein the TALE DNA binding domain binds the polynucleotide sequence set forth in SEQ ID NO: 9.

8. The polypeptide of claim 5, wherein the I-OnuI HE variant comprises the amino acid sequence set forth in SEQ ID NO: 6.

9. The polypeptide of claim 5, wherein the polypeptide comprises an amino acid sequence at least 98% identical to the amino acid sequence set forth in SEQ ID NO: 7.

10. The polypeptide of claim 9, wherein the polypeptide comprises the amino acid sequence set forth in SEQ ID NO: 7.

11. The polypeptide of claim 1, wherein the I-OnuI HE variant comprises the following amino acid residues: 14T, 26G, 28S, 30L, 32R, 34R, 35G, 36T, 37A, 38R, 40H, 42R, 44S, 46T, 48M, 68S, 70L, 72N, 75H, 76Y, 80V, 82Y, 83A, 138M, 143N, 153V, 156R, 159P, 168G, 178D, 180S, 184R, 186R, 189N, 190V, 191N, 192A, 193R, 195R, 201E, 203S, 207R, 223H, 225Y, 227G, 232R, 236Q, 238R, 240E, 261M, and 300R in relation to the amino acid sequence set forth in SEQ ID NO: 6.

12. The polypeptide of claim 11, wherein the polypeptide comprises an amino acid sequence at least 99% identical to the amino acid sequence set forth in SEQ ID NO: 6.

13. The polypeptide of claim 11, wherein the polypeptide binds and cleaves a target site in the human programmed cell death 1 (PDCD-1) gene, and wherein the target site is SEQ ID NO: 8.

14. The polypeptide of claim 11, further comprising a TALE DNA binding domain.

15. The polypeptide of claim 14, wherein the polypeptide comprises an amino acid sequence at least 98% identical to the amino acid sequence set forth in SEQ ID NO: 7.

16. The polypeptide of claim 14, wherein the polypeptide comprises the amino acid sequence set forth in SEQ ID NO: 7.

17. The polypeptide of claim 14, wherein the polypeptide binds and cleaves a target site in the human PDCD-1 gene, wherein the target site is SEQ ID NO: 10.

18. The polypeptide of claim 1, wherein the polypeptide comprises an amino acid sequence at least 99% identical to the amino acid sequence set forth in SEQ ID NO: 6.

* * * * *

SEQUENCE LISTING

<160> NUMBER OF SEQ ID NOS: 65

<210> SEQ ID NO 1

```
<211> LENGTH: 303
<212> TYPE: PRT
<213> ORGANISM: Ophiostoma novo-ulmi

<400> SEQUENCE: 1

Met Ala Tyr Met Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
        35                  40                  45

Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Met Leu Phe Lys Gln
            100                 105                 110

Ala Phe Cys Val Met Glu Asn Lys Glu His Leu Lys Ile Asn Gly Ile
            115                 120                 125

Lys Glu Leu Val Arg Ile Lys Ala Lys Leu Asn Trp Gly Leu Thr Asp
    130                 135                 140

Glu Leu Lys Lys Ala Phe Pro Glu Ile Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
            180                 185                 190

Gly Val Gln Val Gln Leu Val Phe Ser Ile Thr Gln His Ile Lys Asp
        195                 200                 205

Lys Asn Leu Met Asn Ser Leu Ile Thr Tyr Leu Gly Cys Gly Tyr Ile
    210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Val Phe
    290                 295                 300

<210> SEQ ID NO 2
<211> LENGTH: 303
<212> TYPE: PRT
<213> ORGANISM: Ophiostoma novo-ulmi

<400> SEQUENCE: 2

Met Ala Tyr Met Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
        35                  40                  45
```

```
Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Leu Asn Trp Gly Leu Thr Asp
    130                 135                 140

Glu Leu Lys Lys Ala Phe Pro Glu Asn Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
            180                 185                 190

Gly Val Gln Val Gln Leu Val Phe Ser Ile Thr Gln His Ile Lys Asp
        195                 200                 205

Lys Asn Leu Met Asn Ser Leu Ile Thr Tyr Leu Gly Cys Gly Tyr Ile
    210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Val Phe
    290                 295                 300
```

<210> SEQ ID NO 3
<211> LENGTH: 303
<212> TYPE: PRT
<213> ORGANISM: Ophiostoma novo-ulmi
<220> FEATURE:
<221> NAME/KEY: MOD_RES
<222> LOCATION: (1)..(3)
<223> OTHER INFORMATION: Any amino acid or absent

<400> SEQUENCE: 3

```
Xaa Xaa Xaa Met Ser Arg Arg Glu Ser Ile Asn Pro Trp Ile Leu Thr
1                   5                   10                  15

Gly Phe Ala Asp Ala Glu Gly Ser Phe Leu Leu Arg Ile Arg Asn Asn
                20                  25                  30

Asn Lys Ser Ser Val Gly Tyr Ser Thr Glu Leu Gly Phe Gln Ile Thr
            35                  40                  45

Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95
```

```
Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
            115                 120                 125

Lys Glu Leu Val Arg Ile Lys Ala Lys Leu Asn Trp Gly Leu Thr Asp
    130                 135                 140

Glu Leu Lys Lys Ala Phe Pro Glu Asn Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
            180                 185                 190

Gly Val Gln Val Gln Leu Val Phe Ser Ile Thr Gln His Ile Lys Asp
            195                 200                 205

Lys Asn Leu Met Asn Ser Leu Ile Thr Tyr Leu Gly Cys Gly Tyr Ile
    210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
            275                 280                 285

Glu Ile Lys Lys Ile Lys Leu Asn Met Asn Lys Gly Arg Val Phe
    290                 295                 300
```

```
<210> SEQ ID NO 4
<211> LENGTH: 303
<212> TYPE: PRT
<213> ORGANISM: Ophiostoma novo-ulmi
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (302)..(303)
<223> OTHER INFORMATION: Any amino acid or absent

<400> SEQUENCE: 4
```

```
Xaa Xaa Xaa Xaa Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
            35                  40                  45

Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
            115                 120                 125
```

```
Lys Glu Leu Val Arg Ile Lys Ala Lys Leu Asn Trp Gly Leu Thr Asp
    130             135             140

Glu Leu Lys Lys Ala Phe Pro Glu Asn Ile Ser Lys Glu Arg Ser Leu
145             150             155             160

Ile Asn Lys Asn Ile Pro Asn Phe Lys Trp Leu Ala Gly Phe Thr Ser
            165             170             175

Gly Glu Gly Cys Phe Phe Val Asn Leu Ile Lys Ser Lys Ser Lys Leu
            180             185             190

Gly Val Gln Val Gln Leu Val Phe Ser Ile Thr Gln His Ile Lys Asp
            195             200             205

Lys Asn Leu Met Asn Ser Leu Ile Thr Tyr Leu Gly Cys Gly Tyr Ile
    210             215             220

Lys Glu Lys Asn Lys Ser Glu Phe Ser Trp Leu Asp Phe Val Val Thr
225             230             235             240

Lys Phe Ser Asp Ile Asn Asp Lys Ile Ile Pro Val Phe Gln Glu Asn
            245             250             255

Thr Leu Ile Gly Val Lys Leu Glu Asp Phe Gly Asp Trp Cys Lys Val
            260             265             270

Ala Lys Leu Ile Glu Glu Lys Lys His Leu Thr Glu Ser Gly Leu Asp
    275             280             285

Glu Ile Lys Lys Ile Lys Leu Asn Met Asn Lys Gly Arg Xaa Xaa
    290             295             300

<210> SEQ ID NO 5
<211> LENGTH: 303
<212> TYPE: PRT
<213> ORGANISM: Ophiostoma novo-ulmi
<220> FEATURE:
<221> NAME/KEY: MOD_RES
<222> LOCATION: (1)..(8)
<223> OTHER INFORMATION: Any amino acid or absent
<220> FEATURE:
<221> NAME/KEY: MOD_RES
<222> LOCATION: (302)..(303)
<223> OTHER INFORMATION: Any amino acid or absent

<400> SEQUENCE: 5

Xaa Xaa Xaa Xaa Xaa Xaa Xaa Xaa Ser Ile Asn Pro Trp Ile Leu Thr
1               5               10              15

Gly Phe Ala Asp Ala Glu Gly Ser Phe Leu Leu Arg Ile Arg Asn Asn
            20              25              30

Asn Lys Ser Ser Val Gly Tyr Ser Thr Glu Leu Gly Phe Gln Ile Thr
        35              40              45

Leu His Asn Lys Asp Lys Ser Ile Leu Glu Asn Ile Gln Ser Thr Trp
    50              55              60

Lys Val Gly Val Ile Ala Asn Ser Gly Asp Asn Ala Val Ser Leu Lys
65              70              75              80

Val Thr Arg Phe Glu Asp Leu Lys Val Ile Ile Asp His Phe Glu Lys
            85              90              95

Tyr Pro Leu Ile Thr Gln Lys Leu Gly Asp Tyr Lys Leu Phe Lys Gln
            100             105             110

Ala Phe Ser Val Met Glu Asn Lys Glu His Leu Lys Glu Asn Gly Ile
        115             120             125

Lys Glu Leu Val Arg Ile Lys Ala Lys Leu Asn Trp Gly Leu Thr Asp
    130             135             140

Glu Leu Lys Lys Ala Phe Pro Glu Asn Ile Ser Lys Glu Arg Ser Leu
145             150             155             160
```

```
Ile Asn Lys Asn Ile Pro Asn Phe Lys Trp Leu Ala Gly Phe Thr Ser
            165             170                 175

Gly Glu Gly Cys Phe Phe Val Asn Leu Ile Lys Ser Lys Ser Lys Leu
            180             185             190

Gly Val Gln Val Gln Leu Val Phe Ser Ile Thr Gln His Ile Lys Asp
            195             200             205

Lys Asn Leu Met Asn Ser Leu Ile Thr Tyr Leu Gly Cys Gly Tyr Ile
    210             215             220

Lys Glu Lys Asn Lys Ser Glu Phe Ser Trp Leu Asp Phe Val Val Thr
225             230             235                 240

Lys Phe Ser Asp Ile Asn Asp Lys Ile Ile Pro Val Phe Gln Glu Asn
            245             250             255

Thr Leu Ile Gly Val Lys Leu Glu Asp Phe Glu Asp Trp Cys Lys Val
            260             265             270

Ala Lys Leu Ile Glu Glu Lys Lys His Leu Thr Glu Ser Gly Leu Asp
            275             280             285

Glu Ile Lys Lys Ile Lys Leu Asn Met Asn Lys Gly Arg Xaa Xaa
    290             295             300
```

```
<210> SEQ ID NO 6
<211> LENGTH: 303
<212> TYPE: PRT
<213> ORGANISM: Artificial Sequence
<220> FEATURE:
<223> OTHER INFORMATION: Made in Lab - reprogrammed I-OnuI LHE variant
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (302)..(303)
<223> OTHER INFORMATION: Any amino acid or absent

<400> SEQUENCE: 6
```

```
Xaa Xaa Xaa Xaa Ser Arg Arg Glu Ser Ile Asn Pro Trp Thr Leu Thr
1               5                   10                  15

Gly Phe Ala Asp Ala Glu Gly Ser Phe Gly Leu Ser Ile Leu Asn Arg
            20              25              30

Asn Arg Gly Thr Ala Arg Tyr His Thr Arg Leu Ser Phe Thr Ile Met
        35              40              45

Leu His Asn Lys Asp Lys Ser Ile Leu Glu Asn Ile Gln Ser Thr Trp
    50              55              60

Lys Val Gly Ser Ile Leu Asn Asn Gly Asp His Tyr Val Ser Leu Val
65              70              75              80

Val Tyr Ala Phe Glu Asp Leu Lys Val Ile Ile Asp His Phe Glu Lys
            85              90              95

Tyr Pro Leu Ile Thr Gln Lys Leu Gly Asp Tyr Lys Leu Phe Lys Gln
            100             105             110

Ala Phe Ser Val Met Glu Asn Lys Glu His Leu Lys Glu Asn Gly Ile
            115             120             125

Lys Glu Leu Val Arg Ile Lys Ala Lys Met Asn Trp Gly Leu Asn Asp
    130             135             140

Glu Leu Lys Lys Ala Phe Pro Glu Val Ile Ser Arg Glu Arg Pro Leu
145             150             155             160

Ile Asn Lys Asn Ile Pro Asn Gly Lys Trp Leu Ala Gly Phe Thr Ser
            165             170                 175

Gly Asp Gly Ser Phe Phe Val Arg Leu Arg Lys Ser Asn Val Asn Ala
```

-continued

```
            180                 185                 190
Arg Val Arg Val Gln Leu Val Phe Glu Ile Ser Gln His Ile Arg Asp
        195                 200                 205

Lys Asn Leu Met Asn Ser Leu Ile Thr Tyr Leu Gly Cys Gly His Ile
        210                 215                 220

Tyr Glu Gly Asn Lys Ser Glu Arg Ser Trp Leu Gln Phe Arg Val Glu
225                 230                 235                 240

Lys Phe Ser Asp Ile Asn Asp Lys Ile Ile Pro Val Phe Gln Glu Asn
                245                 250                 255

Thr Leu Ile Gly Met Lys Leu Glu Asp Phe Glu Asp Trp Cys Lys Val
                260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Arg Arg Xaa Xaa
        290                 295                 300

<210> SEQ ID NO 7
<211> LENGTH: 944
<212> TYPE: PRT
<213> ORGANISM: Artificial Sequence
<220> FEATURE:
<223> OTHER INFORMATION: Mad in Lab - engineered PDCD-1 megaTAL
      polypeptide

<400> SEQUENCE: 7

Met Gly Ser Cys Arg Pro Pro Lys Lys Lys Arg Lys Val Val Asp Leu
1               5                   10                  15

Arg Thr Leu Gly Tyr Ser Gln Gln Gln Gln Glu Lys Ile Lys Pro Lys
                20                  25                  30

Val Arg Ser Thr Val Ala Gln His His Glu Ala Leu Val Gly His Gly
            35                  40                  45

Phe Thr His Ala His Ile Val Ala Leu Ser Gln His Pro Ala Ala Leu
        50                  55                  60

Gly Thr Val Ala Val Thr Tyr Gln His Ile Ile Thr Ala Leu Pro Glu
65                  70                  75                  80

Ala Thr His Glu Asp Ile Val Gly Val Gly Lys Gln Trp Ser Gly Ala
                85                  90                  95

Arg Ala Leu Glu Ala Leu Leu Thr Asp Ala Gly Glu Leu Arg Gly Pro
            100                 105                 110

Pro Leu Gln Leu Asp Thr Gly Gln Leu Val Lys Ile Ala Lys Arg Gly
        115                 120                 125

Gly Val Thr Ala Met Glu Ala Val His Ala Ser Arg Asn Ala Leu Thr
        130                 135                 140

Gly Ala Pro Leu Asn Leu Thr Pro Asp Gln Val Val Ala Ile Ala Ser
145                 150                 155                 160

Asn Asn Gly Gly Lys Gln Ala Leu Glu Thr Val Gln Arg Leu Leu Pro
                165                 170                 175

Val Leu Cys Gln Asp His Gly Leu Thr Pro Asp Gln Val Val Ala Ile
            180                 185                 190

Ala Ser Asn Asn Gly Gly Lys Gln Ala Leu Glu Thr Val Gln Arg Leu
        195                 200                 205

Leu Pro Val Leu Cys Gln Asp His Gly Leu Thr Pro Asp Gln Val Val
        210                 215                 220

Ala Ile Ala Ser Asn Gly Gly Gly Lys Gln Ala Leu Glu Thr Val Gln
225                 230                 235                 240
```

-continued

```
Arg Leu Leu Pro Val Leu Cys Gln Asp His Gly Leu Thr Pro Asp Gln
              245                 250                 255

Val Val Ala Ile Ala Ser Asn Asn Gly Gly Lys Gln Ala Leu Glu Thr
              260                 265                 270

Val Gln Arg Leu Leu Pro Val Leu Cys Gln Asp His Gly Leu Thr Pro
          275                 280                 285

Asp Gln Val Val Ala Ile Ala Ser Asn Asn Gly Gly Lys Gln Ala Leu
      290                 295                 300

Glu Thr Val Gln Arg Leu Leu Pro Val Leu Cys Gln Asp His Gly Leu
305                 310                 315                 320

Thr Pro Asp Gln Val Val Ala Ile Ala Ser Asn Asn Gly Gly Lys Gln
                  325                 330                 335

Ala Leu Glu Thr Val Gln Arg Leu Leu Pro Val Leu Cys Gln Asp His
              340                 345                 350

Gly Leu Thr Pro Asp Gln Val Val Ala Ile Ala Ser Asn Asn Gly Gly
          355                 360                 365

Lys Gln Ala Leu Glu Thr Val Gln Arg Leu Leu Pro Val Leu Cys Gln
      370                 375                 380

Asp His Gly Leu Thr Pro Asp Gln Val Val Ala Ile Ala Ser His Asp
385                 390                 395                 400

Gly Gly Lys Gln Ala Leu Glu Thr Val Gln Arg Leu Leu Pro Val Leu
                  405                 410                 415

Cys Gln Asp His Gly Leu Thr Pro Asp Gln Val Val Ala Ile Ala Ser
              420                 425                 430

Asn Gly Gly Gly Lys Gln Ala Leu Glu Thr Val Gln Arg Leu Leu Pro
          435                 440                 445

Val Leu Cys Gln Asp His Gly Leu Thr Pro Asp Gln Val Val Ala Ile
      450                 455                 460

Ala Ser Asn Asn Gly Gly Lys Gln Ala Leu Glu Thr Val Gln Arg Leu
465                 470                 475                 480

Leu Pro Val Leu Cys Gln Asp His Gly Leu Thr Pro Asp Gln Val Val
                  485                 490                 495

Ala Ile Ala Ser His Asp Gly Gly Lys Gln Ala Leu Glu Thr Val Gln
              500                 505                 510

Arg Leu Leu Pro Val Leu Cys Gln Asp His Gly Leu Thr Pro Asp Gln
          515                 520                 525

Val Val Ala Ile Ala Ser Asn Gly Gly Gly Lys Gln Ala Leu Glu Thr
      530                 535                 540

Val Gln Arg Leu Leu Pro Val Leu Cys Gln Asp His Gly Leu Thr Pro
545                 550                 555                 560

Asp Gln Val Val Ala Ile Ala Ser His Asp Gly Gly Lys Gln Ala Leu
                  565                 570                 575

Glu Ser Ile Val Ala Gln Leu Ser Arg Pro Asp Pro Ala Leu Ala Ala
              580                 585                 590

Leu Thr Asn Asp His Leu Val Ala Leu Ala Cys Leu Gly Gly Arg Pro
          595                 600                 605

Ala Met Asp Ala Val Lys Lys Gly Leu Pro His Ala Pro Glu Leu Ile
      610                 615                 620

Arg Arg Val Asn Arg Arg Ile Gly Glu Arg Thr Ser His Arg Val Ala
625                 630                 635                 640

Ile Ser Arg Val Gly Gly Ser Ser Arg Arg Glu Ser Ile Asn Pro Trp
                  645                 650                 655

Thr Leu Thr Gly Phe Ala Asp Ala Glu Gly Ser Phe Gly Leu Ser Ile
```

-continued

```
                660                 665                 670

Leu Asn Arg Asn Arg Gly Thr Ala Arg Tyr His Thr Arg Leu Ser Phe
        675                 680                 685

Thr Ile Met Leu His Asn Lys Asp Lys Ser Ile Leu Glu Asn Ile Gln
        690                 695                 700

Ser Thr Trp Lys Val Gly Ser Ile Leu Asn Asn Gly Asp His Tyr Val
705                 710                 715                 720

Ser Leu Val Val Tyr Ala Phe Glu Asp Leu Lys Val Ile Ile Asp His
                725                 730                 735

Phe Glu Lys Tyr Pro Leu Ile Thr Gln Lys Leu Gly Asp Tyr Lys Leu
                740                 745                 750

Phe Lys Gln Ala Phe Ser Val Met Glu Asn Lys Glu His Leu Lys Glu
        755                 760                 765

Asn Gly Ile Lys Glu Leu Val Arg Ile Lys Ala Lys Met Asn Trp Gly
        770                 775                 780

Leu Asn Asp Glu Leu Lys Lys Ala Phe Pro Glu Val Ile Ser Arg Glu
785                 790                 795                 800

Arg Pro Leu Ile Asn Lys Asn Ile Pro Asn Gly Lys Trp Leu Ala Gly
                805                 810                 815

Phe Thr Ser Gly Asp Gly Ser Phe Phe Val Arg Leu Arg Lys Ser Asn
                820                 825                 830

Val Asn Ala Arg Val Arg Val Gln Leu Val Phe Glu Ile Ser Gln His
        835                 840                 845

Ile Arg Asp Lys Asn Leu Met Asn Ser Leu Ile Thr Tyr Leu Gly Cys
        850                 855                 860

Gly His Ile Tyr Glu Gly Asn Lys Ser Glu Arg Ser Trp Leu Gln Phe
865                 870                 875                 880

Arg Val Glu Lys Phe Ser Asp Ile Asn Asp Lys Ile Ile Pro Val Phe
                885                 890                 895

Gln Glu Asn Thr Leu Ile Gly Met Lys Leu Glu Asp Phe Glu Asp Trp
                900                 905                 910

Cys Lys Val Ala Lys Leu Ile Glu Glu Lys Lys His Leu Thr Glu Ser
        915                 920                 925

Gly Leu Asp Glu Ile Lys Lys Ile Lys Leu Asn Met Asn Lys Arg Arg
        930                 935                 940
```

```
<210> SEQ ID NO 8
<211> LENGTH: 22
<212> TYPE: DNA
<213> ORGANISM: Homo sapiens

<400> SEQUENCE: 8
ggcatgcaga tcccacaggc gc                                          22

<210> SEQ ID NO 9
<211> LENGTH: 14
<212> TYPE: DNA
<213> ORGANISM: Homo sapiens

<400> SEQUENCE: 9
ggtggggctg ctcc                                                  14

<210> SEQ ID NO 10
<211> LENGTH: 37
<212> TYPE: DNA
<213> ORGANISM: Homo sapiens
```

-continued

```
<400> SEQUENCE: 10
ggtggggctg ctccaggcat gcagatccca caggcgc                                   37

<210> SEQ ID NO 11
<211> LENGTH: 2835
<212> TYPE: RNA
<213> ORGANISM: Artificial Sequence
<220> FEATURE:
<223> OTHER INFORMATION: Made in Lab - engineered PDCD-1 megaTAL mRNA

<400> SEQUENCE: 11
augggauccu gcaggccacc uaagaagaaa cgcaaagucg uggaucuacg cacgcucggc      60
uacagucagc agcagcaaga aagaucaaa ccgaaggugc guucgacagu ggcgcagcac      120
cacgaggcac uggugggcca uggguuuaca cacgcgcaca ucguugcgcu cagccaacac      180
ccggcagcgu uagggaccgu cgcugucacg uaucagcaca uaaucacggc guugccagag      240
gcgacacacg aagacaucgu uggcgucggc aaacaguggu ccggcgcacg cgcccuggag      300
gccuugcuca cggaugcggg ggaguugaga gguccgccgu uacaguugga cacaggccaa      360
cuugugaaga uugcaaaacg uggcggcgug accgcaaugg aggcagugca ugcaucgcgc      420
aaugcacuga cgggugcccc ccugaaccua accccugauc agguagucgc uauagcuuca      480
aacaacgggg gcaagcaagc acuggagacc guucaacgac uccugccagu gcucugccaa      540
gaccacggac uuacgccaga ucaggugguu gcuauugccu ccaacaaugg cgggaaacaa      600
gcguuggaaa cugugcagag acuguuaccu gucuuguguc aagaccacgg ccucacgcca      660
gaucaggugg uagccauagc gucgaaugga ggugguaagc aagcccuuga aacgguccag      720
cgucuucugc cggguguugug ccaggaccac ggacuaacgc cggaucaggu cguagccauu      780
gcuucaaaua acggcggcaa acaggcgcua gagacagucc agcgccucuu gccuguguua      840
ugccaggauc acggcuuaac cccagaccaa guuguggcua uugcaucuaa caaugguggc      900
aaacaagccu uggagacagu gcaacgauua cugccugucu uaugucagga ucauggccug      960
acgcccgauc agguagugg aaucgcaucu aauaauggag guaagcaagc acuggagacu      1020
guccagagau uguuacccgu acuaugucaa gaucaugguu ugacgccuga ucagguuguu      1080
gcgauagcca gcaacaacgg agggaaacag gcucuugaaa ccguacagcg acuucuccca      1140
gucuugugcc aagaucacgg gcuuacuccu gaucaagucg uagcuaucgc cagccacgac      1200
ggugggaaac aggcccugga aaccguacaa cgucuccucc caguacuuug ucaagaccac      1260
ggguugacuc cggaucaagu cgucgcgauc gcgagcaaug gaggggggaa gcaggcgcug      1320
gaaacuguuc agagacugcu gccuguacuu ugucaggacc auggucugac accugaccaa      1380
guuguggcga uagccaguaa caaugggga aaacaggcac uagagacggu ucaaagguug      1440
uugcccguuc ugugccagga ccacggcuug acaccggauc agguggguagc uaucgcuuca      1500 cacgauggcg aaaacaggc uuuagaaaca guccaaagac uucucccagu ccuuugucag      1560
gaccacggau ugacuccaga ucaagucguu gcuauugcaa guaaugguggu gguaagcaa      1620 gcuuuagaaa ccguacagag gcuuuugcca gugcugugcc aggaccaugg acugacccu      1680 gaucaagugu uagcaauugc aucucaugau ggaggaaaac aagcucugga aagcauugug      1740
gcccagcuga gccggccuga uccggcguug gccgcguuga ccaacgacca ccucgucgcc      1800
uuggccugcc ucggcggacg uccugccaug gaugcaguga aaaagggauu gccgcacgcg      1860
ccggaauuga ucagaagagu caaucgccgu auuggcgaac gcacguccca ucgcguugcg      1920
auaucuagag ugggaggaag cucucgcaga gaguccauca acccauggac ucugacuggu      1980
```

```
uucgcugaug ccgaaggauc auucgggcua agcauccuca acagaaacag agguacugcu      2040
agauaccaca cucgacuguc auucacaauc augcugcaca acaaggacaa aucgauucg       2100 gagaauaucc agucgacuug gaaggucggc agcauccuca acaauggcga ccacuacguc      2160
ucgcuggugg ucuacgccuu cgaagauuug aaagugauua ucgaccacuu cgagaaauau      2220
ccgcugauaa cacagaaauu gggcgauuac aaguuguuua aacaggcauu cagcgucaug      2280
gagaacaaag aacaucuuaa ggagaauggg auuaaggagc ucuacgaau caaagcuaag       2340 augaauuggg gucucaauga cgaauugaaa aaagcauuuc agaggugau uagcagggag        2400 cgccccuua ucaauaagaa cauuccgaau gggaaauggc uggcuggauu cacaucuggu        2460
gauggcuccu ucuucgugcg ccuaagaaag ucuaauguua augcuagagu acgugugcaa      2520
cugguauucg agaucucaca gcaucagac acaagaacc ugaugaauuc auugauaaca         2580
uaccuaggcu ugguucacau cuacgaggga aacaaaucug agcgcaguug gcuccaauuc      2640
agaguagaaa aauucagcga uaucaacgac aagaucauuc cgguauucca ggaaaauacu      2700
cugauuggca ugaaacucga ggacuuugaa gauuggugca agguugccaa auugaucgaa      2760
gagaagaaac accugaccga auccgguuug gaugagauua agaaaaucaa gcugaacaug      2820
aacaaaagac guuga                                                       2835
```

```
<210> SEQ ID NO 12
<211> LENGTH: 2835
<212> TYPE: RNA
<213> ORGANISM: Artificial Sequence
<220> FEATURE:
<223> OTHER INFORMATION: Made in Lab - PDCD-1 megaTAL codon optimized
      mRNA

<400> SEQUENCE: 12
```

```
augggaucgu gucggccacc gaagaagaag aggaaggugg uggaccuuag aacgcuggga        60
uacucccaac aacagcaaga gaagaucaag ccgaaggugc gcuccacugu ggcacagcau      120
cacgaggccc uggucggaca cggauucacc caugcccaca ucguggcccu cucccagcau      180
ccggcugccc ugggaaccgu cgccgugacc uaccaacaua ucaucaccgc ccuuccggaa      240
gccacgcaug aggacaucgu gggcguggga aagcaguggu caggcgcccg agccuuggaa      300
gcccuccuua ccgacgccgg agagcugaga ggaccgcccc ugcagcugga cacgggacag      360
cuggugaaga ucgcgaagag aggcggcgug acugcgaugg aagccguca cgccucacgg        420 aacgcccuca ccggagcccc gcugaaccuu acuccugauc aagucgguggc aauugccucg      480 aauaacggcg ggaagcaagc ccuugaaacc gugcaacgcc ugcugcccgu gcugugucaa      540
gaucaugguc ugacccccgga ucaggugguc gccauugcau caaacaacgg cggcaaacag      600
gcucucgaaa cuguccaacg ccuccugccg guccugugcc aggaccacgg ccucacacc        660 gaucaggucg uggcuaucgc aucuaacgga ggagggaagc aagcucugga aaccguccaa      720
cggcuucugc cuguccugug ucaagaccac ggacucaccc cggaccaagu ggucgcuauc      780
gccuccaaca acggaggaaa gcaggcuuug aaacugugc aaaggcuccu gcccguccuc        840
ugccaggauc auggccugac cccugaccaa gucgucgcua uugcgucaaa caauggcggc      900
aagcaggccc ucgaaaccgu gcagcggcug cucccagugc ugugccaaga ccacggucug      960
acgcccgacc agguggugggc aaucgcgucu aauaacggag gcaagcaagc acuugagaca      1020
gugcagagac ugcucccggu gcucugccag gaucauggac ugacccccaga ccaggucguc      1080 gccaucgcuu ccaacaacgg cggaaagcag gcgcuggaaa cuguacagag acuccuccc        1140
```

-continued

```
gugcuuuguc aagaccacgg auugacccu gaucaagugg uggccauugc gucgcacgac      1200
ggaggaaaac aggccuugga aacggugcag aggcuguuac cagugcucug ucaggaucac      1260
gguugacccc cggaccaagu cguggccauc gcgucaaacg gcggcgguaa gcaggcucug      1320
gagacugugc agcgguuguu gcccguccuu ugucaggauc acgggcuuac uccggaccag      1380
gucgucgcca ucgcgagcaa caacgguggg aagcaggcgc uugagacugu ccagcggcug      1440
uugccagugc uuugccagga ccacggucua acuccugauc aggucguggc gauugccucc      1500 cacgacgguug gaaagcaagc gcuugaaacg gugcaaagac ugcuuccugu gcugugccaa      1560
gaucacgguc ugacacccga ccaggugug gcuaucgcgu ccaaugguugg uggaaaacag      1620 gcccuggaga caguccagag gcugcugccu guucugugc aggaccaug acucacuccc      1680 gaccaggugg uggcaauagc cucgcaugau ggggggaaac aggcgcucga gagcaucgug      1740
gcucagcucu caagaccgga uccugcacug gcagcccuga ccaacgauca ccuggucgcc      1800
cucgccugcu ugggcggacg gccagccaug gacgccguga agaagggacu cccucaugcc      1860
cccgaacuca uucgccgcgu caaccggcgc aucggcgaga ggaccucaca ccgcguggcg      1920
aucucuagag ugggagguuc uucccggcgc gaaagcauua accccuggac ccucacuggc      1980
uuugccgacg cagaggggguc cuucggccug agcauucuga accgcaaucg ggguacugcg      2040
cgcuaccaca cccgcuuguc cuucaccauc augcugcaua acaaagacaa gucgauccug      2100
gagaacaucc aguccacuug gaaagucggg uccauccuca acaauggcga ucauuacgug      2160
ucccuggugg uguacgcauu cgaagaucuc aaggucauua ucgaucauuu cgagaaguac      2220
ccgcuuauua cccagaagcu gggcgacuac aagcuguuca agcaggccuu ucggucaug      2280 gaaaacaagg aacaccucaa ggagaacgga auuaaggagc ucgugcggau caaagcgaag      2340
augaacuggg gacucaacga cgaacugaag aaggcuuucc cagaggugau uagccgggaa      2400
cgcccacuca ucaacaaaaa cauuccgaac gggaaguggc ucgccggcuu caccuccgga      2460
gauggaagcu ucuucguccg gcuucgcaag uccaacguga acgcuagggu ccgggugcaa      2520
cugguguucg agaucagcca acacaucaga gacaaaaacc ucaugaacuc acucaucacc      2580
uaccugggcu gcggacacau cuacgagggc aacaaauccg agaggguccug gcugcaguuc      2640 agagucgaga aguucuccga caucaacgac aaaaucaucc cggguguuca agaaaacacc      2700
cugaucggua ugaagcugga agauuuuugag gauuggugca aggugggccaa gcucauugaa      2760 gagaagaagc accucaccga gucgggacuc gacgaaauca aaaagaucaa guugaauaug      2820
aacaagcggc gcuga                                                     2835
```

<210> SEQ ID NO 13
<211> LENGTH: 711
<212> TYPE: RNA
<213> ORGANISM: Mus musculus

<400> SEQUENCE: 13

```
augucugagc caccucgggc ugagaccuuu guauuccugg accuagaagc cacugggcuc       60
ccaaacaugg acccugagau ugcagagaua ucccuuuuug cuguucaccg cucuucccug      120
gagaacccag aacgggauga uucugguucc uuggugcugc cccguguucu ggacaagcuc      180
acacugugca ugugcccgga gcgccccuuu acugccaagg ccagugagau uacugguuug      240
agcagcgaaa gccugaugca cugcgggaag gcugguuuca auggcgcugu gguaaggaca      300
cugcagggcu uccuaagccg ccaggagggc cccaucugcc uuguggccca caauggcuuc      360
```

```
gauuaugacu ucccacugcu gugcacgggg cuacaacguc uggguaccca ucugccccaa      420
gacacugucu gccuggacac acugccugca uugcggggcc uggaccgugc ucacagccac      480
ggcaccaggg cucaaggccg caaaagcuac agccuggcca gucucuucca ccgcuacuuc      540
caggcugaac ccagugcugc ccauucagca gaaggugaug ugcacacccu gcuucugauc      600
uuccugcauc gugcuccuga gcugcucgcc ugggcagaug agcaggcccg cagcugggcu      660
cauauugagc ccauguacgu gccaccugau gguccaagcc ucgaagccug a              711
```

<210> SEQ ID NO 14
<211> LENGTH: 236
<212> TYPE: PRT
<213> ORGANISM: Mus musculus

<400> SEQUENCE: 14

```
Met Ser Glu Pro Pro Arg Ala Glu Thr Phe Val Phe Leu Asp Leu Glu
1               5                   10                  15

Ala Thr Gly Leu Pro Asn Met Asp Pro Glu Ile Ala Glu Ile Ser Leu
            20                  25                  30

Phe Ala Val His Arg Ser Ser Leu Glu Asn Pro Glu Arg Asp Asp Ser
        35                  40                  45

Gly Ser Leu Val Leu Pro Arg Val Leu Asp Lys Leu Thr Leu Cys Met
    50                  55                  60

Cys Pro Glu Arg Pro Phe Thr Ala Lys Ala Ser Glu Ile Thr Gly Leu
65                  70                  75                  80

Ser Ser Glu Ser Leu Met His Cys Gly Lys Ala Gly Phe Asn Gly Ala
                85                  90                  95

Val Val Arg Thr Leu Gln Gly Phe Leu Ser Arg Gln Glu Gly Pro Ile
            100                 105                 110

Cys Leu Val Ala His Asn Gly Phe Asp Tyr Asp Phe Pro Leu Leu Cys
        115                 120                 125

Thr Gly Leu Gln Arg Leu Gly Ala His Leu Pro Gln Asp Thr Val Cys
    130                 135                 140

Leu Asp Thr Leu Pro Ala Leu Arg Gly Leu Asp Arg Ala His Ser His
145                 150                 155                 160

Gly Thr Arg Ala Gln Gly Arg Lys Ser Tyr Ser Leu Ala Ser Leu Phe
                165                 170                 175

His Arg Tyr Phe Gln Ala Glu Pro Ser Ala Ala His Ser Ala Glu Gly
            180                 185                 190

Asp Val His Thr Leu Leu Leu Ile Phe Leu His Arg Ala Pro Glu Leu
        195                 200                 205

Leu Ala Trp Ala Asp Glu Gln Ala Arg Ser Trp Ala His Ile Glu Pro
    210                 215                 220

Met Tyr Val Pro Pro Asp Gly Pro Ser Leu Glu Ala
225                 230                 235
```

<210> SEQ ID NO 15
<211> LENGTH: 944
<212> TYPE: PRT
<213> ORGANISM: Artificial Sequence
<220> FEATURE:
<223> OTHER INFORMATION: Made in Lab - engineered PDCD-1 megaTAL
      polypeptide

<400> SEQUENCE: 15

```
Met Gly Ser Cys Arg Pro Pro Lys Lys Lys Arg Lys Val Val Asp Leu
1               5                   10                  15
```

```
Arg Thr Leu Gly Tyr Ser Gln Gln Gln Glu Lys Ile Lys Pro Lys
        20              25                  30

Val Arg Ser Thr Val Ala Gln His His Glu Ala Leu Val Gly His Gly
        35              40              45

Phe Thr His Ala His Ile Val Ala Leu Ser Gln His Pro Ala Ala Leu
    50              55              60

Gly Thr Val Ala Val Thr Tyr Gln His Ile Ile Thr Ala Leu Pro Glu
65              70              75                  80

Ala Thr His Glu Asp Ile Val Gly Val Gly Lys Gln Trp Ser Gly Ala
            85              90                  95

Arg Ala Leu Glu Ala Leu Leu Thr Asp Ala Gly Glu Leu Arg Gly Pro
        100             105             110

Pro Leu Gln Leu Asp Thr Gly Gln Leu Val Lys Ile Ala Lys Arg Gly
        115             120             125

Gly Val Thr Ala Met Glu Ala Val His Ala Ser Arg Asn Ala Leu Thr
    130             135             140

Gly Ala Pro Leu Asn Leu Thr Pro Asp Gln Val Val Ala Ile Ala Ser
145             150             155             160

Asn Asn Gly Gly Lys Gln Ala Leu Glu Thr Val Gln Arg Leu Leu Pro
            165             170             175

Val Leu Cys Gln Asp His Gly Leu Thr Pro Asp Gln Val Val Ala Ile
        180             185             190

Ala Ser Asn Asn Gly Gly Lys Gln Ala Leu Glu Thr Val Gln Arg Leu
        195             200             205

Leu Pro Val Leu Cys Gln Asp His Gly Leu Thr Pro Asp Gln Val Val
    210             215             220

Ala Ile Ala Ser Asn Gly Gly Lys Gln Ala Leu Glu Thr Val Gln
225             230             235             240

Arg Leu Leu Pro Val Leu Cys Gln Asp His Gly Leu Thr Pro Asp Gln
            245             250             255

Val Val Ala Ile Ala Ser Asn Asn Gly Gly Lys Gln Ala Leu Glu Thr
        260             265             270

Val Gln Arg Leu Leu Pro Val Leu Cys Gln Asp His Gly Leu Thr Pro
        275             280             285

Asp Gln Val Val Ala Ile Ala Ser Asn Asn Gly Gly Lys Gln Ala Leu
    290             295             300

Glu Thr Val Gln Arg Leu Leu Pro Val Leu Cys Gln Asp His Gly Leu
305             310             315             320

Thr Pro Asp Gln Val Val Ala Ile Ala Ser Asn Asn Gly Gly Lys Gln
            325             330             335

Ala Leu Glu Thr Val Gln Arg Leu Leu Pro Val Leu Cys Gln Asp His
        340             345             350

Gly Leu Thr Pro Asp Gln Val Val Ala Ile Ala Ser Asn Asn Gly Gly
        355             360             365

Lys Gln Ala Leu Glu Thr Val Gln Arg Leu Leu Pro Val Leu Cys Gln
    370             375             380

Asp His Gly Leu Thr Pro Asp Gln Val Val Ala Ile Ala Ser His Asp
385             390             395             400

Gly Gly Lys Gln Ala Leu Glu Thr Val Gln Arg Leu Leu Pro Val Leu
            405             410             415

Cys Gln Asp His Gly Leu Thr Pro Asp Gln Val Val Ala Ile Ala Ser
            420             425             430

Asn Gly Gly Gly Lys Gln Ala Leu Glu Thr Val Gln Arg Leu Leu Pro
```

-continued

```
               435                   440                   445
Val Leu Cys Gln Asp His Gly Leu Thr Pro Asp Gln Val Val Ala Ile
        450                   455                   460
Ala Ser Asn Asn Gly Gly Lys Gln Ala Leu Glu Thr Val Gln Arg Leu
465                   470                   475                   480
Leu Pro Val Leu Cys Gln Asp His Gly Leu Thr Pro Asp Gln Val Val
                    485                   490                   495
Ala Ile Ala Ser His Asp Gly Gly Lys Gln Ala Leu Glu Thr Val Gln
                500                   505                   510
Arg Leu Leu Pro Val Leu Cys Gln Asp His Gly Leu Thr Pro Asp Gln
            515                   520                   525
Val Val Ala Ile Ala Ser Asn Gly Gly Gly Lys Gln Ala Leu Glu Thr
        530                   535                   540
Val Gln Arg Leu Leu Pro Val Leu Cys Gln Asp His Gly Leu Thr Pro
545                   550                   555                   560
Asp Gln Val Val Ala Ile Ala Ser His Asp Gly Gly Lys Gln Ala Leu
                565                   570                   575
Glu Ser Ile Val Ala Gln Leu Ser Arg Pro Asp Pro Ala Leu Ala Ala
            580                   585                   590
Leu Thr Asn Asp His Leu Val Ala Leu Ala Cys Leu Gly Gly Arg Pro
            595                   600                   605
Ala Met Asp Ala Val Lys Lys Gly Leu Pro His Ala Pro Glu Leu Ile
        610                   615                   620
Arg Arg Val Asn Arg Arg Ile Gly Glu Arg Thr Ser His Arg Val Ala
625                   630                   635                   640
Ile Ser Arg Val Gly Gly Ser Ser Arg Arg Glu Ser Ile Asn Pro Trp
                645                   650                   655
Ile Leu Thr Gly Phe Ala Asp Ala Glu Gly Ser Phe Gly Leu Ser Ile
            660                   665                   670
Leu Asn Arg Asn Arg Gly Thr Ala Arg Tyr His Thr Arg Leu Ser Phe
            675                   680                   685
Ala Ile Val Leu His Asn Lys Asp Lys Ser Ile Leu Glu Asn Ile Gln
        690                   695                   700
Ser Thr Trp Lys Val Gly Ile Ile Thr Asn Asp Gly Asp Arg Tyr Val
705                   710                   715                   720
Arg Leu Arg Val Thr Arg Phe Glu Asp Leu Lys Val Ile Ile Asp His
            725                   730                   735
Phe Glu Lys Tyr Pro Leu Val Thr Gln Lys Leu Gly Asp Tyr Lys Leu
            740                   745                   750
Phe Lys Gln Ala Phe Ser Val Met Glu Asn Lys Glu His Leu Lys Glu
        755                   760                   765
Asn Gly Ile Lys Glu Leu Val Arg Ile Lys Ala Lys Met Asn Trp Gly
        770                   775                   780
Leu Asn Asp Glu Leu Lys Lys Ala Phe Pro Glu Asn Ile Ser Lys Glu
785                   790                   795                   800
Arg Pro Leu Ile Asn Lys Asn Ile Pro Asn Phe Lys Trp Leu Ala Gly
                805                   810                   815
Phe Thr Ser Gly Asp Gly Ser Phe Phe Val Arg Leu Arg Lys Ser Asn
            820                   825                   830
Val Asn Ala Arg Val Arg Val Gln Leu Val Phe Glu Ile Ser Gln His
        835                   840                   845
Ile Arg Asp Lys Asn Leu Met Asn Ser Leu Ile Thr Tyr Leu Gly Cys
850                   855                   860
```

-continued

```
Gly His Ile Tyr Glu Gly Asn Lys Ser Glu Arg Ser Trp Leu Gln Phe
865                 870                 875                 880

Arg Val Glu Lys Phe Ser Asp Ile Asn Asp Lys Ile Ile Pro Val Phe
                885                 890                 895

Gln Glu Asn Thr Leu Ile Gly Val Lys Leu Glu Asp Phe Glu Asp Trp
                900                 905                 910

Cys Lys Val Ala Lys Leu Ile Glu Glu Lys Lys His Leu Thr Glu Ser
            915                 920                 925

Gly Leu Asp Glu Ile Lys Lys Ile Lys Leu Asn Met Asn Lys Gly Arg
        930                 935                 940
```

<210> SEQ ID NO 16
<211> LENGTH: 944
<212> TYPE: PRT
<213> ORGANISM: Artificial Sequence
<220> FEATURE:
<223> OTHER INFORMATION: Made in Lab - engineered PDCD-1 megaTAL
      polypeptide

<400> SEQUENCE: 16

```
Met Gly Ser Cys Arg Pro Pro Lys Lys Lys Arg Lys Val Val Asp Leu
1               5                   10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
            35                  40                  45

Phe Thr His Ala His Ile Val Ala Leu Ser Gln His Pro Ala Ala Leu
    50                  55                  60

Gly Thr Val Ala Val Thr Tyr Gln His Ile Ile Thr Ala Leu Pro Glu
65                  70                  75                  80

Ala Thr His Glu Asp Ile Val Gly Val Gly Lys Gln Trp Ser Gly Ala
                85                  90                  95

Arg Ala Leu Glu Ala Leu Leu Thr Asp Ala Gly Glu Leu Arg Gly Pro
            100                 105                 110

Pro Leu Gln Leu Asp Thr Gly Gln Leu Val Lys Ile Ala Lys Arg Gly
            115                 120                 125

Gly Val Thr Ala Met Glu Ala Val His Ala Ser Arg Asn Ala Leu Thr
    130                 135                 140

Gly Ala Pro Leu Asn Leu Thr Pro Asp Gln Val Val Ala Ile Ala Ser
145                 150                 155                 160

Asn Asn Gly Gly Lys Gln Ala Leu Glu Thr Val Gln Arg Leu Leu Pro
                165                 170                 175

Val Leu Cys Gln Asp His Gly Leu Thr Pro Asp Gln Val Val Ala Ile
            180                 185                 190

Ala Ser Asn Asn Gly Gly Lys Gln Ala Leu Glu Thr Val Gln Arg Leu
        195                 200                 205

Leu Pro Val Leu Cys Gln Asp His Gly Leu Thr Pro Asp Gln Val Val
    210                 215                 220

Ala Ile Ala Ser Asn Gly Gly Gly Lys Gln Ala Leu Glu Thr Val Gln
225                 230                 235                 240

Arg Leu Leu Pro Val Leu Cys Gln Asp His Gly Leu Thr Pro Asp Gln
                245                 250                 255

Val Val Ala Ile Ala Ser Asn Asn Gly Gly Lys Gln Ala Leu Glu Thr
            260                 265                 270

Val Gln Arg Leu Leu Pro Val Leu Cys Gln Asp His Gly Leu Thr Pro
```

```
        275                 280                 285

Asp Gln Val Val Ala Ile Ala Ser Asn Asn Gly Gly Lys Gln Ala Leu
    290                 295                 300

Glu Thr Val Gln Arg Leu Leu Pro Val Leu Cys Gln Asp His Gly Leu
305                 310                 315                 320

Thr Pro Asp Gln Val Val Ala Ile Ala Ser Asn Asn Gly Gly Lys Gln
                325                 330                 335

Ala Leu Glu Thr Val Gln Arg Leu Leu Pro Val Leu Cys Gln Asp His
            340                 345                 350

Gly Leu Thr Pro Asp Gln Val Val Ala Ile Ala Ser Asn Asn Gly Gly
            355                 360                 365

Lys Gln Ala Leu Glu Thr Val Gln Arg Leu Leu Pro Val Leu Cys Gln
    370                 375                 380

Asp His Gly Leu Thr Pro Asp Gln Val Val Ala Ile Ala Ser His Asp
385                 390                 395                 400

Gly Gly Lys Gln Ala Leu Glu Thr Val Gln Arg Leu Leu Pro Val Leu
                405                 410                 415

Cys Gln Asp His Gly Leu Thr Pro Asp Gln Val Val Ala Ile Ala Ser
            420                 425                 430

Asn Gly Gly Gly Lys Gln Ala Leu Glu Thr Val Gln Arg Leu Leu Pro
            435                 440                 445

Val Leu Cys Gln Asp His Gly Leu Thr Pro Asp Gln Val Val Ala Ile
    450                 455                 460

Ala Ser Asn Asn Gly Gly Lys Gln Ala Leu Glu Thr Val Gln Arg Leu
465                 470                 475                 480

Leu Pro Val Leu Cys Gln Asp His Gly Leu Thr Pro Asp Gln Val Val
            485                 490                 495

Ala Ile Ala Ser His Asp Gly Gly Lys Gln Ala Leu Glu Thr Val Gln
            500                 505                 510

Arg Leu Leu Pro Val Leu Cys Gln Asp His Gly Leu Thr Pro Asp Gln
            515                 520                 525

Val Val Ala Ile Ala Ser Asn Gly Gly Gly Lys Gln Ala Leu Glu Thr
    530                 535                 540

Val Gln Arg Leu Leu Pro Val Leu Cys Gln Asp His Gly Leu Thr Pro
545                 550                 555                 560

Asp Gln Val Val Ala Ile Ala Ser His Asp Gly Gly Lys Gln Ala Leu
                565                 570                 575

Glu Ser Ile Val Ala Gln Leu Ser Arg Pro Asp Pro Ala Leu Ala Ala
            580                 585                 590

Leu Thr Asn Asp His Leu Val Ala Leu Ala Cys Leu Gly Gly Arg Pro
            595                 600                 605

Ala Met Asp Ala Val Lys Lys Gly Leu Pro His Ala Pro Glu Leu Ile
    610                 615                 620

Arg Arg Val Asn Arg Arg Ile Gly Glu Arg Thr Ser His Arg Val Ala
625                 630                 635                 640

Ile Ser Arg Val Gly Gly Ser Ser Arg Arg Glu Ser Ile Asn Pro Trp
                645                 650                 655

Ile Leu Thr Gly Phe Ala Asp Ala Glu Gly Ser Phe Gly Leu Ser Ile
            660                 665                 670

Leu Asn Arg Asn Arg Gly Thr Ala Arg Tyr His Thr Arg Leu Ser Phe
            675                 680                 685

Thr Ile Val Leu His Asn Lys Asp Lys Ser Ile Leu Glu Asn Ile Gln
    690                 695                 700
```

-continued

```
Ser Thr Trp Lys Val Gly Ile Ile Thr Asn Asp Gly Asp Arg Tyr Val
705                 710                 715                 720

Arg Leu Cys Val Thr Arg Phe Glu Asp Leu Lys Val Ile Ile Asp His
                    725                 730                 735

Phe Glu Lys Tyr Pro Leu Val Thr Gln Lys Leu Gly Asp Tyr Lys Leu
                740                 745                 750

Phe Lys Gln Ala Phe Ser Val Met Glu Asn Lys Glu His Leu Lys Glu
            755                 760                 765

Asn Gly Ile Lys Glu Leu Ala Arg Ile Lys Ala Lys Met Asn Trp Gly
        770                 775                 780

Leu Asn Asp Glu Leu Lys Lys Ala Phe Pro Glu Asn Ile Gly Lys Glu
785                 790                 795                 800

Arg Pro Leu Ile Asn Lys Asn Ile Pro Asn Phe Lys Trp Leu Ala Gly
                    805                 810                 815

Phe Thr Ser Gly Asp Gly Ser Phe Phe Val Arg Leu Arg Lys Ser Asn
                820                 825                 830

Val Asn Ala Arg Val Arg Val Gln Leu Val Phe Glu Ile Ser Gln His
            835                 840                 845

Ile Arg Asp Lys Asn Leu Met Asn Ser Leu Ile Thr Tyr Leu Gly Cys
        850                 855                 860

Gly His Ile Tyr Glu Gly Asn Lys Ser Glu Arg Ser Trp Leu Gln Phe
865                 870                 875                 880

Arg Val Glu Lys Phe Ser Asp Ile Asn Asp Lys Ile Ile Pro Val Phe
                    885                 890                 895

Gln Glu Asn Thr Leu Ile Gly Val Lys Leu Glu Asp Phe Glu Asp Trp
                900                 905                 910

Cys Lys Val Ala Lys Leu Ile Glu Glu Lys Lys His Leu Thr Glu Ser
            915                 920                 925

Gly Leu Asp Glu Ile Lys Lys Ile Lys Leu Asn Met Asn Lys Gly Arg
        930                 935                 940
```

```
<210> SEQ ID NO 17
<211> LENGTH: 944
<212> TYPE: PRT
<213> ORGANISM: Artificial Sequence
<220> FEATURE:
<223> OTHER INFORMATION: Made in Lab - engineered PDCD-1 megaTAL
      polypeptide

<400> SEQUENCE: 17
```

```
Met Gly Ser Cys Arg Pro Pro Lys Lys Lys Arg Lys Val Val Asp Leu
1               5                   10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Thr Tyr Gln His Ile Ile Thr Ala Leu Pro Glu
65                  70                  75                  80

Ala Thr His Glu Asp Ile Val Gly Val Gly Lys Gln Trp Ser Gly Ala
                85                  90                  95

Arg Ala Leu Glu Ala Leu Leu Thr Asp Ala Gly Glu Leu Arg Gly Pro
            100                 105                 110

Pro Leu Gln Leu Asp Thr Gly Gln Leu Val Lys Ile Ala Lys Arg Gly
```

```
              115                   120                   125
Gly Val Thr Ala Met Glu Ala Val His Ala Ser Arg Asn Ala Leu Thr
    130                   135                   140

Gly Ala Pro Leu Asn Leu Thr Pro Asp Gln Val Val Ala Ile Ala Ser
145                   150                   155                   160

Asn Asn Gly Gly Lys Gln Ala Leu Glu Thr Val Gln Arg Leu Leu Pro
                  165                   170                   175

Val Leu Cys Gln Asp His Gly Leu Thr Pro Asp Gln Val Val Ala Ile
                  180                   185                   190

Ala Ser Asn Asn Gly Gly Lys Gln Ala Leu Glu Thr Val Gln Arg Leu
                  195                   200                   205

Leu Pro Val Leu Cys Gln Asp His Gly Leu Thr Pro Asp Gln Val Val
    210                   215                   220

Ala Ile Ala Ser Asn Gly Gly Gly Lys Gln Ala Leu Glu Thr Val Gln
225                   230                   235                   240

Arg Leu Leu Pro Val Leu Cys Gln Asp His Gly Leu Thr Pro Asp Gln
                  245                   250                   255

Val Val Ala Ile Ala Ser Asn Asn Gly Gly Lys Gln Ala Leu Glu Thr
                  260                   265                   270

Val Gln Arg Leu Leu Pro Val Leu Cys Gln Asp His Gly Leu Thr Pro
                  275                   280                   285

Asp Gln Val Val Ala Ile Ala Ser Asn Asn Gly Gly Lys Gln Ala Leu
    290                   295                   300

Glu Thr Val Gln Arg Leu Leu Pro Val Leu Cys Gln Asp His Gly Leu
305                   310                   315                   320

Thr Pro Asp Gln Val Val Ala Ile Ala Ser Asn Asn Gly Gly Lys Gln
                  325                   330                   335

Ala Leu Glu Thr Val Gln Arg Leu Leu Pro Val Leu Cys Gln Asp His
                  340                   345                   350

Gly Leu Thr Pro Asp Gln Val Val Ala Ile Ala Ser Asn Asn Gly Gly
                  355                   360                   365

Lys Gln Ala Leu Glu Thr Val Gln Arg Leu Leu Pro Val Leu Cys Gln
    370                   375                   380

Asp His Gly Leu Thr Pro Asp Gln Val Val Ala Ile Ala Ser His Asp
385                   390                   395                   400

Gly Gly Lys Gln Ala Leu Glu Thr Val Gln Arg Leu Leu Pro Val Leu
                  405                   410                   415

Cys Gln Asp His Gly Leu Thr Pro Asp Gln Val Val Ala Ile Ala Ser
                  420                   425                   430

Asn Gly Gly Gly Lys Gln Ala Leu Glu Thr Val Gln Arg Leu Leu Pro
                  435                   440                   445

Val Leu Cys Gln Asp His Gly Leu Thr Pro Asp Gln Val Val Ala Ile
    450                   455                   460

Ala Ser Asn Asn Gly Gly Lys Gln Ala Leu Glu Thr Val Gln Arg Leu
465                   470                   475                   480

Leu Pro Val Leu Cys Gln Asp His Gly Leu Thr Pro Asp Gln Val Val
                  485                   490                   495

Ala Ile Ala Ser His Asp Gly Gly Lys Gln Ala Leu Glu Thr Val Gln
                  500                   505                   510

Arg Leu Leu Pro Val Leu Cys Gln Asp His Gly Leu Thr Pro Asp Gln
                  515                   520                   525

Val Val Ala Ile Ala Ser Asn Gly Gly Gly Lys Gln Ala Leu Glu Thr
    530                   535                   540
```

-continued

```
Val Gln Arg Leu Leu Pro Val Leu Cys Gln Asp His Gly Leu Thr Pro
545                 550             555             560

Asp Gln Val Val Ala Ile Ala Ser His Asp Gly Gly Lys Gln Ala Leu
            565             570             575

Glu Ser Ile Val Ala Gln Leu Ser Arg Pro Asp Pro Ala Leu Ala Ala
            580             585             590

Leu Thr Asn Asp His Leu Val Ala Leu Ala Cys Leu Gly Gly Arg Pro
        595             600             605

Ala Met Asp Ala Val Lys Lys Gly Leu Pro His Ala Pro Glu Leu Ile
        610             615             620

Arg Arg Val Asn Arg Arg Ile Gly Glu Arg Thr Ser His Arg Val Ala
625             630             635             640

Ile Ser Arg Val Gly Gly Ser Ser Arg Arg Glu Ser Ile Asn Pro Trp
            645             650             655

Ile Leu Thr Gly Phe Ala Asp Ala Glu Gly Ser Phe Gly Leu Ser Ile
            660             665             670

Leu Asn Arg Asn Arg Gly Thr Ala Arg Tyr His Thr Arg Leu Ser Phe
        675             680             685

Thr Ile Met Leu His Asn Lys Asp Lys Ser Ile Leu Glu Asn Ile Gln
        690             695             700

Ser Thr Trp Lys Val Gly Ile Ile Thr Asn Asn Gly Asp His Tyr Val
705             710             715             720

Thr Leu Arg Val Thr Arg Phe Glu Asp Leu Lys Val Ile Ile Asp His
            725             730             735

Phe Glu Lys Tyr Pro Leu Val Thr Gln Lys Leu Gly Asp Tyr Lys Leu
            740             745             750

Phe Lys Gln Ala Phe Ser Val Met Glu Asn Lys Glu His Leu Lys Glu
        755             760             765

Asn Gly Ile Lys Glu Leu Val Arg Ile Lys Ala Lys Met Asn Trp Gly
        770             775             780

Leu Asn Asp Glu Leu Lys Lys Ala Phe Pro Glu Asn Ile Ser Lys Glu
785             790             795             800

Arg Pro Leu Ile Asn Lys Asn Ile Pro Asn Phe Lys Trp Leu Ala Gly
            805             810             815

Phe Thr Ser Gly Asp Gly Ser Phe Phe Val Arg Leu Arg Lys Ser Asn
            820             825             830

Val Asn Ala Arg Val Arg Val Gln Leu Val Phe Glu Ile Ser Gln His
        835             840             845

Ile Arg Asp Lys Asn Leu Met Asn Ser Leu Ile Thr Tyr Leu Gly Cys
        850             855             860

Gly His Ile Tyr Glu Gly Asn Lys Ser Glu Arg Ser Trp Leu Gln Phe
865             870             875             880

Arg Val Glu Lys Phe Ser Asp Ile Asn Asp Lys Ile Ile Pro Val Phe
            885             890             895

Gln Glu Asn Thr Leu Ile Gly Val Lys Leu Glu Asp Phe Glu Asp Trp
            900             905             910

Cys Lys Val Ala Lys Leu Ile Glu Glu Lys Lys His Leu Thr Glu Ser
        915             920             925

Gly Leu Asp Glu Ile Lys Lys Ile Lys Leu Asn Met Asn Lys Gly Arg
        930             935             940
```

<210> SEQ ID NO 18
<211> LENGTH: 944

<212> TYPE: PRT
<213> ORGANISM: Artificial Sequence
<220> FEATURE:
<223> OTHER INFORMATION: Made in Lab - engineered PDCD-1 megaTAL
      polypeptide

<400> SEQUENCE: 18

```
Met Gly Ser Cys Arg Pro Pro Lys Lys Lys Arg Lys Val Val Asp Leu
1               5                   10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Thr Tyr Gln His Ile Ile Thr Ala Leu Pro Glu
65                  70                  75                  80

Ala Thr His Glu Asp Ile Val Gly Val Gly Lys Gln Trp Ser Gly Ala
                85                  90                  95

Arg Ala Leu Glu Ala Leu Leu Thr Asp Ala Gly Glu Leu Arg Gly Pro
            100                 105                 110

Pro Leu Gln Leu Asp Thr Gly Gln Leu Val Lys Ile Ala Lys Arg Gly
        115                 120                 125

Gly Val Thr Ala Met Glu Ala Val His Ala Ser Arg Asn Ala Leu Thr
    130                 135                 140

Gly Ala Pro Leu Asn Leu Thr Pro Asp Gln Val Val Ala Ile Ala Ser
145                 150                 155                 160

Asn Asn Gly Gly Lys Gln Ala Leu Glu Thr Val Gln Arg Leu Leu Pro
                165                 170                 175

Val Leu Cys Gln Asp His Gly Leu Thr Pro Asp Gln Val Val Ala Ile
            180                 185                 190

Ala Ser Asn Asn Gly Gly Lys Gln Ala Leu Glu Thr Val Gln Arg Leu
            195                 200                 205

Leu Pro Val Leu Cys Gln Asp His Gly Leu Thr Pro Asp Gln Val Val
    210                 215                 220

Ala Ile Ala Ser Asn Gly Gly Gly Lys Gln Ala Leu Glu Thr Val Gln
225                 230                 235                 240

Arg Leu Leu Pro Val Leu Cys Gln Asp His Gly Leu Thr Pro Asp Gln
            245                 250                 255

Val Val Ala Ile Ala Ser Asn Asn Gly Gly Lys Gln Ala Leu Glu Thr
            260                 265                 270

Val Gln Arg Leu Leu Pro Val Leu Cys Gln Asp His Gly Leu Thr Pro
        275                 280                 285

Asp Gln Val Val Ala Ile Ala Ser Asn Asn Gly Gly Lys Gln Ala Leu
    290                 295                 300

Glu Thr Val Gln Arg Leu Leu Pro Val Leu Cys Gln Asp His Gly Leu
305                 310                 315                 320

Thr Pro Asp Gln Val Val Ala Ile Ala Ser Asn Asn Gly Gly Lys Gln
            325                 330                 335

Ala Leu Glu Thr Val Gln Arg Leu Leu Pro Val Leu Cys Gln Asp His
            340                 345                 350

Gly Leu Thr Pro Asp Gln Val Val Ala Ile Ala Ser Asn Asn Gly Gly
        355                 360                 365

Lys Gln Ala Leu Glu Thr Val Gln Arg Leu Leu Pro Val Leu Cys Gln
    370                 375                 380
```

-continued

```
Asp His Gly Leu Thr Pro Asp Gln Val Val Ala Ile Ala Ser His Asp
385                 390                 395                 400

Gly Gly Lys Gln Ala Leu Glu Thr Val Gln Arg Leu Leu Pro Val Leu
                405                 410                 415

Cys Gln Asp His Gly Leu Thr Pro Asp Gln Val Val Ala Ile Ala Ser
            420                 425                 430

Asn Gly Gly Gly Lys Gln Ala Leu Glu Thr Val Gln Arg Leu Leu Pro
            435                 440                 445

Val Leu Cys Gln Asp His Gly Leu Thr Pro Asp Gln Val Val Ala Ile
        450                 455                 460

Ala Ser Asn Asn Gly Gly Lys Gln Ala Leu Glu Thr Val Gln Arg Leu
465                 470                 475                 480

Leu Pro Val Leu Cys Gln Asp His Gly Leu Thr Pro Asp Gln Val Val
            485                 490                 495

Ala Ile Ala Ser His Asp Gly Gly Lys Gln Ala Leu Glu Thr Val Gln
            500                 505                 510

Arg Leu Leu Pro Val Leu Cys Gln Asp His Gly Leu Thr Pro Asp Gln
        515                 520                 525

Val Val Ala Ile Ala Ser Asn Gly Gly Gly Lys Gln Ala Leu Glu Thr
        530                 535                 540

Val Gln Arg Leu Leu Pro Val Leu Cys Gln Asp His Gly Leu Thr Pro
545                 550                 555                 560

Asp Gln Val Val Ala Ile Ala Ser His Asp Gly Gly Lys Gln Ala Leu
            565                 570                 575

Glu Ser Ile Val Ala Gln Leu Ser Arg Pro Asp Pro Ala Leu Ala Ala
            580                 585                 590

Leu Thr Asn Asp His Leu Val Ala Leu Ala Cys Leu Gly Gly Arg Pro
            595                 600                 605

Ala Met Asp Ala Val Lys Lys Gly Leu Pro His Ala Pro Glu Leu Ile
        610                 615                 620

Arg Arg Val Asn Arg Arg Ile Gly Glu Arg Thr Ser His Arg Val Ala
625                 630                 635                 640

Ile Ser Arg Val Gly Gly Ser Ser Arg Arg Glu Ser Ile Asn Pro Trp
                645                 650                 655

Ile Leu Thr Gly Phe Ala Asp Ala Glu Gly Ser Phe Gly Leu Ser Ile
            660                 665                 670

Leu Asn Arg Asn Arg Gly Thr Ala Arg Tyr His Thr Arg Leu Ser Phe
        675                 680                 685

Thr Ile Met Leu His Asn Lys Asp Lys Ser Ile Leu Glu Asn Ile Gln
        690                 695                 700

Ser Thr Trp Lys Val Gly Ser Ile Leu Asn Asn Gly Asp His Tyr Val
705                 710                 715                 720

Ser Leu Val Val Tyr Arg Phe Glu Asp Leu Lys Val Ile Ile Asp His
                725                 730                 735

Phe Glu Lys Tyr Pro Leu Ile Thr Gln Lys Leu Gly Asp Tyr Lys Leu
                740                 745                 750

Phe Lys Gln Ala Phe Ser Val Met Glu Asn Lys Glu His Leu Lys Glu
            755                 760                 765

Asn Gly Ile Lys Glu Leu Val Arg Ile Lys Ala Lys Met Asn Trp Gly
            770                 775                 780

Leu Asn Asp Glu Leu Lys Lys Ala Phe Pro Glu Asn Ile Ser Lys Glu
785                 790                 795                 800
```

-continued

```
Arg Pro Leu Ile Asn Lys Asn Ile Pro Asn Phe Lys Trp Leu Ala Gly
            805             810             815

Phe Thr Ser Gly Asp Gly Ser Phe Phe Val Arg Leu Arg Lys Ser Asn
            820             825             830

Val Asn Ala Arg Val Arg Val Gln Leu Val Phe Glu Ile Ser Gln His
            835             840             845

Ile Arg Asp Lys Asn Leu Met Asn Ser Leu Ile Thr Tyr Leu Gly Cys
        850             855             860

Gly His Ile Tyr Glu Gly Asn Lys Ser Glu Arg Ser Trp Leu Gln Phe
865             870             875             880

Arg Val Glu Lys Phe Ser Asp Ile Asn Asp Lys Ile Ile Pro Val Phe
                885             890             895

Gln Glu Asn Thr Leu Ile Gly Val Lys Leu Glu Asp Phe Glu Asp Trp
            900             905             910

Cys Lys Val Ala Lys Leu Ile Glu Glu Lys Lys His Leu Thr Glu Ser
            915             920             925

Gly Leu Asp Glu Ile Lys Lys Ile Lys Leu Asn Met Asn Lys Gly Arg
        930             935             940
```

```
<210> SEQ ID NO 19
<211> LENGTH: 944
<212> TYPE: PRT
<213> ORGANISM: Artificial Sequence
<220> FEATURE:
<223> OTHER INFORMATION: Made in Lab - engineered PDCD-1 megaTAL
      polypeptide

<400> SEQUENCE: 19
```

```
Met Gly Ser Cys Arg Pro Pro Lys Lys Lys Arg Lys Val Val Asp Leu
1               5               10              15

Arg Thr Leu Gly Tyr Ser Gln Gln Gln Glu Lys Ile Lys Pro Lys
            20              25              30

Val Arg Ser Thr Val Ala Gln His His Glu Ala Leu Val Gly His Gly
            35              40              45

Phe Thr His Ala His Ile Val Ala Leu Ser Gln His Pro Ala Ala Leu
        50              55              60

Gly Thr Val Ala Val Thr Tyr Gln His Ile Ile Thr Ala Leu Pro Glu
65              70              75              80

Ala Thr His Glu Asp Ile Val Gly Val Gly Lys Gln Trp Ser Gly Ala
            85              90              95

Arg Ala Leu Glu Ala Leu Leu Thr Asp Ala Gly Glu Leu Arg Gly Pro
            100             105             110

Pro Leu Gln Leu Asp Thr Gly Gln Leu Val Lys Ile Ala Lys Arg Gly
            115             120             125

Gly Val Thr Ala Met Glu Ala Val His Ala Ser Arg Asn Ala Leu Thr
        130             135             140

Gly Ala Pro Leu Asn Leu Thr Pro Asp Gln Val Val Ala Ile Ala Ser
145             150             155             160

Asn Asn Gly Gly Lys Gln Ala Leu Glu Thr Val Gln Arg Leu Leu Pro
            165             170             175

Val Leu Cys Gln Asp His Gly Leu Thr Pro Asp Gln Val Val Ala Ile
            180             185             190

Ala Ser Asn Asn Gly Gly Lys Gln Ala Leu Glu Thr Val Gln Arg Leu
        195             200             205

Leu Pro Val Leu Cys Gln Asp His Gly Leu Thr Pro Asp Gln Val Val
        210             215             220
```

-continued

```
Ala Ile Ala Ser Asn Gly Gly Gly Lys Gln Ala Leu Glu Thr Val Gln
225             230             235             240

Arg Leu Leu Pro Val Leu Cys Gln Asp His Gly Leu Thr Pro Asp Gln
                245             250             255

Val Val Ala Ile Ala Ser Asn Asn Gly Gly Lys Gln Ala Leu Glu Thr
            260             265             270

Val Gln Arg Leu Leu Pro Val Leu Cys Gln Asp His Gly Leu Thr Pro
        275             280             285

Asp Gln Val Val Ala Ile Ala Ser Asn Asn Gly Gly Lys Gln Ala Leu
    290             295             300

Glu Thr Val Gln Arg Leu Leu Pro Val Leu Cys Gln Asp His Gly Leu
305             310             315             320

Thr Pro Asp Gln Val Val Ala Ile Ala Ser Asn Asn Gly Gly Lys Gln
                325             330             335

Ala Leu Glu Thr Val Gln Arg Leu Leu Pro Val Leu Cys Gln Asp His
            340             345             350

Gly Leu Thr Pro Asp Gln Val Val Ala Ile Ala Ser Asn Asn Gly Gly
        355             360             365

Lys Gln Ala Leu Glu Thr Val Gln Arg Leu Leu Pro Val Leu Cys Gln
    370             375             380

Asp His Gly Leu Thr Pro Asp Gln Val Val Ala Ile Ala Ser His Asp
385             390             395             400

Gly Gly Lys Gln Ala Leu Glu Thr Val Gln Arg Leu Leu Pro Val Leu
            405             410             415

Cys Gln Asp His Gly Leu Thr Pro Asp Gln Val Val Ala Ile Ala Ser
            420             425             430

Asn Gly Gly Gly Lys Gln Ala Leu Glu Thr Val Gln Arg Leu Leu Pro
        435             440             445

Val Leu Cys Gln Asp His Gly Leu Thr Pro Asp Gln Val Val Ala Ile
    450             455             460

Ala Ser Asn Asn Gly Gly Lys Gln Ala Leu Glu Thr Val Gln Arg Leu
465             470             475             480

Leu Pro Val Leu Cys Gln Asp His Gly Leu Thr Pro Asp Gln Val Val
                485             490             495

Ala Ile Ala Ser His Asp Gly Gly Lys Gln Ala Leu Glu Thr Val Gln
            500             505             510

Arg Leu Leu Pro Val Leu Cys Gln Asp His Gly Leu Thr Pro Asp Gln
            515             520             525

Val Val Ala Ile Ala Ser Asn Gly Gly Gly Lys Gln Ala Leu Glu Thr
        530             535             540

Val Gln Arg Leu Leu Pro Val Leu Cys Gln Asp His Gly Leu Thr Pro
545             550             555             560

Asp Gln Val Val Ala Ile Ala Ser His Asp Gly Gly Lys Gln Ala Leu
            565             570             575

Glu Ser Ile Val Ala Gln Leu Ser Arg Pro Asp Pro Ala Leu Ala Ala
            580             585             590

Leu Thr Asn Asp His Leu Val Ala Leu Ala Cys Leu Gly Gly Arg Pro
        595             600             605

Ala Met Asp Ala Val Lys Lys Gly Leu Pro His Ala Pro Glu Leu Ile
    610             615             620

Arg Arg Val Asn Arg Arg Ile Gly Glu Arg Thr Ser His Arg Val Ala
625             630             635             640
```

-continued

```
Ile Ser Arg Val Gly Gly Ser Ser Arg Arg Glu Ser Ile Asn Pro Trp
            645                 650                 655

Ile Leu Thr Gly Phe Ala Asp Ala Glu Gly Ser Phe Gly Leu Ser Ile
            660                 665                 670

Leu Asn Arg Asn Arg Gly Thr Gly Arg Tyr His Thr Arg Leu Ser Phe
            675                 680                 685

Thr Ile Met Leu His Asn Lys Asp Lys Ser Ile Leu Glu Asn Ile Gln
        690                 695                 700

Ser Thr Trp Lys Val Gly Ser Ile Thr Asn Asn Gly Asp His Tyr Val
705                 710                 715                 720

Ser Leu Val Val Tyr Arg Phe Glu Asp Leu Lys Val Ile Ile Asp His
                725                 730                 735

Phe Glu Lys Tyr Pro Leu Ile Thr Gln Lys Leu Gly Asp Tyr Lys Leu
            740                 745                 750

Phe Lys Gln Ala Phe Ser Val Met Glu Asn Lys Glu His Leu Lys Glu
            755                 760                 765

Asn Gly Ile Lys Glu Leu Val Arg Ile Lys Ala Lys Met Asn Trp Gly
        770                 775                 780

Leu Asn Asp Glu Leu Lys Lys Ala Phe Pro Glu Asn Ile Ser Lys Glu
785                 790                 795                 800

Arg Pro Leu Ile Asn Lys Asn Ile Pro Asn Phe Lys Trp Leu Ala Gly
                805                 810                 815

Phe Thr Ser Gly Asp Gly Ser Phe Phe Val Arg Leu Arg Lys Ser Asn
            820                 825                 830

Val Asn Ala Arg Val Arg Val Gln Leu Val Phe Glu Ile Ser Gln His
            835                 840                 845

Ile Arg Asp Lys Asn Leu Met Asn Ser Leu Ile Thr Tyr Leu Gly Cys
        850                 855                 860

Gly His Ile Tyr Glu Gly Asn Lys Ser Glu Arg Ser Trp Leu Gln Phe
865                 870                 875                 880

Arg Val Glu Lys Phe Ser Asp Ile Asn Asp Lys Ile Ile Pro Val Phe
                885                 890                 895

Gln Glu Asn Thr Leu Ile Gly Val Lys Leu Glu Asp Phe Glu Asp Trp
            900                 905                 910

Cys Lys Val Ala Lys Leu Ile Glu Glu Lys Lys His Leu Thr Glu Ser
            915                 920                 925

Gly Leu Asp Glu Ile Lys Lys Ile Lys Leu Asn Met Asn Lys Gly Arg
        930                 935                 940
```

<210> SEQ ID NO 20
<211> LENGTH: 944
<212> TYPE: PRT
<213> ORGANISM: Artificial Sequence
<220> FEATURE:
<223> OTHER INFORMATION: Made in Lab - engineered PDCD-1 megaTAL
    polypeptide

<400> SEQUENCE: 20

```
Met Gly Ser Cys Arg Pro Pro Lys Lys Arg Lys Val Val Asp Leu
1               5               10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60
```

```
Gly Thr Val Ala Val Thr Tyr Gln His Ile Ile Thr Ala Leu Pro Glu
65                  70                  75                  80

Ala Thr His Glu Asp Ile Val Gly Val Gly Lys Gln Trp Ser Gly Ala
                85                  90                  95

Arg Ala Leu Glu Ala Leu Leu Thr Asp Ala Gly Glu Leu Arg Gly Pro
            100                 105                 110

Pro Leu Gln Leu Asp Thr Gly Gln Leu Val Lys Ile Ala Lys Arg Gly
            115                 120                 125

Gly Val Thr Ala Met Glu Ala Val His Ala Ser Arg Asn Ala Leu Thr
        130                 135                 140

Gly Ala Pro Leu Asn Leu Thr Pro Asp Gln Val Val Ala Ile Ala Ser
145                 150                 155                 160

Asn Asn Gly Gly Lys Gln Ala Leu Glu Thr Val Gln Arg Leu Leu Pro
                165                 170                 175

Val Leu Cys Gln Asp His Gly Leu Thr Pro Asp Gln Val Val Ala Ile
            180                 185                 190

Ala Ser Asn Asn Gly Gly Lys Gln Ala Leu Glu Thr Val Gln Arg Leu
            195                 200                 205

Leu Pro Val Leu Cys Gln Asp His Gly Leu Thr Pro Asp Gln Val Val
        210                 215                 220

Ala Ile Ala Ser Asn Gly Gly Lys Gln Ala Leu Glu Thr Val Gln
225                 230                 235                 240

Arg Leu Leu Pro Val Leu Cys Gln Asp His Gly Leu Thr Pro Asp Gln
                245                 250                 255

Val Val Ala Ile Ala Ser Asn Asn Gly Gly Lys Gln Ala Leu Glu Thr
            260                 265                 270

Val Gln Arg Leu Leu Pro Val Leu Cys Gln Asp His Gly Leu Thr Pro
            275                 280                 285

Asp Gln Val Val Ala Ile Ala Ser Asn Asn Gly Gly Lys Gln Ala Leu
        290                 295                 300

Glu Thr Val Gln Arg Leu Leu Pro Val Leu Cys Gln Asp His Gly Leu
305                 310                 315                 320

Thr Pro Asp Gln Val Val Ala Ile Ala Ser Asn Asn Gly Gly Lys Gln
                325                 330                 335

Ala Leu Glu Thr Val Gln Arg Leu Leu Pro Val Leu Cys Gln Asp His
            340                 345                 350

Gly Leu Thr Pro Asp Gln Val Val Ala Ile Ala Ser Asn Asn Gly Gly
            355                 360                 365

Lys Gln Ala Leu Glu Thr Val Gln Arg Leu Leu Pro Val Leu Cys Gln
        370                 375                 380

Asp His Gly Leu Thr Pro Asp Gln Val Val Ala Ile Ala Ser His Asp
385                 390                 395                 400

Gly Gly Lys Gln Ala Leu Glu Thr Val Gln Arg Leu Leu Pro Val Leu
                405                 410                 415

Cys Gln Asp His Gly Leu Thr Pro Asp Gln Val Val Ala Ile Ala Ser
            420                 425                 430

Asn Gly Gly Gly Lys Gln Ala Leu Glu Thr Val Gln Arg Leu Leu Pro
            435                 440                 445

Val Leu Cys Gln Asp His Gly Leu Thr Pro Asp Gln Val Val Ala Ile
        450                 455                 460

Ala Ser Asn Asn Gly Gly Lys Gln Ala Leu Glu Thr Val Gln Arg Leu
465                 470                 475                 480
```

-continued

```
Leu Pro Val Leu Cys Gln Asp His Gly Leu Thr Pro Asp Gln Val Val
                485                 490                 495

Ala Ile Ala Ser His Asp Gly Gly Lys Gln Ala Leu Glu Thr Val Gln
                500                 505                 510

Arg Leu Leu Pro Val Leu Cys Gln Asp His Gly Leu Thr Pro Asp Gln
            515                 520                 525

Val Val Ala Ile Ala Ser Asn Gly Gly Gly Lys Gln Ala Leu Glu Thr
    530                 535                 540

Val Gln Arg Leu Leu Pro Val Leu Cys Gln Asp His Gly Leu Thr Pro
545                 550                 555                 560

Asp Gln Val Val Ala Ile Ala Ser His Asp Gly Gly Lys Gln Ala Leu
                565                 570                 575

Glu Ser Ile Val Ala Gln Leu Ser Arg Pro Asp Pro Ala Leu Ala Ala
            580                 585                 590

Leu Thr Asn Asp His Leu Val Ala Leu Ala Cys Leu Gly Gly Arg Pro
            595                 600                 605

Ala Met Asp Ala Val Lys Lys Gly Leu Pro His Ala Pro Glu Leu Ile
    610                 615                 620

Arg Arg Val Asn Arg Arg Ile Gly Glu Arg Thr Ser His Arg Val Ala
625                 630                 635                 640

Ile Ser Arg Val Gly Gly Ser Ser Arg Arg Glu Ser Ile Asn Pro Trp
            645                 650                 655

Ile Leu Thr Gly Phe Ala Asp Ala Glu Gly Ser Phe Gly Leu Ser Ile
            660                 665                 670

Leu Asn Arg Asn Arg Gly Thr Ala Arg Tyr His Thr Arg Leu Ser Phe
            675                 680                 685

Thr Ile Met Leu His Asn Lys Asp Lys Ser Ile Leu Glu Asn Ile Gln
    690                 695                 700

Ser Thr Trp Lys Val Gly Ser Ile Tyr Asn Asn Gly Asp His Tyr Val
705                 710                 715                 720

Ser Leu Glu Val Phe Arg Phe Glu Asp Leu Lys Val Ile Ile Asp His
            725                 730                 735

Phe Glu Lys Tyr Pro Leu Ile Thr Gln Lys Leu Gly Asp Tyr Lys Leu
            740                 745                 750

Phe Lys Gln Ala Phe Ser Val Met Glu Asn Lys Glu His Leu Lys Glu
            755                 760                 765

Asn Gly Ile Lys Glu Leu Val Arg Ile Lys Ala Lys Met Asn Trp Gly
    770                 775                 780

Leu Asn Asp Glu Leu Lys Lys Ala Phe Pro Glu Asn Ile Ser Lys Glu
785                 790                 795                 800

Arg Pro Leu Ile Asn Lys Asn Ile Pro Asn Phe Lys Trp Leu Ala Gly
            805                 810                 815

Phe Thr Ser Gly Asp Gly Ser Phe Phe Val Arg Leu Arg Lys Ser Asn
            820                 825                 830

Val Asn Ala Arg Val Arg Val Gln Leu Val Phe Glu Ile Ser Gln His
    835                 840                 845

Ile Arg Asp Lys Asn Leu Met Asn Ser Leu Ile Thr Tyr Leu Gly Cys
    850                 855                 860

Gly His Ile Tyr Glu Gly Asn Lys Ser Glu Arg Ser Trp Leu Gln Phe
865                 870                 875                 880

Arg Val Glu Lys Phe Ser Asp Ile Asn Asp Lys Ile Ile Pro Val Phe
            885                 890                 895

Gln Glu Asn Thr Leu Ile Gly Val Lys Leu Glu Asp Phe Glu Asp Trp
```

```
              900                 905                 910

Cys Lys Val Ala Lys Leu Ile Glu Glu Lys Lys His Leu Thr Glu Ser
         915                 920                 925

Gly Leu Asp Glu Ile Lys Lys Ile Lys Leu Asn Met Asn Lys Gly Arg
     930                 935                 940

<210> SEQ ID NO 21
<211> LENGTH: 3
<212> TYPE: PRT
<213> ORGANISM: Artificial Sequence
<220> FEATURE:
<223> OTHER INFORMATION: Exemplary linker sequence

<400> SEQUENCE: 21

Gly Gly Gly
1

<210> SEQ ID NO 22
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 22

Asp Gly Gly Gly Ser
1               5

<210> SEQ ID NO 23
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 23

Thr Gly Glu Lys Pro
1               5

<210> SEQ ID NO 24
<211> LENGTH: 4
<212> TYPE: PRT
<213> ORGANISM: Artificial Sequence
<220> FEATURE:
<223> OTHER INFORMATION: Exemplary linker sequence

<400> SEQUENCE: 24

Gly Gly Arg Arg
1

<210> SEQ ID NO 25
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 25

Gly Gly Gly Gly Ser
1               5

<210> SEQ ID NO 26
<211> LENGTH: 14
<212> TYPE: PRT
<213> ORGANISM: Artificial Sequence
<220> FEATURE:
```

-continued

<223> OTHER INFORMATION: Exemplary linker sequence

<400> SEQUENCE: 26

Glu Gly Lys Ser Ser Gly Ser Gly Ser Glu Ser Lys Val Asp
1               5                   10

<210> SEQ ID NO 27
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 27

Lys Glu Ser Gly Ser Val Ser Ser Glu Gln Leu Ala Gln Phe Arg Ser
1               5                   10                  15

Leu Asp

<210> SEQ ID NO 28
<211> LENGTH: 8
<212> TYPE: PRT
<213> ORGANISM: Artificial Sequence
<220> FEATURE:
<223> OTHER INFORMATION: Exemplary linker sequence

<400> SEQUENCE: 28

Gly Gly Arg Arg Gly Gly Gly Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Exemplary linker sequence

<400> SEQUENCE: 29

Leu Arg Gln Arg Asp Gly Glu Arg Pro
1               5

<210> SEQ ID NO 30
<211> LENGTH: 12
<212> TYPE: PRT
<213> ORGANISM: Artificial Sequence
<220> FEATURE:
<223> OTHER INFORMATION: Exemplary linker sequence

<400> SEQUENCE: 30

Leu Arg Gln Lys Asp Gly Gly Gly Ser Glu Arg Pro
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Exemplary linker sequence

<400> SEQUENCE: 31

Leu Arg Gln Lys Asp Gly Gly Gly Ser Gly Gly Gly Ser Glu Arg Pro
1               5                   10                  15

<210> SEQ ID NO 32
<211> LENGTH: 7
<212> TYPE: PRT
<213> ORGANISM: Artificial Sequence

```
<220> FEATURE:
<223> OTHER INFORMATION: Cleavage sequence by TEV protease
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa = Gly or Ser

<400> SEQUENCE: 32

Glu Xaa Xaa Tyr Xaa Gln Xaa
1               5

<210> SEQ ID NO 33
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 33

Glu Asn Leu Tyr Phe Gln Gly
1               5

<210> SEQ ID NO 34
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 34

Glu Asn Leu Tyr Phe Gln Ser
1               5

<210> SEQ ID NO 35
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 35

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 36
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 36

Ala Thr Asn Phe Ser Leu Leu Lys Gln Ala Gly Asp Val Glu Glu Asn
1               5                   10                  15

Pro Gly Pro

<210> SEQ ID NO 37
```

```
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 37

Leu Leu Lys Gln Ala Gly Asp Val Glu Glu Asn Pro Gly Pro
1               5                   10

<210> SEQ ID NO 38
<211> LENGTH: 21
<212> TYPE: PRT
<213> ORGANISM: Artificial Sequence
<220> FEATURE:
<223> OTHER INFORMATION: Self-cleaving polypeptide comprising 2A site

<400> SEQUENCE: 38

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 39
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 39

Glu Gly Arg Gly Ser Leu Leu Thr Cys Gly Asp Val Glu Glu Asn Pro
1               5                   10                  15

Gly Pro

<210> SEQ ID NO 40
<211> LENGTH: 13
<212> TYPE: PRT
<213> ORGANISM: Artificial Sequence
<220> FEATURE:
<223> OTHER INFORMATION: Self-cleaving polypeptide comprising 2A site

<400> SEQUENCE: 40

Leu Leu Thr Cys Gly Asp Val Glu Glu Asn Pro Gly Pro
1               5                   10

<210> SEQ ID NO 41
<211> LENGTH: 23
<212> TYPE: PRT
<213> ORGANISM: Artificial Sequence
<220> FEATURE:
<223> OTHER INFORMATION: Self-cleaving polypeptide comprising 2A site

<400> SEQUENCE: 41

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 42
<211> LENGTH: 20
<212> TYPE: PRT
<213> ORGANISM: Artificial Sequence
<220> FEATURE:
<223> OTHER INFORMATION: Self-cleaving polypeptide comprising 2A site
```

-continued

```
<400> SEQUENCE: 42

Gln Cys Thr Asn Tyr Ala Leu Leu Lys Leu Ala Gly Asp Val Glu Ser
1               5                   10                  15

Asn Pro Gly Pro
            20

<210> SEQ ID NO 43
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 43

Leu Leu Lys Leu Ala Gly Asp Val Glu Ser Asn Pro Gly Pro
1               5                   10

<210> SEQ ID NO 44
<211> LENGTH: 25
<212> TYPE: PRT
<213> ORGANISM: Artificial Sequence
<220> FEATURE:
<223> OTHER INFORMATION: Self-cleaving polypeptide comprising 2A site

<400> SEQUENCE: 44

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 45
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 45

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 46
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 46

Leu Leu Lys Leu Ala Gly Asp Val Glu Ser Asn Pro Gly Pro
1               5                   10

<210> SEQ ID NO 47
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 47

Leu Leu Asn Phe Asp Leu Leu Lys Leu Ala Gly Asp Val Glu Ser Asn
1               5                   10                  15
```

-continued

Pro Gly Pro

<210> SEQ ID NO 48
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 48

Thr Leu Asn Phe Asp Leu Leu Lys Leu Ala Gly Asp Val Glu Ser Asn
1               5                   10                  15

Pro Gly Pro

<210> SEQ ID NO 49
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 49

Leu Leu Lys Leu Ala Gly Asp Val Glu Ser Asn Pro Gly Pro
1               5                   10

<210> SEQ ID NO 50
<211> LENGTH: 17
<212> TYPE: PRT
<213> ORGANISM: Artificial Sequence
<220> FEATURE:
<223> OTHER INFORMATION: Self-cleaving polypeptide comprising 2A site

<400> SEQUENCE: 50

Asn Phe Asp Leu Leu Lys Leu Ala Gly Asp Val Glu Ser Asn Pro Gly
1               5                   10                  15

Pro

<210> SEQ ID NO 51
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 51

Gln Leu Leu Asn Phe Asp Leu Leu Lys Leu Ala Gly Asp Val Glu Ser
1               5                   10                  15

Asn Pro Gly Pro
            20

<210> SEQ ID NO 52
<211> LENGTH: 24
<212> TYPE: PRT
<213> ORGANISM: Artificial Sequence
<220> FEATURE:
<223> OTHER INFORMATION: Self-cleaving polypeptide comprising 2A site

<400> SEQUENCE: 52

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 53

```
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 53

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr
        35                  40

<210> SEQ ID NO 54
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 54

Leu Asn Phe Asp Leu Leu Lys Leu Ala Gly Asp Val Glu Ser Asn Pro
1               5                   10                  15

Gly Pro

<210> SEQ ID NO 55
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 55

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 56
<211> LENGTH: 33
<212> TYPE: PRT
<213> ORGANISM: Artificial Sequence
<220> FEATURE:
<223> OTHER INFORMATION: Self-cleaving polypeptide comprising 2A site

<400> SEQUENCE: 56

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 57
<211> LENGTH: 7
<212> TYPE: PRT
<213> ORGANISM: Homo sapiens

<400> SEQUENCE: 57

Met Gln Ile Pro Gln Ala Pro
1               5
```

<210> SEQ ID NO 58
<211> LENGTH: 44
<212> TYPE: DNA
<213> ORGANISM: Homo sapiens

<400> SEQUENCE: 58
ctctggtggg gctgctccag gcatgcagat cccacaggcg ccct                        44

<210> SEQ ID NO 59
<211> LENGTH: 44
<212> TYPE: DNA
<213> ORGANISM: Homo sapiens

<400> SEQUENCE: 59
agggcgcctg tgggatctgc atccctggag cagccccacc agag                        44

<210> SEQ ID NO 60
<211> LENGTH: 8
<212> TYPE: PRT
<213> ORGANISM: Homo sapiens

<400> SEQUENCE: 60

Asn Gly Arg Asp Phe His Met Ser
1               5

<210> SEQ ID NO 61
<211> LENGTH: 43
<212> TYPE: DNA
<213> ORGANISM: Homo sapiens

<400> SEQUENCE: 61
gtgtcacaca actgcccaac gggcgtgact tccacatgag cgt                         43

<210> SEQ ID NO 62
<211> LENGTH: 43
<212> TYPE: DNA
<213> ORGANISM: Homo sapiens

<400> SEQUENCE: 62
acgctcatgt ggaagtcacg cccgttgggc agttgtgtga cac                         43

<210> SEQ ID NO 63
<211> LENGTH: 8
<212> TYPE: PRT
<213> ORGANISM: Homo sapiens

<400> SEQUENCE: 63

Glu Gln Thr Glu Tyr Ala Thr Ile
1               5

<210> SEQ ID NO 64
<211> LENGTH: 43
<212> TYPE: DNA
<213> ORGANISM: Homo sapiens

<400> SEQUENCE: 64

-continued

```
tgagcagacg gagtatgcca ccattgtctt tcctagcgga atg                43

<210> SEQ ID NO 65
<211> LENGTH: 43
<212> TYPE: DNA
<213> ORGANISM: Homo sapiens

<400> SEQUENCE: 65
cattccgcta ggaaagacaa tggtggcata ctccgtctgc tca                43
```